US006756212B1

(12) United States Patent
Curtis et al.

(10) Patent No.: US 6,756,212 B1
(45) Date of Patent: Jun. 29, 2004

(54) ISOLATED PROTEINS AND NUCLEIC ACID MOLECULES HAVING HOMOLOGY TO THE NIP2 PROTEIN AND USES THEREOF

(75) Inventors: Rory A. J. Curtis, Southborough, MA (US); M. Alexandra Glucksmann, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/174,937

(22) Filed: Oct. 19, 1998

(51) Int. Cl.[7] .................. C12P 21/02; C12N 15/12; C12N 1/00; C12N 5/10; C12N 15/63
(52) U.S. Cl. ............... 435/69.1; 435/320.1; 435/252.3; 435/252.33; 435/244.11; 435/325; 435/410; 536/235
(58) Field of Search ............... 435/69.1, 252.3, 435/252.33, 254.11, 520.1, 320.1, 325, 410; 536/23.5

(56) References Cited

FOREIGN PATENT DOCUMENTS

EP        733706      9/1996

OTHER PUBLICATIONS

Adams, M.D. et al. "Sequence identification of 2,375 human brain genes," *Nature*, 355:632–634 (Feb. 1992).
Adams, M.D. et al. "3,400 New expressed sequence tags identify diversity of transcripts in human brain," *Nature Genetics*, 4:256–267 (Jul. 1993).
Adams, M.D. et al. "Rapid cDNA sequencing (expressed sequence tags) from a directionally cloned human infant brain cDNA library." *Nature Genetics*, 4:373–380 (Aug. 1993).
Adams, M.D. et al. "Initial assessment of human gene diversity and expression patterns based upon 83 million nucleotides of cDNA sequence," *Nature*, 377:3–17 (Sep. 1995).
Barfod, E.T. et al. "Cloning and expression of human CDC42 GTPase–activating protein reveals a functional SH3–binding domain," *J. Biol. Chem.*, 268 26059–26062 (Dec. 1993).
Barrett, T. et al. "The structure of the GTPase–activating domain from p50ohroGAP," *Nature*, 385:458–461 (Jan. 1997).
Boyd, J.M. et al. "Adenovirus E1B 19 kDa and Bcl–2 proteins interact with a common set of cellular proteins," *Cell*, 79:341–351 (Oct. 1994).
Boyd, J.M. et al. "Bik,a novel death–inducing protein shares a distinct sequence motif with Bcl–2 family proteins and interacts with viral and cellular survival–promoting proteins," *Oncogene* vol. 11, No. 9, 1921–1928 (1995).
Chen, G. et al. "The E1B 19K/Bcl–2–binding protein Nip3 is a dimeric mitochondrial protein that activates apoptosis," *J. Exp. Med.*, 186:1975–1983 (Dec. 1997).
Chittenden, T. et al. "A conserved domain in Bak, distinct from BH1 and BH2, mediates cell death and protein binding functions," *EMBO Journal*, 14:5589–5596 (1995).
Chuang, Y.C. et al. "Molecular analysis and expression of the extracellular lipase of *Aromonas hydrophila* MCL–2," *Cell*, 79:341–351 (Oct. 1994).
Debuchy, R. et al., "The mating types of *Podospora anserina:* functional analysis and sequence of the fertilization domains," *Mol. Gen. Genet.*, 233:113–121 (1992).
Garrett, M.D. et al., "Purification and N–terminal sequence of the p21rho GTPase–activating protein, rho GAP," *Biochem. J.*, 276:833–836 (1991).
Inohara, N. et al., "Harakiri, a novel regulator of cell death, encodes a protein that activates apoptosis and interacts selectively with survival–promoting proteins Bcl–2 and Bcl–XI," *EMBO J.*, 16:1686–1694 (1997).
Lancaster, C.A. et al., "Characterization of rhoGAP," *J. Biol. Chem.*, 269(2): 1137–1142 (1994).
Nagase, T. et al., "Prediction of the coding sequences of unidentified human genes. VII. The complete sequences of 100 new cDNA clones from brain which can code for large proteins in vitro," *DNA Res.*, 4:141–150 (1997).
Rittinger, K. et al., "Crystal structure of a small G protein in complex with the GTPase–activating protein rhoGAP," *Nature*, 388:693–697 (Aug. 1997).
Rogers, S. et al., "Amino acid sequences common to rapidly degraded proteins: The PEST hypothesis," *Science*, 234:364–368 (Oct. 1986).
Salehuzzaman, S.N.I.M. et al., "Isolation and characterization of a cDNA encoding granule–bound starch synthase in cassava (*Manihot esculenta Crantz*) and its antisense expression in potato," *Plant Molecular Biology*, 23:947–962 (1993).
Stern, D.L., "A phylogenetic analysis of soldier evolution in the aphid family *hormaphididae*," *Proc. R. Soc. Lond.*, 256:203–209 (1994).
Wang, K. et al., "BID: A novel BH3 domain–only death agonist," *Genes & Development*, 10:2859–2869 (1996).
Wilson, R. et al., "2.2 Mb of contiguous nucleotide sequence from chromosome III of *C. elegans*," *Nature*, 368:32–38 (Mar. 1994).

(List continued on next page.)

*Primary Examiner*—Gabriele Bugaisky
(74) *Attorney, Agent, or Firm*—Lahive & Cockfield LLP

(57) ABSTRACT

The invention provides isolated nucleic acids molecules, designated NIP2b, NIP2cL, and NIP2cS nucleic acid molecules, which encode novel NIP2 family members. The invention also provides antisense nucleic acid molecules, recombinant expression vectors containing NIP2b, NIP2cL, and NIP2cS nucleic acid molecules, host cells into which the expression vectors have been introduced, and nonhuman transgenic animals in which a NIP2b, NIP2cL, and NIP2cS gene has been introduced or disrupted. The invention still further provides isolated NIP2b, NIP2cL, and NIP2cS proteins, fusion proteins, antigenic peptides and anti-NIP2b, NIP2cL, and NIP2cS antibodies. Diagnostic methods utilizing compositions of the invention are also provided.

24 Claims, 16 Drawing Sheets

OTHER PUBLICATIONS

Yasuda, M. et al., "Adenovirus E1B–19K/BCL–2 interacting protein BNIP3 contains a BH3 domain and a mitochondrial targeting sequence," *J. Biol. Chem.,* 273(20):12415–12421 (1998).

Zamzami, N. et al., "Mitochondrial control of nuclear apoptosis," *J. Exp. Med.,* 183:1533–1544 (Apr. 1996).

GenBank™ Accession No. 1082428 for GTPase–activating protein rhoGAP–human; Apr. 26, 1996.

GenBank™ Accession No. AA450831 for vg55e03.rl Beddington mouse embryonic region *Mus musculus* cDNA clone Image:865276; Jun. 4, 1997.

GenBank™ Accession No. AA504063 for nh40g09.s1 nci_cgap_pr5 *Homo sapiens* cDNA clone IMAGE:954880; Aug. 20, 1997.

GenBank™ Accession No. AA843788 for ak09a04.s1 *Homo sapiens* cDNA clone Image:1405422; Jan. 1999.

GenBank™ Accession No. AA862376 for *Homo sapiens* cDNA clone image: 1455963; Mar. 11, 1998.

GenBank Accession No. AA893125 for Bento soares rattus sp. CDNA clone RKIBC44 3' end; Jun. 18, 1998.

GenBank™ Accession No. AA8914577 for soares mouse mammary gland NbMMG *Mus musculus* cDNAclone image: 1314564; Apr. 14, 1998.

GenBank™ Accession No. AB002365 for klAA0367; Jun. 23, 1997.

GenBank™ Accession No. AF035207 for *Mus musculus* Nip21 mRNA; Feb. 26, 1998.

GenBank™ Accession No. AL000418 for clone 010H20aD1; Sep. 18, 1997.

GenBank™ Accession No. AL005822 for clone 147G20aA6; Sep. 18, 1997.

GenBank™ Accession No. AL005858 for clone 147G20aE10; Sep. 18, 1997.

GenBank™ Accession No. D61567 for *Homo sapiens* cDNA clone GEN–418G12 5'; Dec. 14, 1995.

GenBank™ Accession No. L38298 for cytochrome oxidase subunit I; Mar. 5, 1997.

GenBank™ M78376 for *Homo sapiens* cDNA clone HFBCA94; May 26, 1992.

GenBank™ Accession No. P35693 for MAT+ sexual cell fertilisation promoting factor; Nov. 1, 1997.

GenBank™ Accession No. Q07960 for GTPase–activating protein rhoGAP; Dec. 18, 1998.

GenBank™ Accession No. Q43784 for Granule–bound glycogen (starch) synthase precursor.

GenBank™ Accession No. T32180 for EST 44614 Human brain *Homo sapiens* cDNA 5' end similar to None; Sep. 6, 1995.

GenBank™ Accession No. T05645 for *Homo sapiens* cDNA clone HFBDD71; Jun. 30, 1993.

GenBank™ Accession No. T08680 for Bento soares *Homo Sapiens* cDNA clone HIBBI25 5' end; Aug. 3, 1993.

GenBank™ Accession No. U15173 for BCL2/adenovirus E1B 19kD–interacting protein 2; Feb. 2, 1998.

GenBank™ Accession No. U63543 for Extracellular lipase; Apr. 15, 1997.

GenBank™ Accession No. W00998 for *Homo sapiens* cDNA clone image: 296509 5'; Apr. 18, 1996.

```
Input file 57h8Bcons; Output File 57h8Btra
Sequence length 3076
```

CCACGCGTCCGCCCACGCGTCCGGGAAGAAGCAGCTACCTCGGAGGCAGGGCGCGCAGGCGGGCGGCGATGAGAGGGGG

CGCAGCCGCAGCCCCGCGCTGGGGAGCCCACCGCTAACCCTGCACCCCACCCACCCCTGCACAAAAGAGCTGGCGGGCG

CTGGCCACGTCGCCCTGGGTGACCTTCCTCGGATGCAGAATCCGCCCCTGCGAGCATCCTCTTCCTCCTAGGCTCTGAA

GGCCCGGGGAGCGTGAGCGATGCCCAGCTGCACCCGGGCAGGGCTCGCCTTTGTTTGCCAGTAAGGAGGAGAGGCTGTC

```
                                                              M   G   T   T   E   A
TCAGCTGCAGAGGGGTCATCCCTGCTTCAAGCCAGTGCCTCTTCCCAGCTCCC ATG GGG ACC ACC GAA GCC

T   L   R   M   E   N   V   D   V   K   E   E   W   Q   D   E   D   L   P   R
 ACG CTC CGG ATG GAA AAC GTG GAC GTG AAG GAG GAA TGG CAG GAC GAA GAT CTT CCC AGG

P   L   P   E   E   T   G   V   E   L   L   G   S   P   V   E   D   T   S   S
 CCA CTC CCA GAA GAG ACG GGG GTG GAA CTG CTT GGC AGC CCG GTG GAA GAC ACA TCC TCT

P   P   N   T   L   N   F   N   G   A   H   R   K   R   K   T   L   V   A   P
 CCT CCC AAC ACG CTA AAT TTC AAC GGA GCG CAT CGT AAG AGG AAG ACG CTG GTG GCC CCA

E   I   N   I   S   L   D   Q   S   E   G   S   L   L   S   D   D   F   L   D
 GAG ATC AAC ATT TCT CTG GAT CAG AGT GAG GGG TCC CTG CTG TCC GAT GAC TTC TTG GAT

T   P   D   D   L   D   I   N   V   D   D   I   E   T   P   D   E   T   D   S
 ACC CCT GAT GAC CTG GAT ATT AAC GTG GAT GAC ATC GAG ACC CCC GAT GAG ACC GAC TCG

L   E   F   L   G   N   G   N   E   L   E   W   E   D   D   T   P   V   A   T
 CTG GAG TTC CTG GGG AAT GGC AAC GAA CTG GAG TGG GAA GAC GAC ACC CCC GTG GCC ACC

A   K   N   M   P   G   D   S   A   D   L   F   G   D   G   T   T   E   D   G
 GCC AAG AAC ATG CCC GGG GAC AGC GCG GAT CTA TTT GGG GAC GGC ACG ACG GAG GAC GGC

S   A   A   N   G   R   L   W   R   T   V   I   I   G   E   Q   E   H   R   I
 AGC GCC GCC AAC GGG CGC CTG TGG CGG ACA GTG ATC ATC GGG GAG CAA GAG CAC CGT ATA

D   L   H   M   I   R   P   Y   M   K   V   V   T   H   G   G   Y   Y   G   E
 GAC CTG CAC ATG ATC CGG CCT TAC ATG AAA GTG GTC ACC CAC GGA GGG TAC TAC GGC GAA

G   L   N   A   I   I   V   F   A   A   C   F   L   P   D   S   S   L   P   D
 GGC CTC AAC GCC ATC ATC GTC TTC GCA GCC TGC TTC CTT CCA GAC AGC AGC CTC CCC GAC

Y   H   Y   I   M   E   N   L   F   L   Y   V   I   S   S   L   E   L   L   V
 TAC CAC TAC ATC ATG GAG AAC CTC TTC CTG TAC GTC ATC AGC AGC TTA GAG CTC CTG GTG

A   E   D   Y   M   I   V   Y   L   N   G   A   T   P   R   R   M   P   G
 GCT GAG GAC TAC ATG ATC GTG TAC CTC AAC GGT GCC ACG CCC CGG CGG AGG ATG CCT GGA

I   G   W   L   K   K   C   Y   Q   M   I   D   R   R   L   R   K   N   L   K
 ATC GGC TGG CTG AAG AAG TGC TAC CAG ATG ATC GAC CGG AGG TTG CGG AAA AAC CTG AAG

S   L   I   I   V   H   P   S   W   F   I   R   T   V   L   A   I   S   R   P
 TCC TTG ATC ATC GTC CAC CCC TCG TGG TTC ATT CGG ACT GTG CTG GCC ATC TCT CGC CCT

F   I   S   V   K   F   I   N   K   I   Q   Y   V   H   S   L   E   D   L   E
 TTC ATC AGC GTC AAG TTC ATC AAC AAG ATC CAG TAC GTG CAC AGC TTG GAA GAC CTG GAG
```

*Fig. 1A*

```
  Q   L   I   P   M   E   H   V   Q   I   P   D   C   V   L   Q   Y   E   E   E
 CAA CTC ATC CCT ATG GAA CAC GTC CAG ATC CCA GAC TGC GTC CTG CAA TAC GAA GAG GAA

R   L   K   A   R   R   E   S   A   R   P   Q   P   E   F   V   L   P   R   S
 AGA CTG AAG GCC AGG AGG GAG AGC GCG AGG CCC CAG CCG GAG TTT GTG CTG CCC AGG TCT

E   E   K   P   E   V   A   P   V   E   N   R   S   A   L   V   S   E   D   Q
 GAA GAG AAG CCA GAG GTG GCA CCA GTG GAA AAC AGG TCT GCT CTG GTC TCA GAA GAT CAG   1

E   T   S   M   S   *
 GAA ACA AGC ATG TCC TGA
```

GGCGACGTGAGCATAACAAAGGACATGGAAGAAGATTCCAGATGCCAGAAAACCTCTGTCAGACGCCCACTGGCCCCAG

ATCTCATCCTGCCTCATCCTGAGTCCCAATCTTCCAAGGGTGCCAGCCCCTCCGTTCATCTCTGAAACCCAGCATCCTT

TTCAGCTGCTTGAAAACATTGTATTTTTTTTTTTAACGATGCAGTATTTGTGCGTTCCAGAAAAGGGCCCAGCTCTGA

GCCCCTCACCCTTCCACACTCACGAACTCTCAGCCGAGGAAGGCAAGAAGCGCAGGGGGTGGCCCGCGTGGCGTCGGTG

GCCTCCGCTCCTGCTCGCAGCCCCTGTGGTCAGAGCTGGATACAAGATTCAAGACCCTTCTCTTGCTTGTCACCCGCTC

CAGGTTGGAGCCACAGACACCCACCGCCACCCCGGCTGGGTCTGCGTCCTTTCCTGTGCCTTTCCCTCCAGAATGCGGC

CTCAGACCTAGAAGCTCAACCCCCCTATGAGGGCCACGTCCTGGGGTAGCTCCTGACCTCCGACCTTATGTCCAAATTT

CACACCCATGGTTTTTCATTTGACCCGCCCCCTTCTCGCTCATAATGACACCCAGCTCCTTTGAGAGGATCAGAGCCCA

TTGCACAAGAAGAGCCGCTGCCAACCATCCTTGTCCTCCGATTGCAAAATGACACCCCAGTAATCTAGAACATTCTCAA

GCCCCTTTAACTCAGATGTCAAGCCACCGGGCAAACCCCGTCAATACCTCCCACCAAGGAATGAGATATGTGGACCTCA

CTGCTCCCCCAACCCAGCGTCAGGCTGGGACACGCCAACGCTGTTCCGGGTTGGAACAGCACAGGCTCAGAAACTGGCT

CTGAAATAGGCAGACCTAGCAAGAGGAAGATACAGGGTATCGGGCGTTTGAGTGTTTCAGAAGTCATTCGGGAAGATAA

ATCCAGTGCGCTGGCCGCAGCCACCTGCATTCAAAGCTTGGACCAGCGGGTTCTTGTTCGGGAGGCAAATTTCCCTAGG

AAAAAGAAGACAGACTTTTCTAATGGGGTCCAAATGCGGATCACTGGTCAGATGGACTCTAGAAGCACTGAGCTCCCTG

TCTCTGGAAGTATTTAAGAAAAGGCTGGGCCAGGCACGATGGCTCACGCCTGTAATCCCAGACTTTGGGAGGCCGAGGC

AGGCGGATCACCTGAGGTGAGGAGTTTGAGAACAGCCTGGCCAACATGGTGAAACCTCATCTCTACTAAAAATACAAAA

ATTAGCCAGGCGTGGTGGCAGGTGCCTGTAATCCCAGCTACTTGGGAGGCTGAGGCATGAGAATCACTTAAACCTGAGA

GGCAGAGGTTACAGTGAGCCAAGATCGTGCCACTGCATTCCAGCCTGGGCGACAGAGCAAGACTCTGTCTCAAAAAAAA

TAAAAAATAATCAGGGCACAGTGGCTCATGCCTGTAATCCCAGCACTCTGGGAGGCTGAGGTGGGTGGATCACCTGAGG

TCAGGAGTTCAAGACCAGCCTGGTGAACATGGCGAAACCCCGTCTCTAATAAAAATACAAAAATTAGCCGGGCATGGTG

GTGCATGCCTG

*Fig. 1B*

```
Input file Athda22f7.seq; Output File Athda22f7.tra
Sequence length 4235
                            M   E   E   E   T   E   F   L   E   L   G   T   R   I
GTCGACCCACGCGTCCGCGGAA ATG GAG GAG GAG ACA GAG TTC CTT GAG CTC GGA ACC AGG ATA S   R   P   N   G   L   L   S   E   D   V   G   M   D   I   P   F   E   E   G
TCA AGA CCA AAT GGA CTA CTG TCA GAG GAT GTA GGA ATG GAC ATC CCC TTT GAA GAG GGC V   L   S   P   S   A   A   D   M   R   P   E   P   P   N   S   L   D   L   N
GTG CTG AGT CCC AGT GCT GCA GAC ATG AGG CCT GAA CCT CCT AAT TCT CTG GAT CTT AAT    1

D   T   H   P   R   R   I   K   L   T   A   P   N   I   N   L   S   L   D   Q
GAC ACT CAT CCT CGG AGA ATC AAG CTC ACA GCC CCA AAT ATC AAT CTT TCT CTG GAC CAA

S   E   G   S   I   L   S   D   D   N   L   D   S   P   D   E   I   D   I   N
AGT GAA GGA TCT ATT CTC TCT GAT GAT AAC TTG GAC AGT CCA GAT GAA ATT GAC ATC AAT

V   D   E   L   D   T   P   D   E   A   D   S   F   E   Y   T   G   H   D   P
GTG GAT GAA CTT GAT ACC CCC GAT GAA GCA GAT TCT TTT GAG TAC ACT GGC CAT GAT CCC

T   A   N   K   D   S   G   Q   E   S   E   S   I   P   E   Y   T   A   E   E
ACA GCC AAC AAA GAT TCT GGC CAA GAG TCA GAG TCT ATT CCA GAA TAT ACG GCC GAA GAG

E   R   E   D   N   R   L   W   M   T   V   V   I   G   E   Q   E   Q   R   I
GAA CGG GAG GAC AAC CGG CTT TGG ATG ACA GTG GTC ATT GGA GAA CAA GAG CAG CGC ATT

D   M   K   V   I   E   P   Y   R   R   V   I   S   H   G   G   D   S   G   Y
GAC ATG AAG GTC ATC GAG CCC TAC AGG AGA GTC ATT TCT CAC GGA GGA GAT TCA GGA TAC

Y   G   D   G   L   N   A   I   I   V   F   A   A   C   F   L   P   D   S   S
TAT GGG GAC GGT CTA AAT GCC ATC ATT GTG TTT GCC GCC TGT TTT CTG CCA GAC AGC AGT

R   A   D   Y   H   Y   V   M   E   N   L   F   L   Y   V   I   S   T   L   E
CGG GCG GAT TAC CAC TAT GTC ATG GAA AAT CTT TTC CTA TAT GTA ATA AGT ACT TTA GAG

L   M   V   A   E   D   Y   M   I   V   Y   L   N   G   A   T   P   R   R   R
TTG ATG GTA GCT GAA GAC TAT ATG ATT GTG TAC TTG AAT GGT GCA ACC CCA AGA AGG AGG

M   P   G   L   G   W   M   K   K   C   Y   Q   M   I   D   R   R   L   R   K
ATG CCA GGG CTA GGC TGG ATG AAG AAA TGC TAC CAG ATG ATT GAC AGA CGG TTG AGG AAG

N   L   K   S   F   I   I   V   H   P   S   W   F   I   R   T   I   L   A   V
AAT TTG AAA TCA TTC ATC ATT GTT CAT CCA TCT TGG TTC ATC AGA ACA ATC CTT GCT GTG

T   R   P   F   I   S   S   K   F   S   S   K   I   K   Y   V   N   S   L   S
ACA CGA CCT TTT ATA AGT TCA AAA TTC AGC AGT AAA ATT AAA TAT GTC AAT AGC TTA TCA
882

E   L   S   G   L   I   P   M   D   C   I   H   I   P   E   S   I   I   N   I
GAA CTC AGT GGG CTG ATC CCA ATG GAT TGC ATC CAC ATT CCA GAG AGC ATC ATC AAT ATT

D   L   K   L   K   E   K   P   *
GAC TTG AAG CTG AAA GAA AAG CCT TAG

TTGGCCATGCTGGAAGAAGAGGATGCTTTTCTGGTTCATGGTTCTGTTGAAACATATCTACCTGAAAGAGACAGGGCTG

ATGTTACCTTTTTCCACTTTGCACTACCTGGTGCCATTCTAAATTTCTAAGGGGAAAAATAGAAAGTTTGTTTACTCTT
```

*Fig. 3A*

```
AAGATATTTTATGAAATTGTGTGTACTTTCCTATTTTGCCAATTATGTGCCTCAAAGATTTTAGTTGAGCCTTAGCAAG
AAAGTAGGACCTTCCATTTCAATACTTCATTAACACGGTGTAGTGATACTTTGTCCCTTAGACTGGTGTTTACCAGTAA
GATACCTTTAATCCACTGTTAAGTATGAGTGGATTTGTTTCCATAGATTAGCTGGATTTCCTTTTGGTGATTGCATTAG
GTTTAAAGTACACAGGTCTCAACTCTCCCCAGGAAAGTTTCCCCTGTTTGACTCCACCTTTAAAATCCTAAGCCTGACT
AGGACAGCCACAAACCACACAAGGTGTAAAACCATCATCAGCTAAGTGCCCGTTTTGTTCTTGTTTACCAGAATCTCCT
TTAACTTCTCAAAGGGAAGCCGGGCTTTCTAATCCACGTCAACTTTATTTTAGTTGTCAAATTGGGCATTATATTTTAT
GTAAATTGGTCTTTTAACATCATTTTCCTGATGAATGTTGGTGACCACCACATTGTGAAATTTAAGAATCCGTGTTGCA
TGTTTGGTAGCTCTCTGAGTTTCAGGCCATAAACTCAGCTCCAGAGGTTACCTTTTAAGTGCCAAGAACTCAAGTGCAA
GGTGGCCTACTCAAAAATCATTTGGTAGCATTCAGTTATTCATGAATTCCTCTCTCGCATGCATTATAAAAAGTGATCT
GCTTTAAAACACCGTAATCTGATCATAGGCTTAAAATTAAATATGAGTATTACTTTCATGTACAAAATATTTCCTTTAT
AGTCTTCATATGCCCTTTAAAATGCCAACAAGATTTCAAGTCTGTAGGCCTCTAGTGAGGTGGGGTGGCAAACCACAGC
TAAGTCTCGCTCACCACTGCAAGCTAAGAATGGTTTTTACATTTTGGGTTGGAAAAATTTTTTTTGAATATTTCATGAC
ACATGAAAATTATTCAAATGTTAGTGCCGATAAATAAAGTGGTACTGAAACACAGCCACACAAACTTGTTTTTGTACTG
TCTACAGCTACTTTCACACTACAGCCGCAGAGCTGAGCAGTTCAGCAGACCGTATGTCCCACAATGCCTAAAACATTGA
CTATGTTTACAGAAAAAGTTTGCTGACCCCTGCTCTAGCAAACGCATCCTTTCCTACTCCACCCCAATTTGTATTTAGA
TAGTTTCTCTAACAGAACGGACAAATGAGGCTGCAAACTAATTTATTTTTGTCAAAAATCAATGTTTTGACATCCACAG
ACAGTGAAATAAAAGAAATGGCTTGCTGAAAAACATGAGGAGTCCTAGCCACAAAATCACTGCTTAGGTTGCAATTGCC
AAAATGAAGCCTTCTTAGAAGCACTTCTTTAGTATATACAGGTGTTGGCTGAAGTCCGTGCCTCACTCTGGGAACCATT
CTTAGTCTCCAGTGTCTCCTATTACAAAGAAGCTGGCAGAAATAAAAATGAAGGGGTGAGAGCGGTTCCACCCTAGTCT
CATGGTGGAAAATTCATTGGGGAGAGCTGTCCAGGATATTTGGAGTCCTGGGTAGAAGGAGCTTGTAACTACTTTAAAG
TCGACATCTTTGCACAGGTGATTGAGTTTCTCTGACCTCATTGCTTCACCTCTGTCTCCTCCCGTCCTTCCGCACGTGC
CCACACACACGCAGTTCAGCCCTCTTTCCTCCATAAGCCTCCATCGTTTTCTCTTTTCTCCTCTTGATCCTTTCAAGCG
AGTATCTTGTTGAATTGTATGTTCTGTTGGATCTCCTCCTTCATAACATCTGGCTTGTTGGACAGAAAAACCCTACAGC
CCACCCCCTCCCACAGCCCACCTCCACTTTTGAAAGCCCAAATTACACCTCTCCCAGAACACAGTGTTGACGTAAATAC
AGTTACCCAATATTCCTGTTTGTTCACCTATTTGCTACTTTCACTCAGTAGCATCCCATTTTGTAAAATGAATTCCATG
GTCACCCTGTCACAGGAAGTAATGAAAAATCCAGTGTTCAGTGTAGTGGTGCAAACCTGAGGGCATAGAGCTGTTCATA
GAGGGCTCTTGTTATAGCCAAACAGACACAGCAACAATCTCACCATTTATATATATATTTTTAACTTGTCCAGCTCATC
TATGGAAAACTACTCAGGTGGTATGCTGTTTGAAGCCTCATCTTCCTACATGAAAATTATGGGCATTTGTCCCAATGAT
TTTGTTTCAGCTGTTCTGTAGGCTGCATAACCACTCTGATATTTAGGTATCTGCTATTTTATTATCTTAAAAGACAAAT
```

*Fig. 3B*

```
TAATTTAATTGCATGTGCTAGGGAAAAGCTACCATGTACATTCACCCCAAGTAAATAGAATCCTAGATGAATCCTAGAA
AAATAATCCCTAAGCAGATAGGTAGACAGAGGTAAACATTCACATGATTTAGCTCTCTAGCTCTTGCACTCTGAACATT
CTTGCTTTGGTTCTGACTTCTGGGAACTGCTTTGCATTTCTCCTATAGATCTGTAGTTAAGGGAACCAAGGGGTCATTG
GGGCAAAAGCATTGTTTCTCAAAGCTCCTTGATTAAGAGAAAGAACAGAAATTTGCACAGAAGATAGTGTCAAGGAGTG
AGAAAGTTTGTTTGAGGGCAGTAGCTCAGTGTGGAAGAAAATCCTGAAGTTTCTGTTGAAGCCATACAATGTTCTATGG
GGTTACTCTCTAAGACATTCTCTGAGGTGTGTGAGGAAGTCACTACTCCTAGCCTTTGTTAAGATGTAATTTTAAATAT
TCAGTTATGGTACTATGTTTGCAACTCTCGTCTTATCACAATGCCTCAGTAGTTTGTTCCCTTAGAAACATTTAGATGT
GCACAAATTAATCTTTTATATATCTAAAGGTTTTTCTATCATGCATTGGATTGCTCAGAATAAAGTGTCTGTTAGACTT
CGTTTTGGTAAATAAATTCTCCATAATGTAGATTAATAATATAAAAGTCTTTAATGACACAATATATCTATATAGCCTC
ACTGTATAATTCAGAAATAAAAATTGATTCTGCAAAAAAAAAAAAAAAAAAAAAAAAAAAAAAAAAAAAAAAAAGGGCG
GCCGC
```

*Fig. 3C*

```
Input file Alhbaa034f09.seq; Output File Alhbaa034f09.tra
Sequence length 2966
```

```
                                                             M   L   K   S   C   S
GTCGACCCACGCGTCCGGGCGAATCTGTATTTCCAGTTAACTGCTCAGAAGAGAG ATG CTG AAG AGC TGT AGT

R   A   S   F   S   P   S   V   R   K   P   P   L   I   L   R   R   L   L   S
CGT GCA TCC TTC TCA CCC TCC GTT AGA AAG CCT CCT CTC ATC CTC AGA AGA CTA CTG TCA

E   D   V   G   M   D   I   P   F   E   E   G   V   L   S   P   S   A   A   D
GAG GAT GTA GGA ATG GAC ATC CCC TTT GAA GAG GGC GTG CTG AGT CCC AGT GCT GCA GAC

M   R   P   E   P   P   N   S   L   D   L   N   D   T   H   P   R   R   I   K
ATG AGG CCT GAA CCT CCT AAT TCT CTG GAT CTT AAT GAC ACT CAT CCT CGG AGA ATC AAG

L   T   A   P   N   I   N   L   S   L   D   Q   S   E   G   S   I   L   S   D
CTC ACA GCC CCA AAT ATC AAT CTT TCT CTG GAC CAA AGT GAA GGA TCT ATT CTC TCT GAT

D   N   L   D   S   P   D   E   I   D   I   N   V   D   E   L   D   T   P   D
GAT AAC TTG GAC AGT CCA GAT GAA ATT GAC ATC AAT GTG GAT GAA CTT GAT ACC CCC GAT

E   A   D   S   F   E   Y   T   G   H   G   K   S   L   S   W   Q   G   Q   S
GAA GCA GAT TCT TTT GAG TAC ACT GGC CAT GGT AAG TCA CTA AGT TGG CAA GGC AAA AGT

*
TAA
```

ATGCTAAATAAGTAAAAGATTTTCTAACAGACCTCTCATTTTTGTGCCAGTGGATCCTTTTTGTGATTTCTAGAAGCTT

CTGTTTTTATTTCAGGTTATAGGTGGCCATGATTGACAGTTTGGAGCCTGACAGAGAAAGTATGGGTCACAGAGGCCAT

ACATAACCATTGCTCTTTATTAACCCCCACTCTGTGCTAGCATTTATGCTAGGCACTGGGGCTGAGGGAAGACTGTTAC

ATGCTGTGTTACAAGAAACCTGGGGCTGGGTTTGCAGGGGAAGAGAATTTAATCAGGATGATAAAATTTGAAGAAGAGA

AATCAGAGCTTGCCAATTTCTTGTATAAGTTCCCACTATCTGCAATGTTCTTTTCCCCAGATCCTTACGTGACTGACTC

CTTCTCTTTATTCAGATGTTAATCAGATGTCACCTCCTCAGAGAAGTCTTCCTTGACCTCTGTAATCAAAGATGCTTCC

CACTTCCCGACTCCCACCACCTAGTCACTCTCTGTCCCAGTGTTCATTTTATTTTCCACGTATCACTAATTCAAATTGT

ATTATTTAACTATTTGTTTGCATCTTTATTGTCTTTCTCTTACCACTCGAATGTATGCTCCACAGGAGCAAGGACTTTA

TATTTGATCCTGCGTCTCCAATAAAGTGGGAAGGAAGGAAGGGATGGTTTAGGGGGAGTGAGAGAAATGATAAAAAAGA

AGATAATTAAAAGTTTTCAGATCATCCAAGACTGACACTCCTGATATGAACTTCAGTCTTTCTTTAGTTCTTTCTCTTA

CTCTATGAAATCTGGTTTAAGAAATATGTACAAATACAATCATTTTTTTTTAAATGGCATTATGTAGTTTCTGTTTCAG

TTCTAGCCAGGGTGGAATTCTCTGAAGTTATAATATTTGAAAGTGAAAGCGAGAGAGTCTGGGACACAGCTATTGCTTT

TATTCATTTTTAAAATTCACGCAATCTTAAAAGCAATACAGTGCCACAATTAAGTGGTGGCCTGACTTTTAGAGACATG

CTAATTCTAGCAGTTCCACTCCTAGAAGAGCATAATTAGAAAATTCACCAAATTAGCTAATTATTTCAACCAATGGTCA

TTGAGCCGACATGAGCAGTGCAGTTCAGACTCTACCTTGACAGAGCTTAAGGCTTTATTTCCTCAAAAAGGAAATGGCT

AAACGACTTGTTTTATAGTCTATTATGCTTAAGTAGAGTTTTTTTTTTTCCATAAGTTATTGGGGTACAGGTGGTATT

*Fig. 5A*

```
TGGTTACATGAGTAAGTTCTTTAGTGTAAGTAGAGATTTTATATTGCATTTTTATCATGTGTGAATTTCTGTAGTTATC
TGGGTAGTTGATTCTGTAGGTTGAAATACACAAATAGGAGGTGAAAGAAGGTCTGGAATTTGTACTATTTCCTGTCATC
CCAGAGAGTCTTCAGCAGCTCCTCTATCCATCCCAGTTGCCCCCTACCAGCTCCTGCTCCTTTCCCTGCTAATATATTG
ACCAAATCCCACAGAAGACTGTGGCATGACCCAACTGGCCCCTCTCTTGCCTCCGGTATTTGCTTCCTTTTTGTCAGGA
GAGCTTTGTCACACCACATCTGAACCTTTTATTTTTAAACATAGTAAAACTGTCGAGCAAAGCAGTGGTGGCTGGGCAA
GCTGGTAATTAACACTGCCACTTGCTGACATGGCTCTTTTAATGTAGTTAACATAGCTGTGTTGAAAGAACCAGTTTAA
TGGCCACAACCCTGTTTTAGGTCTTAAATGCAAAGGACAGAATTGTAAACTAAGTTGAATTTTTAAATCTACCTTAATT
TTCAAATGAAAGATATATAGTCAGAGGTTGAAACTTTGAAAACACAAAGTGCCTCTGAATAGCTATATTTTGTAAACAT
GAGGACATGGATAAGTGACTGTATAAGAGGGTTGGATTATAAATATGTTTGAGTTCTGAAGTATGAAATAAATGCTTGA
AAGCAGCCTGTTTCTTAGGTTTCTCACGCGACCATTTTGAACCAGGAATGTACATTCTAAACAAAATAGGGGTTTTTAA
GGTATAGTTTTTCAAAAACATTTGGGCCATAATTTATTTTCTTTTAATGAATACTTTTTCATTTATATTATATTTTTCG
TGTATATATTTTCATTATATACGTTTCATTATATATTATATATTTGTACTATATATTTTTCATTTATATAGTTTTCATT
GTATATTATATACCTCATTATATTATATAATTCATTATATAGTTTTCATTTAATTTATTTCATTTTATAACTAGAACAA
TGAAGCACAGAGAAGTTAAGTAATTTGCCTAAGGTCACACAGCTCATTGTTGCCCTTAGTTCCTGGCCCATGCTGCTTC
CCAGTGAATATGCTAACAATGAATGGGAAAGGGTCTGTTACCAGATTGGACTTACATACTTGAAGCCAAACATGATAGC
TCTTGCTCACATTTAGGCCTCTTTTTATCCAGTTTTCCTGACTTGCGGGAGACTCTAAAAAAAAAAAAAAAAGGGCGGCC
GC
```

*Fig. 5B*

>PF00335|transmembrane4 4 transmembrane segments integral membrane proteins

Score: 1.28    Seq: 253 293    Model: 192 232
              *CMekIqdWlhnNfIIIagIciGIafIEilgMvFSMCLCRgI*
              C++ I+  L++N+  +  +++    +    +L ++   + +++I
human    253  CYQMIDRRLRKNLKSLIIVHPSWFIRTVLAISRPFISVKFI    293

*Fig. 7*

>MILPAT00063|calret_c calreticulin calcium-binding domain

```
Score: 5.74       Seq: 55 160     Model: 1 124
       REF      xxxxxxxxxxxxxxxxxxxxxxxxxxxx xxxxxxxxxxxxxxxx
               *YTLIYRPDNTFEVLIDNWQVWSMSLETIWDMFLP.PDNPsREIeDPEef
                +T++ R    +  I ++   +S    ++++D+ L+ PD    EI D +
       human 55 DTHPRRIKL-TAPNINLSLDQSEGSILSDDN-LDSPD----EI-DINVD  96

REF      xxxxxxxxxxxxxxxxxxxxxxxxxxxxxxxxxxxxxxxxxxxxxxxx
               KPEDWDvTkaaERqkMDDPQDEEQRWKPEDWDEDKPEHIPDEDAkEPEDW
                + D  E     DP++   +   E +    PE  ++E+         W
       human 97 ELDTPDEADSFEYT-GHDPTA-NKDSGQESE--SIPEYTAEEEREDNRLW 142

REF      xxxxxxxxxxxxxxxxxxx
               DDEMEYEWDPpEEkMIDWPEQMKDEW*
                 +E       +++   + MK
       human 143 MTVVIGE------QEQRID-MKVIE  160
```

*Fig. 8*

>MILPAT00063|calret_c calreticulin calcium-binding domain

Score: 0.66    Seq: 59 96    Model: 1 44

```
REF        xxxxxxxxxxxxxxxxxxxxxxxxxxxxxxxx xxxxxxxxx
          *YTlIYRPDNTFEVlIDNWQVWSMSLETIWDMFLP.PDNPsREIeD*
           +T++ R     + I ++  +S   ++++D+ L+ PD    EI D
human  59  DTHPRRIKL-TAPNINLSLDQSEGSILSDDN-LDSPD----EI-D  96
```

Fig. 9

GAP of:nip2a.pep check: 3241 from:1 to:314

NIP2A | U15173 Homo sapiens BCL2/adenovirus E1B 19kD-interacting protein 2 (BNIP2)

to: nip2b.pep check: 7307 from: 1 to: 371

NIP2B

Symbol comparison table: /usr/local/gcg_9.1/gcgcore/data/rundata/blosum62.cmp

CompCheck: 6430

| | | | |
|---|---|---|---|
| Gap Weight: | 12 | Average Match: | 2.912 |
| Length Weight: | 4 | Average Mismatch: | -2.003 |
| Quality: | 842 | Length: | 371 |
| Ratio: | 2.682 | Gaps: | 5 |
| Percent Similarity: | 67.197 | Percent Identity: | 56.051 |

Match display thresholds for the alignment(s):
| = IDENTITY
: = 2
. = 1 nip2a.pep x nip2b.pep

```
  1 .........MEGVELKEEWQDEDFPIPLPEDDSIEADILAITGPEDQPGS  41
             || |:.|||||||| | ||||:  :|    :    |  .
  1 MGTTEATLRMENVDVKEEWQDEDLPRPLPEETGVELLGSPVEDTSSPPNT  50

42 LEVNG.NKVRKKLMAPDISLTLDPSDGSVLSDD.LDESGEIDL..DGLDT  87
    |  || .: || |.||:|.:.|| |:||.|||| ||   ::|:  | ::|
 51 LNFNGAHRKRKTLVAPEINISLDQSEGSLLSDDFLDTPDDLDINVDDIET 100

88 PSE........NSNEFEWEDDLPKPKTTEVIRKGSITEYTAAEE...KED 126
    | |        | || ||||| |           .  .        |
101 PDETDSLEFLGNGNELEWEDDTPVATAKNMPGDSADLFGDGTTEDGSAAN 150

127 GRRWRMFRIGEQDHRVDMKAIEPYKKVISHGGYYGDGLNAIVVFAVCFMP 176
    || ||   ||||:||:|:   | || ||:>|||||:|||||:||| |':|
151 GRLWRTVIIGEQEHRIDLHMIRPYMKVVTHGGYYGEGLNAIIVFAACFLP 200

177 ESSQPNYRYLMDNLFKYVIGTLELLVAENYMIVYLNGATTRRKMPSLGWL 226
    :|| |.| |:|:||| |||  .||||||||.|||||||||| ||:||  :|||
201 DSSLPDYHYIMENLFLYVISSLELLVAEDYMIVYLNGATPRRRMPGIGWL 250

227 RKCYQQIDRRLRKNLKSLIIVHPSWFIRTLLAVTRPFISSKFSQKIRYVF 276
    :|||| |||||||||||||||||||||||||||.||:.||||| || ||.||
251 KKCYQMIDRRLRKNLKSLIIVHPSWFIRTVLAISRPFISVKFINKIQYVH 300

277 NLAELAELVPMEYVGIPECIKQVDQELNGKQDEPKNEQ............ 314
    .|  :| :|:|||:| ||:|  | ::|   . |     |
301 SLEDLEQLIPMEHVQIPDCVLQYEEERLKARRESARPQPEFVLPRSEEKP 350
                          .
                          .
```

*Fig. 10*

```
GAP of: nip2b.pep   check:7307  from: 1 to: 371
NIP2B to: nip2c.pep   check: 3344   from: 1 to: 322
IP2C Athda22f7
Symbol comparison table:/usr/local/gcg_9.1/gcgcore/data/rundata/blosum62.cmp
CompCheck: 6430

Gap Weight:      12       Average Match:    2.912
        Length Weight:       4       Average Mismatch: -2.003

Quality:     871              Length:      375
                Ratio:   2.705                Gaps:        4
   Percent Similarity:  69.182     Percent Identity:   58.805

Match display thresholds for the alignment(s):
                     | = IDENTITY
                     : = 2
                     . = 1 nip2b.pep x nip2c.pep

1 .MGTTEATLRMENVDVKEEWQDEDLPRPLPEETGVELLGSPVEDTSSPPN  49
        |  |            : ||.  :| | || |  |   :       |||
     1 MEEETEFLELGTRISRPNGLLSEDVGMDIPFEEGV.LSPSAADMRPEPPN  49

50 TLNFNGAHRKRKTLVAPEINISLDQSEGSLLSDDFLDTPDDLDINVDDIE  99
        .|. |   | :|   | ||  ||:||||||||:||||  ||.||::|||||:::
    50 SLDLNDTHPRRIKLTAPNINLSLDQSEGSILSDDNLDSPDEIDINVDELD  99

100 TPDETDSLEFLGNGNELEWEDDTPVATAKNMPGDSADLFGDGTTEDGSAA 149
        ||||   ||  |: |.           ||     |    .:    :  | |:
   100 TPDEADSFEYTGHD...........PTANKDSGQESESIPEYTAEEERED 138

150 NGRLWRTVIIGEQEHRIDLHMIRPYMKVVTHG...GYYGEGLNAIIVFAA 196
        |  |||  ||:|||||  |||:   .|  || :|:.||     ||||:||||||||||
   139 N.RLWMTVVIGEQEQRIDMKVIEPYRRVISHGGDSGYYGDGLNAIIVFAA 187

197 CFLPDSSLPDYHYIMENLFLYVISSLELLVAEDYMIVYLNGATPRRRMPG 246
        |||||||   ||||:|||||||||||.|||:|||||||||||||||||||||||||
   188 CFLPDSSRADYHYVMENLFLYVISTLELMVAEDYMIVYLNGATPRRRMPG 237

247 IGWLKKCYQMIDRRLRKNLKSLIIVHPSWFIRTVLAISRPFISVKFINKI 296
        :||:|||||||||||||||||||| |||||||||||:||:.|||||  || .||
   238 LGWMKKCYQMIDRRLRKNLKSFIIVHPSWFIRTILAVTRPFISSKFSSKI 287

297 QYVHSLEDLEQLIPMEHVQIPDCVLQYEEERLKARRESARPQPEFVLPRS 346
        .||.|| :|  ||||:  :|| ::    :  .  .
   288 KYVNSLSELSGLIPMDCIHIPESIINIDLKLKEKP............... 322
```

*Fig. 11*

GAP of: nip2c.pep  check: 3344  from: 1 to: 322

NIP2C Athda22f7 to: nip2a.pep  check: 3241  from: 1 to: 314

NIP2A | U15173 Homo sapiens BCL2/adenovirus E1B 19kD-interacting protein 2 (BNIP2)

Symbol comparison table:/usr/local/gcg_9.1/gcgcore/data/rundata/blosum62.cmp
CompCheck: 6430

|  |  |  |  |
|---|---|---|---|
| Gap Weight: | 12 | Average Match: | 2.912 |
| Length Weight: | 4 | Average Mismatch: | -2.003 |
| Quality: | 806 | Length: | 331 |
| Ratio: | 2.567 | Gaps: | 6 |
| Percent Similarity: | 67.541 | Percent Identity: | 57.705 |

Match display thresholds for the alignment(s):
```
             | = IDENTITY
             : = 2
             . = 1
``` nip2c.pep x nip2a.pep

```
  1 MEEETEFLELGTRISRPNGLLSEDVGMDIPFEEGVLSPSAADMRPE.PPN  49
                 :   ||  . :| :: : .    |  || |
  1 ..........MEGVELKEEWQDEDFPIPLPEDDSIEADILAITGPEDQPG  40

50 SLDLNDTHPRRIKLTAPNINLSLDQSEGSILSDDNLDSPDEIDINVDELD  99
    ||:.|     |: || ||.|.|.|| |:||:|||| ||    |||:  | ||
 41 SLEVNGNKVRK.KLMAPDISLTLDPSDGSVLSDD.LDESGEIDL..DGLD  86

100 TPDE.ADSFEYTGHDPTANKDSGQESESIPEYTAEEEREDNRLWMTVVIG 148
    || | .. ||:    |      || |||| ||:|| | |      ||
 87 TPSENSNEFEWEDDLPKPKTTEVIRKGSITEYTAAEEKEDGRRWRMFRIG 136

149 EQEQRIDMKVIEPYRRVISHGGDSGYYGDGLNAIIVFAACFLPDSSRADY 198
    ||: |:|||  ||||::|||||       |||||||||||;||| ||:|:||. .|
137 EQDHRVDMKAIEPYKKVISHG...GYYGDGLNAIVVFAVCFMPESSQPNY 183

199 HYVMENLFLYVISTLELMVAEDYMIVYLNGATPRRRMPGLGWMKKCYQMI 248
    |.|:|||  |||  ||||:|||.||||||||||  ||:||  |||::||||  |
184 RYLMDNLFKYVIGTLELLVAENYMIVYLNGATTRRKMPSLGWLRKCYQQI 233

249 DRRLRKNLKSFIIVHPSWFIRTILAVTRPFISSKFSSKIKYVNSLSELSG 298
    |||||||||| |||||||||||:|||||||||||| ||:||  .|.||.
234 DRRLRKNLKSLIIVHPSWFIRTLLAVTRPFISSKFSQKIRYVFNLAELAE 283

299 LIPMDCIHIPESIINIDLKLKEKP....... 322
    |:||: :  ||| |   :| .| |
284 LVPMEYVGIPECIKQVDQELNGKQDEPKNEQ 314
```

ISOLATED PROTEINS AND NUCLEIC ACID MOLECULES HAVING HOMOLOGY TO THE NIP2 PROTEIN AND USES THEREOF

BACKGROUND OF THE INVENTION

Apoptosis or programmed cell death is an essential physiological process of selective elimination of cells in multicellular organisms. This process is invoked during normal organ development and tissue homeostasis and also during certain pathological conditions that result in degenerative diseases. Programmed cell death plays an important role in regulating the multiplication of and pathogenesis by a number of viruses. In virus-infected cells, apoptotic paradigms are initiated as a cellular defensive mechanism to eliminate infected cells. However, a number of viruses encode proteins that suppress apoptosis resulting in efficient viral replication and pathogenesis. Human adenovinises have evolved multiple strategies employing proteins coded by three different gene blocks, E1B, E3, and E4 to overcome the effect of apoptosis of infected permissive cells. One of the proteins coded by the E1B region, the 19K protein confers a survival fiction in adenovirus-infected cells and prevents premature cell death. Adenovirus mutants defective in the 19K gene produced large clear plaques on infected cell monolayers. Several of these mutants induce an enhanced cytopathic effect in infected cells resulting in cellular destruction as well as fragmentation of cellular and viral DNA. The DNA fragmentation induced by 19K mutants is reminiscent of that observed during apoptosis. Although it has not yet been determined whether DNA fragmentation induced by 19K mutants occurs by an apoptotic mechanism, it is clear that the 19 kDa protein protects against a cell death program induced by viral infection, thus facilitating efficient virus replication. In addition, the 19 kDa protein suppresses the cytotoxic effects of certain external stimuli such as the tumor necrosis factor α and anti-Fas antibody. Both of these agents cause cell death through apoptosis. Similarly, the 19 kDa protein protects cells against the effects of DNA-damaging agents such as the anti-cancer drug cisplatin and ultraviolet radiation induced cell death through a p53-dependent apoptotic pathway. Cells expressing the 19 kDa protein efficiently suppress cell death induced by overexpression of p53. Thus, the 19 kDa protein provides a survival function in virus-infected cells and also protects cells against certain other death-inducing stimuli.

The survival function provided by E1B 19K is similar to the activity of the cellular protooncogene Bcl-2. The Bcl-2 oncogene was isolated from a follicular lymphoma and has been shown to enhance the survival of hematopoietic B and T cells by blocking apoptosis. In addition, overexpression of Bcl-2 protein inhibits apoptosis induced by exposure to diverse stimuli possibly through different pathways. Although the effect of 19 kDa protein expression on cell death induced by diverse stimuli has not been extensively examined, the Bcl-2 protein can clearly substitute for the 19 kDa protein during adenovirus infection. Characteristic fragmentation of cellular DNA induced by infection with adenovirus type 2 (Ad2) 19K mutants is efficiently suppressed in cells ectopically expressing the human Bcl-2 protein. Similarly, expression of Bcl-2 by an Ad2-Bcl-2 recombinant virus (Ad-Bcl2) can fully substitute for the 19K function. The Ad-Bcl12 virus does not induce DNA fragmentation in infected cells and forms small plaques on cell monolayers. Rao et al. (1992) *Proc. Natl. Acad. Sci.* U.S.A. 89:7742–46 have reported that Bcl-2 can substitute for 19K in transformation of primary rat kidney cells in cooperation with E1A. Although these results do not clarify whether the 19 kDa and Bcl-2 proteins function by similar mechanisms, they indicate that these two proteins can provide cell survival function against certain stimuli.

The mechanism by which the 19K gene and the Bcl-2 protooncogene protect against cell death is not known. These proteins may mediate cell survival by interacting with certain cellular proteins. Boyd J. M. et al. (1994) *Cell* 79:341–351, have identified three proteins, NIP1, NIP2, and NIP3, which interact with both the adenovirus E1B 19 kDa protein and the Bcl-2 protein. The NIP1, NIP2, and NIP3 proteins are believed to play a role in the ability of the E1B 19 kDa protein to provide a cell survival function.

SUMMARY OF THE INVENTION

The present invention is based, at least in part, on the discovery of novel NIP2 family members, referred to herein as "NIP2b, NIP2cL, and NIP2cS" nucleic acid and protein molecules. The NIP2b, NIP2cL, and NIP2cS molecules of the present invention are useful as modulating agents for regulating a variety of cellular processes. Accordingly, in one aspect, this invention provides isolated nucleic acid molecules encoding NIP2b, NIP2cL, and NIP2cS proteins or biologically active portions thereof, as well as nucleic acid fragments suitable as primers or hybridization probes for the detection of NIP2b, NIP2cL, and NIP2cS-encoding nucleic acids.

In one embodiment, a NIP2b, NIP2cL, or NIP2cS nucleic acid molecule of the invention is at least 59%, 60%, 65%, 70%, 75%, 80%, 85%, 90%, 95%, 98%, or more identical to the nucleotide sequence (e.g., to the entire length of the nucleotide sequence) shown in SEQ ID NO:1, 3, 4, 6, 7, or 9, or a complement thereof.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1–369 of SEQ ID NO: 1. In another embodiment, the nucleic acid molecule includes SEQ ID NO:3 and nucleotides 1483–3076 of SEQ ID NO:1. In another preferred embodiment, the nucleic acid molecule consists of the nucleotide sequence shown in SEQ ID NO:1 or 3. In another preferred embodiment, the nucleic acid molecule includes a fragment of at least 535 nucleotides (e.g., 535 contiguous nucleotides) of the nucleotide sequence of SEQ ID NO:1 or 3, or a complement thereof.

In another preferred embodiment, the isolated nucleic acid molecule includes the nucleotide sequence shown SEQ ID NO:4 or 6, or a complement thereof. In another embodiment, the nucleic acid molecule includes SEQ ID NO:6 and nucleotides 1–22 of SEQ ID NO:4. In another embodiment, the nucleic acid molecule includes SEQ ID NO:6 and nucleotides 989–4235 of SEQ ID NO:4. In another preferred embodiment, the nucleic acid molecule consists of the nucleotide sequence shown in SEQ ID NO:4 or 6. In another preferred embodiment, the nucleic acid molecule includes a fragment of at least 3225 nucleotides (e.g., 3225 contiguous nucleotides) of the nucleotide sequence of SEQ ID NO:4, SEQ ID NO:6, or a complement thereof.

In a preferred embodiment, the isolated nucleic acid molecule includes the nucleotide sequence shown SEQ ID NO:7 or 9, or a complement thereof. In another embodiment, the nucleic acid molecule includes SEQ ID NO:9 and nucleotides 1–55 of SEQ ID NO:7. In another embodiment, the nucleic acid molecule includes SEQ ID NO:9 and nucleotides 434–2966 of SEQ ID NO:7. In another preferred embodiment, the nucleic acid molecule consists of the nucleotide sequence shown in SEQ ID NO:7 or 9. In another preferred embodiment, the nucleic acid molecule includes a fragment of at least 461 nucleotides (e.g., 461 contiguous nucleotides) of the nucleotide sequence of SEQ ID NO:7, SEQ ID NO:9, or a complement thereof.

In another embodiment, a NIP2b, NIP2cL, and NIP2cS nucleic acid molecule includes a nucleotide sequence encoding a protein having an amino acid sequence sufficiently homologous to the amino acid sequence of SEQ ID NO:2, 5, or 8. In a preferred embodiment, a NIP2b, NIP2cL, and NIP2cS nucleic acid molecule includes a nucleotide sequence encoding a protein having an amino acid sequence at least 60%, 65%, 70%, 75%, 80%, 85%, 90%, 95%, 98% or more homologous to the entire length of the amino acid sequence of SEQ ID NO:2, 5, or 8.

In another preferred embodiment, an isolated nucleic acid molecule encodes the amino acid sequence of human NIP2b, NIP2cL, and NIP2cS. In yet another preferred embodiment, the nucleic acid molecule includes a nucleotide sequence encoding a protein having the amino acid sequence of SEQ ID NO:2, 5, or 8. In yet another preferred embodiment, the nucleic acid molecule is at least 461, 535, or 3225 nucleotides in length. In a further preferred embodiment, the nucleic acid molecule is at least 461, 535, or 3225 nucleotides in length and encodes a protein having a NIP2b, NIP2cL, and NIP2cS activity (as described herein).

Another embodiment of the invention features nucleic acid molecules, preferably NIP2b, NIP2cL, and NIP2cS nucleic acid molecules, which specifically detect NIP2b, NIP2cL, and NIP2cS nucleic acid molecules relative to nucleic acid molecules encoding non-NIP2b, non-NIP2cL, and non-NIP2cS proteins. For example, in one embodiment, such a nucleic acid molecule is at least 300–350, 350–400, 400–450, 461, 461–500, 535, 535–600 or more nucleotides in length and hybridizes under stringent conditions to a nucleic acid molecule comprising the nucleotide sequence shown in SEQ ID NO:1, 4, or 7, or a complement thereof.

In preferred embodiments, the nucleic acid molecules are at least 15 (e.g., contiguous) nucleotides in length and hybridize under stringent conditions to nucleotides 1–348, 431–478, 676–784, 1538–1546, 1587–1598, 1615–1727, or 2070–3076 of SEQ ID NO:1. In other preferred embodiments, the nucleic acid molecules comprise nucleotides 1–348, 431–478, 676–784, 1538–1546, 1587–1598, 1615–1727, or 2070–3076 of SEQ ID NO:1.

In other preferred embodiments, the nucleic acid molecules are at least 15 (e.g., contiguous) nucleotides in length and hybridize under stringent conditions to nucleotides 1–16 of SEQ ID NO:4. In other preferred embodiments, the nucleic acid molecules comprise nucleotides 1–16 of SEQ ID NO:4.

In yet other preferred embodiments, the nucleic acid molecules are at least 15 (e.g., contiguous) nucleotides in length and hybridize under stringent conditions to nucleotides 1–26, 406–598, 1058–2703, 2775–2936, or 2956–2966 of SEQ ID NO:7. In other preferred embodiments, the nucleic acid molecules comprise nucleotides 1–26, 406–598, 1058–2703, 2775–2936, or 2956–2966 of SEQ ID NO:7.

In other preferred embodiments, the nucleic acid molecule encodes a naturally occurring allelic variant of a polypeptide comprising the amino acid sequence of SEQ ID NO:2, 5, or 8, wherein the nucleic acid molecule hybridizes to a nucleic acid molecule comprising SEQ ID NO:1, 3, 4, 6, 7, or 9 under stringent conditions.

Another embodiment of the invention provides an isolated nucleic acid molecule which is antisense to a NIP2b, NIP2cL, and NIP2cS nucleic acid molecule, e.g., the coding strand of a NIP2b, NIP2cL, and NIP2cS nucleic acid molecule.

Another aspect of the invention provides a vector comprising a NIP2b, a NIP2cL, or a NIP2cS nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a NIP2b, NIP2cL, and NIP2cS protein, by culturing in a suitable medium, a host cell, e.g., a mammalian host cell such as a non-human mammalian cell, of the invention containing a recombinant expression vector, such that the protein is produced.

Another aspect of this invention features isolated or recombinant NIP2b, NIP2cL, and NIP2cS proteins and polypeptides. In one embodiment, the isolated protein, preferably a NIP2b, NIP2cL, or NIP2cS protein, includes at least one transmembrane domain. In a preferred embodiments, the isolated protein, preferably a NIP2b, NIP2cL, or NIP2cS protein, includes at least one calcium binding domain. In yet another preferred embodiment, the isolated protein, preferably a NIP2b, NIP2cL, or NIP2cS protein, includes at least one "4 transmembrane segment integral membrane protein domain". In a preferred embodiment, the protein, preferably a NIP2b, NIP2cL, or NIP2cS protein, includes at least one transmembrane domain and has an amino acid sequence at least about 60%, 65%, 70%, 75%, 80%, 85%, 90%, 95%, 98% or more homologous to the amino acid sequence of SEQ ID NO:2, 5, or 8. In another embodiment, the protein, preferably a NIP2b, NIP2cL, or NIP2cS protein, includes at least one calcium-binding domain and has an amino acid sequence at least about 60%, 65%, 70%, 75%, 80%, 85%, 90%, 95%, 98% or more homologous to the amino acid sequence of SEQ ID NO:2, 5, or 8. In yet another preferred embodiment, the protein, preferably a NIP2b, NIP2cL, or NIP2cS protein, includes at least one "4 transmembrane segment integral membrane protein domain" and has an amino acid sequence at least about 60%, 65%, 70%, 75%, 80%, 85%, 90%, 95%, 98% or more homologous to the amino acid sequence of SEQ ID NO:2, 5, or 8. In another preferred embodiment, the protein, preferably a NIP2b, NIP2cL, or NIP2cS protein, includes at least one transmembrane domain and plays a role in apoptosis or programmed cell death. In another embodiment, the protein, preferably a NIP2b, NIP2cL, or NIP2cS protein, includes at least one calcium-binding domain and plays a role in apoptosis or programmed cell death. In yet another preferred embodiment, the protein, preferably a NIP2b, NIP2cL, or NIP2cS protein, includes at least one "4 transmembrane segment integral membrane protein domain" and plays a role in apoptosis or programmed cell death. In yet another preferred embodiment, the protein, preferably a NIP2b, NIP2cL, and NIP2cS protein, includes at least one transmembrane domain and is encoded by a nucleic acid molecule having a nucleotide sequence which hybridizes under stringent hybridization conditions to a nucleic acid molecule comprising the nucleotide sequence of SEQ ID NO:1, 3, 4, 6, 7, or 9. In another embodiment, the protein, preferably a NIP2b, NIP2cl, or NIP2cS protein, includes at least one calcium-binding domain and is encoded by a nucleic acid molecule having a nucleotide sequence which hybridizes under stringent hybridization conditions to a nucleic acid molecule comprising the nucleotide sequence of SEQ ID NO:1, 3, 4, 6, 7, or 9. In yet another embodiment, the protein, preferably a NIP2b, NIP2cL, or NIP2cS protein, includes at least one "4 transmembrane segment integral membrane protein domain" and is encoded by a nucleic acid molecule having a nucleotide sequence which hybridizes under stringent hybridization conditions to a nucleic acid molecule comprising the nucleotide sequence of SEQ ID NO:1, 3, 4, 6, 7, or 9.

In another embodiment, the invention features fragments of the protein having the amino acid sequence of SEQ ID NO:2, 5, or 8, wherein the fragment comprises at least 15 amino acids (e.g., contiguous amino acids) of the amino acid sequence of SEQ ID NO:2, 5, or 8. In another embodiment, the protein, preferably a NIP2b, NIP2cL, or NIP2cS protein, has the amino acid sequence of SEQ ID NO:2, 5, or 8, respectively.

In another embodiment, the invention features an isolated protein, preferably a NIP2b, NIP2cL, and NIP2cS protein, which is encoded by a nucleic acid molecule consisting of a nucleotide sequence at least about 59%, 60%, 65%, 70%, 75%, 80%, 85%, 90%, 95%, 98% or more homologous to a nucleotide sequence of SEQ ID NO:1, 3, 4, 6, 7, or 9, or a complement thereof. This invention further features an isolated protein, preferably a NIP2b, NIP2cL, or NIP2cS protein, which is encoded by a nucleic acid molecule consisting of a nucleotide sequence which hybridizes under stringent hybridization conditions to a nucleic acid molecule comprising the nucleotide sequence of SEQ ID NO:1, 3, 4, 6, 7, or 9, or a complement thereof.

The proteins of the present invention or portions thereof, e.g., biologically active portions thereof, can be operatively linked to a non-NIP2b, non-NIP2cL, or non-NIP2cS polypeptide (e.g., heterologous amino acid sequences) to form fusion proteins. The invention further features antibodies, such as monoclonal or polyclonal antibodies, that specifically bind proteins of the invention, preferably NIP2b, NIP2cL, and NIP2cS proteins. In addition, the NIP2b, NIP2cL, and NIP2cS proteins or biologically active portions thereof can be incorporated into pharmaceutical compositions, which optionally include pharmaceutically acceptable carriers.

In another aspect, the present invention provides a method for detecting the presence of a NIP2b, NIP2cL, and NIP2cS nucleic acid molecule, protein or polypeptide in a biological sample by contacting the biological sample with an agent capable of detecting a NIP2b, NIP2cL, and NIP2cS nucleic acid molecule, protein or polypeptide such that the presence of a NIP2b, NIP2cL, and NIP2cS nucleic acid molecule, protein or polypeptide is detected in the biological sample.

In another aspect, the present invention provides a method for detecting the presence of NIP2b, NIP2cL, and NIP2cS activity in a biological sample by contacting the biological sample with an agent capable of detecting an indicator of NIP2b, NIP2cL, and NIP2cS activity such that the presence of NIP2b, NIP2cL, and NIP2cS activity is detected in the biological sample.

In another aspect, the invention provides a method for modulating NIP2b, NIP2cL, and NIP2cS activity comprising contacting a cell capable of expressing NIP2b, NIP2cL, and NIP2cS with an agent that modulates NIP2b, NIP2cL, and NIP2cS activity such that NIP2b, NIP2cL, and NIP2cS activity in the cell is modulated. In one embodiment, the agent inhibits NIP2b, NIP2cL, and NIP2cS activity. In another embodiment, the agent stimulates NIP2b, NIP2cL, and NIP2cS activity. In one embodiment, the agent is an antibody that specifically binds to a NIP2b, NIP2cL, and NIP2cS protein. In another embodiment, the agent modulates expression of NIP2b, NIP2cL, and NIP2cS by modulating transcription of a NIP2b, NIP2cL, and NIP2cS gene or translation of a NIP2b, NIP2cL, and NIP2cS mRNA. In yet another embodiment, the agent is a nucleic acid molecule having a nucleotide sequence that is antisense to the coding strand of a NIP2b, NIP2cL, and NIP2cS mRNA or a NIP2b, NIP2cL, and NIP2cS gene.

In one embodiment, the methods of the present invention are used to treat a subject having a disorder characterized by aberrant NIP2b, NIP2cL, and NIP2cS protein or nucleic acid expression or activity by administering an agent which is a NIP2b, NIP2cL, and NIP2cS modulator to the subject. In one embodiment, the NIP2b, NIP2cL, and NIP2cS modulator is a NIP2b, NIP2cL, and NIP2cS protein. In another embodiment the NIP2b, NIP2cL, and NIP2cS modulator is a NIP2b, NIP2cL, and NIP2cS nucleic acid molecule. In yet another embodiment, the NIP2b, NIP2cL, and NIP2cS modulator is a peptide, peptidomimetic, or other small molecule. In a preferred embodiment, the disorder characterized by aberrant NIP2b, NIP2cL, and NIP2cS protein or nucleic acid expression is a disorder characterized by deregulated programmed cell death.

The present invention also provides a diagnostic assay for identifying the presence or absence of a genetic alteration characterized by at least one of (i) aberrant modification or mutation of a gene encoding a NIP2b, NIP2cL, and NIP2cS protein; (ii) mis-regulation of the gene; and (iii) aberrant post-translational modification of a NIP2b, NIP2cL, and NIP2cS protein, wherein a wild-type form of the gene encodes a protein with a NIP2b, NIP2cL, and NIP2cS activity.

In another aspect the invention provides a method for identifying a compound that binds to or modulates the activity of a NIP2b, NIP2cL, and NIP2cS protein, by providing an indicator composition comprising a NIP2b, NIP2cL, and NIP2cS protein having NIP2b, NIP2cL, and NIP2cS activity, contacting the indicator composition with a test compound, and determining the effect of the test compound on NIP2b, NIP2cL, and NIP2cS activity in the indicator composition to identify a compound that modulates the activity of a NIP2b, NIP2cL, and NIP2cS protein.88

Other features and advantages of the invention will be apparent from the following detailed description and claims.

BRIEF DESCRIPTION OF THE DRAWINGS

FIG. 1 depicts the cDNA sequence and predicted amino acid sequence of human NIP2b. The nucleotide sequence corresponds to nucleic acids 1 to 3076 of SEQ ID NO:1. The amino acid sequence corresponds to amino acids 1 to 371 of SEQ ID NO:2. The coding region without the 5' and 3' untranslated regions of the human NIP2b gene is shown in SEQ ID NO:3.

FIG. 3 depicts the cDNA sequence and predicted amino acid sequence of human NIP2cS. The nucleotide sequence corresponds to nucleic acids 1 to 2966 of SEQ ID NO:7. The amino acid sequence corresponds to amino acids 1 to 126 of SEQ ID NO:8. The coding region without the 5' and 3' untranslated regions of the human NIP2cS gene is shown in SEQ ID NO:9.

FIG. 5 depicts a structural, hydrophobicity, and antigenicity analysis of the human NIP2cL protein.

FIG. 7 depicts the results of a search which was performed against the HMM database and which resulted in the identification of a "4 transmembrane segments integral membrane proteins" domain in the human NIP2b protein.

FIG. 8 depicts the results of a search which was performed against the HMM database and which resulted in the identification of a calreticulin calcium-binding domain in the human NIP2cL protein.

FIG. 9 depicts the results of a search which was performed against the HMM database and which resulted in the identification of a calreticulin calcium-binding domain in the human NIP2cS protein.

FIG. 10 depicts an alignment of the NIP2b protein with the human Bcl-2/adenovirus E1B 19 kDa-interacting protein 2 (BNIP-2, Accession Number U15173) using the GAP program in the GCG software package (Blossom 62 matrix) and a gap weight of 12 and a length weight of 4.

FIG. 11 depicts an alignment of the NIP2b protein with the NIP2cL protein using the GAP program in the GCG software package (Blossom 62 matrix) and a gap weight of 12 and a length weight of 4.

FIG. 12 depicts an alignment of the NIP2cL protein with the human Bcl-2/adenovirus E1B 19 kDa-interacting protein 2 (BNIP-2, Accession Number U15173) using the GAP program in the GCG software package (Blossom 62 matrix) and a gap weight of 12 and a length weight of 4.

DETAILED DESCRIPTION OF THE INVENTION

Figure 2:
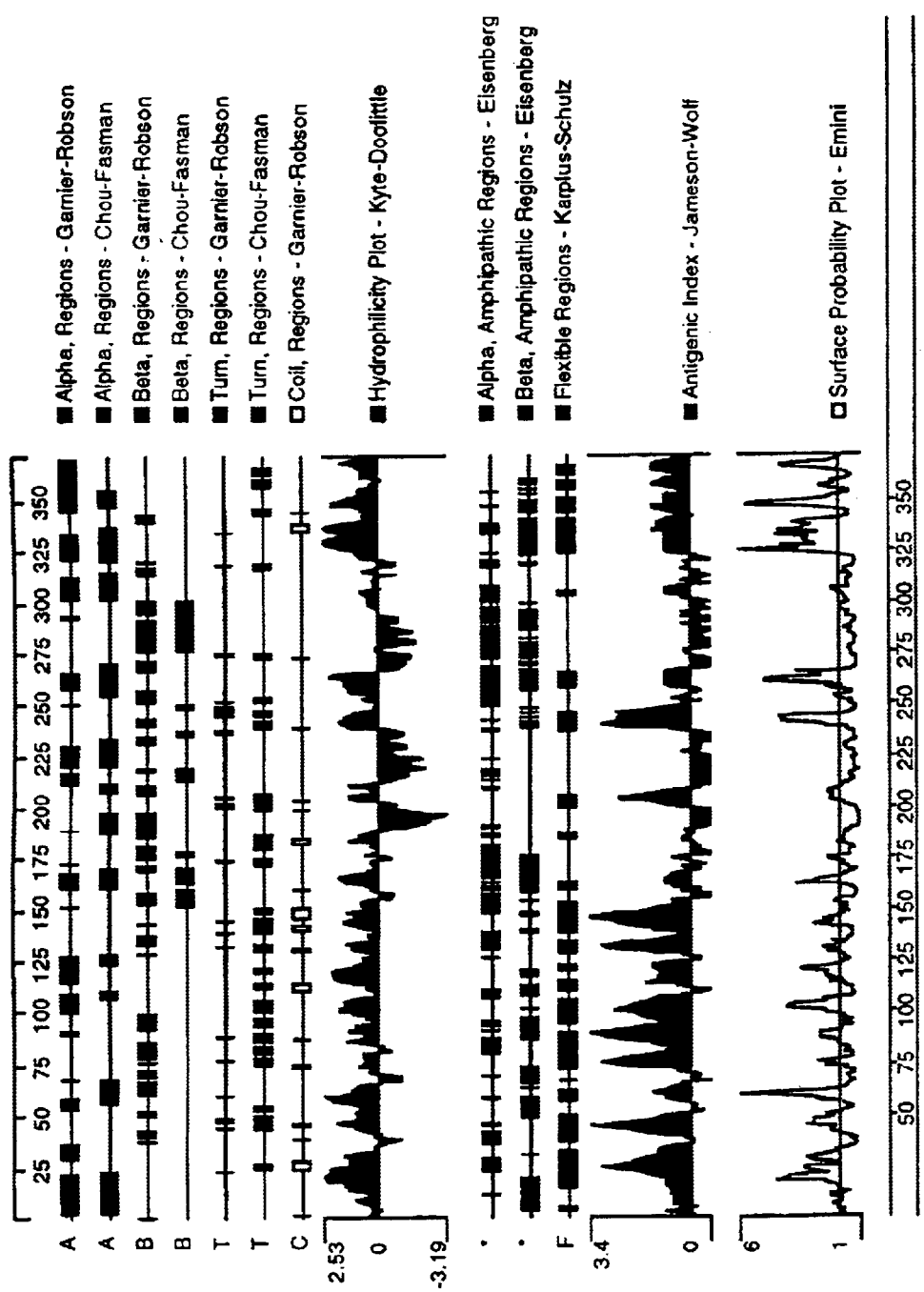
FIG. 2 depicts the cDNA sequence and predicted amino acid sequence of human NIP2cL. The nucleotide sequence corresponds to nucleic acids 1 to 4235 of SEQ ID NO:4. The amino acid sequence corresponds to amino acids 1 to 322 of SEQ ID NO:5. The coding region without the 5' and 3' untranslated regions of the human NIP2cL gene is shown in SEQ ID NO:6.

The present invention is based, at least in part, on the discovery of novel NIP2 family members, referred to herein as "NIP2b, NIP2cL, and NIP2cS" nucleic acid and protein molecules. These molecules comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of NIP2b, NIP2cL, and NIP2cS proteins comprise a "transmembrane domain." As used herein, the term "transmembrane domain" includes an amino acid sequence of about 15 amino acid residues in length which spans the plasma membrane. More preferably, a transmembrane domain includes about at least 20, 25, 30, 35, 40, or 45 and spans the plasma membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neuronsci*. 19. 235–63, the contents of which are incorporated herein by reference. Amino acid residues 183–199 of the human NIP2b and amino acid residues 174–190 of the human NIP2cL comprise transmembrane domains.

In another embodiment, a NIP2b, NIP2cL, and NIP2cS of the present invention is identified based on the presence of a "calcium-binding domain" in the protein or corresponding nucleic acid molecule. As used herein, the term "calcium-binding domain" includes a protein domain having an amino acid sequence of about 110 amino acids which has the capacity to bind calcium. Preferably, a calcium binding domain includes a protein domain which is at least 50, 60, 70, 80, 90, or 100 amino acid residues in length and which has the capacity to bind calcium. The calcium-binding domain HMM has been assigned the PFAM Accession MILPAT0063 (Sonnhammer, et al (1997) *Proteins* 28:405–20).

To identify the presence of a calcium-binding domain in a NIP2b, NIP2cL, or NIP2cS protein, and make the determination that a protein of interest has a particular profile, the amino acid sequence of the protein is searched against a database of HMMs (e.g., the Pfam database, release 2.1) using the default parameters (Sonnhammer, et al (1997) *Proteins* 28:405–420). For example, the hmmsf program, which is available as pat of the HMMER package of search programs, is a family specific default program for MILPAT0063 and a score of 15 is the default threshold score for determining a hit. Alternatively, the threshold score for determining a hit can be lowered (e.g, to 8 bits). A description of the Pfam database can be found in Sonhammer et al. (1997) *Proteins* 28(3)405–420 and a detailed description of HMMs can be found, for example, in Gribskov et al. (1990) *Meth. Enzymol*. 183:146–159; Gribskov et al. (1987) *Proc Natl. Acad Sci USA* 84:4355–4358; Krogh et al. (1994) *J. Mol Biol*. 235:1501–1531; and Stultz et al. (1993) *Protein Sci*. 2:305–314, the contents of which are incorporated herein by reference. A search was performed against the HMM database resulting in the identification of a calcium-binding domain in the amino acid sequence of NIP2cL (SEQ ID NO: 5) at about residues 55–160 (SEQ ID NO:5 and NIP2cS (SEQ ID NO:8) at about residues 59–96 of SEQ ID NO:8. The results of the searches are set forth in FIGS. 8 and 9, respectively.

Accordingly, NIP2b, NIP2cL, and NIP2cS proteins having at least 50–60% homology, preferably about 60–70%, more preferably about 70–80%, or about 80–90% homology with a calcium binding domain of human NIP2cL and NIP2cS are within the scope of the invention.

In another embodiment a NIP2b, NIP2cL, and NIP2cS of the present invention is identified based on the presence of a "4 transmembrane segment integral membrane protein domain" in the protein or corresponding nucleic acid molecule. As used herein, the term "4 transmembrane segment integral membrane protein domain" includes a protein domain having an amino acid sequence of about 50 amino acid residues and having a bit score for the alignment of the sequence to the "4 transmembrane segment integral membrane protein domain" (HMM) of at least 1 or greater. Preferably the term "4 transmembrane segment integral membrane protein domain" includes a protein domain having an amino acid sequence of about 60, 70, 80, or 90 amino acids and having a bit score for the alignment of the sequence to the "4 transmembrane segment integral membrane protein domain" (HMM) of at least 2, preferably 3–10, more preferably 10–30, more preferably 30–50, even more preferably 50–75, 75–100, 100–200 or greater. The "4 transmembrane segment integral membrane protein domain" HMM has been assigned the PFAM Accession PF00335 (Sonnhammer, et al. (1997) *Proteins* 28:405–420). A search was performed against the HMM database, as described herein, resulting in the identification of a "4 transmembrane segment integral membrane protein domain" in the amino acid sequence of NIP2b (SEQ ID NO:2) at about residues 253 to 293. The results of the search are set forth in FIG. 7.

Accordingly, NIP2b, NIP2cL, and NIP2cS proteins having at least 50–60% homology, preferably about 60–70%, more preferably about 70–80%, or about 80–90% homology with a "4 transmembrane segment integral membrane protein domain" of human NIP2b, are within the scope of the invention.

The NIP2b, NIP2cL, and NIP2cS proteins of the present invention are believed to play a role in apoptosis or programmed cell death. As used herein, "programmed cell death" or "apoptosis" includes a genetically regulated process involved in the normal development of multicellular organisms. This process occurs in cells destined for removal in a variety of normal situations, including larval development of the nematode *c. elegans*, insect metamorphosis, development in mammalian embryos including the nephrogenic zone in the developing kidney, and regression or atrophy (e.g., in the prostrate after castration). Programmed cell death can occur following the withdrawal of growth and trophic factors in many cells, nutritional deprivation, hormone treatment, ultraviolet irradiation, and exposure to toxic and infectious agents including reactive oxygen species and phosphatase inhibitors, e.g., okadaic acid, calcium ionphones, and a number of cancer chemotherapeutic agents. For a detailed description of programmed cell death see Trump B. F. et al. (1995) *FASEB J.* 9: 219–228 and Lee S. (1993) *Curr. Opin. Cell Biol.* 5: 286–291, the contents of which are incorporated herein by reference. Thus, the NIP2b, NIP2cL, and NIP2cS proteins by participating in a programmed cell death pathway, can modulate a programmed cell death pathway activity and provide novel diagnostic targets and therapeutic agents for disorders characterized by deregulated programmed cell death, particularly in cells that express NIP2b, NIP2cL, and NIP2cS, e.g., neuronal cells.

As used herein, a "disorder characterized by deregulated programmed cell death" refers to a disorder, disease or condition which is characterized by a deregulation, e.g., an upregulation or a downregulation, of programmed cell death. Programmed cell death deregulation can lead to deregulation of cellular proliferation and/or cell cycle progression. Examples of disorders characterized by deregulated programmed cell death include neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, Jakob-Creutzfieldt disease, or AIDS related dementias; ischemic injury, e.g., myocardial infarction, stroke, or reperfusion injury; or profilerative disorders, e.g., cancer.

Isolated proteins of the present invention, preferably NIP2b, NIP2cL, and NIP2cS proteins, have an amino acid sequence sufficiently homologous to the amino acid sequence of SEQ ID NO:2, 5, or 8 or are encoded by a nucleotide sequence sufficiently homologous to SEQ ID NO:1, 3, 4, 6, 7, or 9. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein, an "NIP2b, NIP2cL, and NIP2cS activity", "biological activity of NIP2b, NIP2cL, and NIP2cS" or "functional activity of NIP2b, NIP2cL, and NIP2cS", refers to an activity exerted by a NIP2b, NIP2cL, and NIP2cS protein, polypeptide or nucleic acid molecule on a NIP2b, NIP2cL, and NIP2cS responsive cell or on a NIP2b, NIP2cL, and NIP2cS protein substrate, as determined in vivo, or in vitro, according to standard techniques. In one embodiment, a NIP2b, NIP2cL, and NIP2cS activity is a direct activity, such as an association with a NIP2b, NIP2cL, and NIP2cS-target molecule. As used herein, a "target molecule" or "binding partner" is a molecule with which a NIP2b, NIP2cL, and NIP2cS protein binds or interacts in nature, such that NIP2b, NIP2cL, and NIP2cS-mediated function is achieved. An NIP2b, NIP2cL, and NIP2cS target molecule can be a non-NIP2b, non-NIP2cL, and non-NIP2cS molecule or a NIP2b, NIP2cL, and NIP2cS protein or polypeptide of the present invention. In an exemplary embodiment, a NIP2b, NIP2cL, and NIP2cS target molecule is a NIP2b, NIP2cL, and NIP2cS ligand. Alternatively, a NIP2b, NIP2cL, and NIP2cS activity is an indirect activity, such as a cellular signaling activity mediated by interaction of the NIP2b, NIP2cL, and NIP2cS protein with a NIP2b, NIP2cL, and NIP2cS ligand.

Accordingly, another embodiment of the invention features isolated NIP2b, NIP2cL, and NIP2cS proteins and polypeptides having a NIP2b, NIP2cL, and NIP2cS activity. Preferred proteins are NIP2b, NIP2cL, and NIP2cS proteins having at least one transmembrane domain and, preferably, a NIP2b, NIP2cL, and NIP2cS activity. Other preferred proteins are NIP2b, NIP2cL, and NIP2cS proteins having at least one calcium-binding domain and, preferably, a NIP2b, NIP2cL, and NIP2cS activity. Other preferred proteins are NIP2b, NIP2cL, and NIP2cS proteins having at least one "4 transmembrane segment integral membrane protein domain" and, preferably, a NIP2b, NIP2cL, and NIP2cS activity. Additional preferred proteins have at least one transmembrane domain and/or at least one calcium-binding domain, and/or at least one "4 transmembrane segment integral membrane protein domain", and are, preferably, encoded by a nucleic acid molecule having a nucleotide sequence which hybridizes under stringent hybridization conditions to a nucleic acid molecule comprising the nucleotide sequence of SEQ ID NO:1, 3, 4, 6, 7, or 9.

The nucleotide sequence of the isolated human NIP2b cDNA and the predicted amino acid sequence of the human NIP2b polypeptide are shown in FIG. 1 and in SEQ ID NOs:1 and 2 respectively.

The human NIP2b gene, which is approximately 3076 nucleotides in length, encodes a protein having a molecular weight of approximately 42.7 kD and which is approximately 371 amino acid residues in length. A 5 kb NIP2b transcript is predominantly expressed in the brain, but on longer exposures this transcript can also be detected in prostate and small intestine. An additional 4 kb transcript can also be detected in the heart and skeletal muscle on longer exposures. Within the brain, NIP2b is expressed in most regions. The following areas give a particularly strong signal: cortex, amygdala, striatum, hippocampus, substantia nigra, corpus callosum, cerebellum (Purkinje cells), striatum, basal forebrain, lateral eniculate nucleus, and facial nucleus (motor neurons).

The nucleotide sequence of the isolated human NIP2cL cDNA and the predicted amino acid sequence of the human NIP2cL polypeptide are shown in FIG. 2 and in SEQ ID NOs:4 and 5, respectively.

The human NIP2cL gene, which is approximately 4235 nucleotides in length, encodes a protein having a molecular weight of approximately 37 kD and which is approximately 322 amino acid residues in length. The NIP2cL transcript is predominantly expressed in the brain, but can also be detected in the prostate, colon and small intestine. On longer exposures, this transcript can also be detected in the heart, placenta, kidney, pancreas, spleen, testes, ovary and skeletal muscle. In addition, numerous other small transcripts can be seen on longer exposures. Within the brain, NIP2cL is expressed in the following regions: cortex, amygdala, cerebellum (granule cells), hippocampus (dentate gyrus and hippocampal pyramidal cells), striatum, thalamus, locus coeruleus, lateral geniculate nucleus, and facial nucleus (motor neurons).

The nucleotide sequence of the isolated human NIP2cS cDNA and the predicted amino acid sequence of the human NIP2cS polypeptide are shown in FIG. 3 and in SEQ ID NOs:7 and 8, respectively.

The human NIP2cS gene, which is approximately 2966 nucleotides in length, encodes a protein having a molecular weight of approximately 14.5 kD and which is approximately 126 amino acid residues in length. The NIP2cS transcript is predominantly expressed in the heart, skeletal muscle, and brain.

Various aspects of the invention are described in further detail in the following subsections:

I. Isolated Nucleic Acid Molecules

One aspect of the invention pertains to isolated nucleic acid molecules that encode NIP2b, NIP2cL, and NIP2cS proteins or biologically active portions thereof, as well as nucleic acid fragments sufficient for use as hybridization probes to identify NIP2b, NIP2cL, and NIP2cS-encoding nucleic acid molecules (e.g., NIP2b, NIP2cL, and NIP2cS mRNA) and fragments for use as PCR primers for the amplification or mutation of NIP2b, NIP2cL, and NIP2cS nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NIP2b, NIP2cL, and NIP2cS nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, 6, 7, or 9, or a portion thereof, can be isolated using standard molecular biology techniques and the sequence information provided herein. Using all or portion of the nucleic acid sequence of SEQ ID NO:1, 3, 4, 6, 7, or 9, as a hybridization probe, NIP2b, NIP2cL, and NIP2cS nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, 3, 4, 6, 7, or 9, can be isolated by the polymerase chain reaction (PCR) using synthetic oligonucleotide primers designed based upon the sequence of SEQ ID NO:1, 3, 4, 6, 7, or 9.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NIP2b, NIP2cL, and NIP2cS nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human NIP2b cDNA. This cDNA comprises sequences encoding the human NIP2b protein (i.e., "the coding region", from nucleotides 370–1482), as well as 5' untranslated sequences (nucleotides 1–369) and 3' untranslated sequences (nucleotides 1483–3076). Alternatively, the nucleic acid molecule can comprise only the coding region of SEQ ID NO:1 (e.g., nucleotides 370–1482, corresponding to SEQ ID NO:3).

In a preferred embodiment, an isolated nucleic acid molecule of the invention comprises the nucleotide sequence shown in SEQ ID NO:4. The sequence of SEQ ID NO:4 corresponds to the human NIP2cL cDNA. This cDNA comprises sequences encoding the human NIP2cL protein (i.e., "the coding region", from nucleotides 23–988), as well as 5' untranslated sequences (nucleotides 1–22) and 3' untranslated sequences (nucleotides 989–4235). Alternatively, the nucleic acid molecule can comprise only the coding region of SEQ ID NO:4 (e.g., nucleotides 23–988, corresponding to SEQ ID NO:6).

In a preferred embodiment, an isolated nucleic acid molecule of the invention comprises the nucleotide sequence shown in SEQ ID NO:7. The sequence of SEQ ID NO:7 corresponds to the human NIP2cS cDNA. This cDNA comprises sequences encoding the human NIP2cS protein (i.e., "the coding region", from nucleotides 56–433), as well as 5' untranslated sequences (nucleotides 1–55) and 3' untranslated sequences (nucleotides 434–2966). Alternatively, the nucleic acid molecule can comprise only the coding region of SEQ ID NO:7 (e.g., nucleotides 56–433, corresponding to SEQ ID NO:9).

In another preferred embodiment, an isolated nucleic acid molecule of the invention comprises a nucleic acid molecule which is a complement of the nucleotide sequence shown in SEQ ID NO:1, 3, 4, 6, 7, or 9, or a portion of any of these nucleotide sequences. A nucleic acid molecule which is complementary to the nucleotide sequence shown in SEQ ID NO:1, 3, 4, 6, 7, or 9, is one which is sufficiently complementary to the nucleotide sequence shown in SEQ ID NO:1, 3, 4, 6, 7, or 9, such that it can hybridize to the nucleotide sequence shown in SEQ ID NO:1, 3, 4, 6, 7, or 9, thereby forming a stable duplex.

In still another preferred embodiment, an isolated nucleic acid molecule of the present invention comprises a nucleotide sequence which is at least about 59%, 60%, 65%, 70%, 75%, 80%, 85%, 90%, 95%, 98% or more homologous to the entire length of the nucleotide sequence shown in SEQ ID NO:1, 3, 4, 6, 7, or 9, or a portion of any of these nucleotide sequences.

Moreover, the nucleic acid molecule of the invention can comprise only a portion of the nucleic acid sequence of SEQ ID NO:1, 3, 4, 6, 7, or 9, for example fragment which can be used as a probe or primer or a fragment encoding a portion of a NIP2b, NIP2cL, and NIP2cS protein, e.g., a biologically active portion of a NIP2b, NIP2cL, and NIP2cS protein. The nucleotide sequence determined from the cloning of the NIP2b, NIP2cL, and NIP2cS gene allows for the generation of probes and primers designed for use in identifying and/or cloning other NIP2b, NIP2cL, and NIP2cS family members, as well as NIP2b, NIP2cL, and NIP2cS homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 4, 6, 7, or 9, of an anti-sense sequence of SEQ ID NO:1, 3, 4, 6, 7, or 9, or of a naturally occurring allelic variant or mutant of SEQ ID NO:1, 3, 4, 6, 7, or 9. In an exemplary embodiment, a nucleic acid molecule of the present invention comprises a nucleotide sequence which is greater than 300–350, 350–400, 400–450, 461, 462–500, 535, 536–550, 550–600, 600–650, 650–700, 700–750, 750–800, 800–850, 850–900, 900–950, 950–1000, or more nucleotides in length and hybridizes under stringent hybridization conditions to a nucleic acid molecule of SEQ ID NO:1, 3, 4, 6, 7, or 9.

Probes based on the NIP2b, NIP2cL, and NIP2cS nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a NIP2b, NIP2cL, and NIP2cS protein, such as by measuring a level of a NIP2b, NIP2cL, and NIP2cS-encoding nucleic acid in a sample of cells from a subject e.g., detecting NIP2b, NIP2cL, and NIP2cS mRNA levels or determining whether a genomic NIP2b, NIP2cL, and NIP2cS gene has been mutated or deleted.

A nucleic acid fragment encoding a "biologically active portion of a NIP2b, NIP2cL, and NIP2cS protein" can be prepared by isolating a portion of the nucleotide sequence of SEQ ID NO:1, 3, 4, 6, 7, or 9, which encodes a polypeptide having a NIP2b, NIP2cL, and NIP2cS biological activity (the biological activities of the NIP2b, NIP2cL, and NIP2cS proteins are described herein), expressing the encoded portion of the NIP2b, NIP2cL, and NIP2cS protein (e.g., by recombinant expression in vitro) and assessing the activity of the encoded portion of the NIP2b, NIP2cL, and NIP2cS protein.

The invention further encompasses nucleic acid molecules that differ from the nucleotide sequence shown in SEQ ID NO:1, 3, 4, 6, 7, or 9, due to degeneracy of the genetic code and thus encode the same NIP2b, NIP2cL, and NIP2cS proteins as those encoded by the nucleotide sequence shown in SEQ ID NO:1, 3, 4, 6, 7, or 9. In another embodiment, an isolated nucleic acid molecule of the invention has a nucleotide sequence encoding a protein having an amino acid sequence shown in SEQ ID NO:2, 5, or 8.

In addition to the NIP2b, NIP2cL, and NIP2cS nucleotide sequences shown in SEQ ID NO:1, 3, 4, 6, 7, or 9, it will be appreciated by those skilled in the art that DNA sequence polymorphisms the lead to changes in the amino acid sequences of the NIP2b, NIP2cL, and NIP2cS proteins may exist within a population (e.g., the human population). Such genetic polymorphism in the NIP2b, NIP2cL, and NIP2cS genes may exist among individuals within a population due to natural allelic variation. As used herein, the terms "gene" and "recombinant gene" refer to nucleic acid molecules which include an open reading frame encoding a NIP2b, NIP2cL, and NIP2cS protein, preferably a mammalian NIP2b, NIP2cL, and NIP2cS protein, and can further include non-Coding regulatory sequences, and introns.

Allelic variants of human NIP2b, NIP2cL, and NIP2cS include both functional and non-functional NIP2b, NIP2cL, and NIP2cS proteins. Functional allelic variants are naturally occurring amino acid sequence variants of the humanNIP2b, NIP2cL, and NIP2cS protein that maintain the ability to bind a NIP2b, NIP2cL, and NIP2cS ligand and/or modulate programmed cell death. Functional allelic variants will typically contain only conservative substitution of one or more amino acids of SEQ ID NO:2, 5, or 8 or substitution, deletion or insertion of non-critical residues in non-critical regions of the protein.

Non-functional allelic variants are naturally occurring amino acid sequence variants of the human NIP2b, NIP2cL, and NIP2cS protein that do not have the ability to either bind a NIP2b, NIP2cL, and NIP2cS ligand and/or modulate programmed cell death. Non-functional allelic variants will typically contain a non-conservative substitution, a deletion, or insertion or premature truncation of the amino acid sequence of SEQ ID NO:2, 5, or 8 or a substitution, insertion or deletion in critical residues or critical regions.

The present invention further provides non-human orthologues of the human NIP2b, NIP2cL, and NIP2cS protein. Orthologues of the human NIP2b, NIP2cL, and NIP2cS protein are proteins that are isolated from non-human organisms and possess the same NIP2b, NIP2cL, and NIP2cS ligand binding and/or modulation of programmed cell death capabilities of the human NIP2b, NIP2cL, and NIP2cS protein. Orthologues of the human NIP2b, NIP2cL, and NIP2cS protein can readily be identified as comprising an amino acid sequence that is substantially homologous to SEQ ID NO:2, 5, or 8.

Moreover, nucleic acid molecules encoding other NIP2b, NIP2cL, and NIP2cS family members and, thus, which have a nucleotide sequence which differs from the NIP2b, NIP2cL, and NIP2cS sequences of SEQ ID NO:1, 3, 4, 6, 7, or 9, are intended to be within the scope of the invention. For example, another NIP2b, NIP2cL, and NIP2cS cDNA can be identified based on the nucleotide sequence of human NIP2b, NIP2cL, and NIP2cS. Moreover, nucleic acid molecules encoding NIP2b, NIP2cL, and NIP2cS proteins from different species, and which, thus, have a nucleotide sequence which differs from the NIP2b, NIP2cL, and NIP2cS sequences of SEQ ID NO:1, 3, 4, 6, 7, or 9, are intended to be within the scope of the invention for example, a mouse NIP2b, NIP2cL, and NIP2cS cDNA can be identified based on the nucleotide sequence of a human NIP2b, NIP2cL, and NIP2cS.

Nucleic acid molecules corresponding to natural allelic variants and homologues of the NIP2b, NIP2cL, and NIP2cS cDNAs of the invention can be isolated based on their homology to the NIP2b, NIP2cL, and NIP2cS nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the NIP2b, NIP2cL, and NIP2cS cDNAs of the invention can further be isolated by mapping to the same chromosome or locus as the NIP2b, NIP2cL, and NIP2cS gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 4, 6, 7, or 9. In other embodiment, the nucleic acid is at least 30, 50, 100, 150, 200, 250, 300, 308, 350, 400, 450, 500, 550, 600, 650, 700, 750, 800, 850, 900, or 950 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1, 3, 4, 6, 7, or 9 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the NIP2b, NIP2cL, and NIP2cS sequences that may exist in the population, the skilled artisan will further appreciate that changes can be introduced by mutation into the nucleotide sequences of SEQ ID NO:1, 3, 4, 6, 7, or 9, thereby leading to changes in the amino acid sequence of the encoded NIP2b, NIP2cL, and NIP2cS proteins, without altering the functional ability of the NIP2b, NIP2cL, and NIP2cS proteins. For example, nucleotide substitutions leading to amino acid substitutions at "non-essential" amino acid residues can be made in the sequence of SEQ ID NO:1, 3, 4, 6, 7, or 9. A "non-essential" amino acid residue is a residue that can be altered from the wild-type sequence of NIP2b, NIP2cL, and NIP2cS (e.g, the sequence of SEQ ID NO:2, 5, or 8) without altering the biological activity, whereas an "essential" amino acid residue is required for biological activity. For example, amino acid residues that are conserved among the NIP2b, NIP2cL, and NIP2cS proteins of the present invention, are predicted to be particularly unamenable to alteration. Furthermore, additional amino acid residues that are conserved between the NIP2b, NIP2cL, and NIP2cS proteins of the present invention and other members of the NIP2 family are not likely to be amenable to alteration.

Accordingly, another aspect of the invention pertains to nucleic acid molecules encoding NIP2b, NIP2cL, and NIP2cS proteins that contain changes in amino acid residues that are not essential for activity. Such NIP2b, NIP2cL, and NIP2cS proteins differ in amino acid sequence from SEQ ID NO:2, 5, or 8, yet retain biological activity. In one embodiment, the isolated nucleic acid molecule comprises a nucleotide sequence encoding a protein, wherein the protein comprises an amino acid sequence at least about 60%, 65%, 70%, 75%, 80%, 85%, 90%, 95%, 98% or more homologous to SEQ ID NO:2, 5, or 8.

An isolated nucleic acid molecule encoding a NIP2b, NIP2cL, and NIP2cS protein homologous to the protein of SEQ ID NO:2, 5, or 8 can be created by introducing one or more nucleotide substitutions, additions or deletions into the nucleotide sequence of SEQ ID NO:1, 3, 4, 6, 7, or 9, such that one or more amino acid substitutions, additions or deletions are introduced into the encoded protein. Mutations can be introduced into SEQ ID NO:1, 3, 4, 6, 7, or 9, by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a NIP2b, NIP2cL, and NIP2cS protein is preferably replaced with another amino acid residue from the same side chain family. Alternatively, in another embodiment, mutations can be introduced randomly along all or part of a NIP2b, NIP2cL, and NIP2cS coding sequence, such as by saturation mutagenesis, and the resultant mutants can be screened for NIP2b, NIP2cL, and NIP2cS biological activity to identify mutants that retain activity. Following mutagenesis of SEQ ID NO:1, 3, 4, 6, 7, or 9, the encoded protein can be expressed recombinantly and the activity of the protein can be determined.

In a preferred embodiment, a mutant NIP2b, NIP2cL, and NIP2cS protein can be assayed for the ability to (1) interact with a non-NIP2b, NIP2cL, and NIP2cS protein molecule, e.g., the adenoviral E1B 19 kDa protein or the Bcl-2 protein; (2) activate a NIP2b, NIP2cL, and NIP2cS-dependent signal transduction pathway; or (3) modulate programmed cell death.

In addition to the nucleic acid molecules encoding NIP2b, NIP2cL, and NIP2cS proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire NIP2b, NIP2cL, and NIP2cS coding strand, or to only a portion thereof. In one embodiment, an antisense nucleic acid molecule is antisense to a "coding region" of the coding strand of a nucleotide sequence encoding NIP2b, NIP2cL, and NIP2cS. The term "coding region" refers to the region of the nucleotide sequence comprising codons which are translated into amino acid residues (e.g., the coding region of human NIP2b, NIP2cL, and NIP2cS corresponds to SEQ ID NO:3, 6, and 9, respectively). In another embodiment, the antisense nucleic acid molecule is antisense to a "noncoding region" of the coding strand of a nucleotide sequence encoding NIP2b, NIP2cL, and NIP2cS. The term "noncoding region" refers to 5' and 3' sequences which flank the coding region that are not translated into amino acids (i.e., also referred to as 5' and 3' untranslated regions).

Given the coding strand sequences encoding NIP2b, NIP2cL, and NIP2cS disclosed herein (e.g., SEQ ID NO:3, 6, and 9), antisense nucleic acids of the invention can be designed according to the rules of Watson and Crick base pairing. The antisense nucleic acid molecule can be complementary to the entire coding region of NIP2b, NIP2cL, and NIP2cS mRNA, but more preferably is an oligonucleotide which is antisense to only a portion of the coding or noncoding region of NIP2b, NIP2cL, and NIP2cS mRNA. For example, the antisense oligonucleotide can be complementary to the region surrounding the translation start site of NIP2b, NIP2cL, and NIP2cS mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-diethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a NIP2b, NIP2cL, and NIP2cS protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave NIP2b, NIP2cL, and NIP2cS mRNA transcripts to thereby inhibit translation of NIP2b, NIP2cL, and NIP2cS mRNA. A ribozyme having specificity for a NIP2b, NIP2cL, and NIP2cS-encoding nucleic acid can be designed based upon the nucleotide sequence of a NIP2b, NIP2cL, and NIP2cS cDNA disclosed herein (i.e., SEQ ID NO:1, 3, 4, 6, 7, or 9. For example, a derivative of a Tetrahymena L-19 IVS RNA can be constructed in which the nucleotide sequence of the active site is complementary to the nucleotide sequence to be cleaved in a NIP2b, NIP2cL, and NIP2cS-encoding mRNA. See, e.g., Cech et al. U.S. Pat. No. 4,987,071; and Cech et al. U.S. Pat. No. 5,116,742. Alternatively, NIP2b, NIP2cL, and NIP2cS mRNA can be used to select a catalytic RNA having a specific ribonuclease activity from a pool of RNA molecules. See, e.g., Bartel, D. and Szostak, J. W. (1993) Science 261:1411–1418.

Alternatively, NIP2b, NIP2cL, and NIP2cS gene expression can be inhibited by targeting nucleotide sequences complementary to the regulatory region of the NIP2b, NIP2cL, and NIP2cS (e.g., the NIP2b, NIP2cL, and NIP2cS promoter and/or enhancers) to form triple helical structures that prevent transcription of the NIP2b, NIP2cL, and NIP2cS gene in target cells. See generally, Helene, C. (1991) Anticancer Drug Des. 6(6):569–84; Helene, C. et al. (1992) Ann. N.Y. Acad. Sci. 660:27–36; and Maher, L. J. (1992) Bioassays 14(12):807–15.

In yet another embodiment, the NIP2b, NIP2cL, and NIP2cS nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of NIP2b, NIP2cL, and NIP2cS nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of NIP2b, NIP2cL, and NIP2cS nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of NIP2b, NIP2cL, and NIP2cS can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of NIP2b, NIP2cL, and NIP2cS nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) Nucleic Acids Res. 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) Nucleic Acid Res. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84: 648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958–976) or intercalating agents. (See, e.g., Zon (1988) Pharm. Res. 5:539–549). To this end, the oligonucleotide may be conjugated to another molecule, (e.g., a peptide, hybridization triggered cross-linking agent, transport agent, or hybridization-triggered cleavage agent).

II. Isolated NIP2b, NIP2cL, and NIP2cS Proteins and Anti-NIP2b, Anti-NIP2cL, and Anti-NIP2cS Antibodies One aspect of the invention pertains to isolated NIP2b, NIP2cL, and NIP2cS proteins, and biologically active portions thereof, as well as polypeptide fragments suitable for use as immunogens to raise anti-NIP2b, anti-NIP2cL, and anti-NIP2cS antibodies. In one embodiment, native NIP2b, NIP2cL, and NIP2cS proteins can be isolated from cells or tissue sources by an appropriate purification scheme using standard protein purification techniques. In another embodiment, NIP2b, NIP2cL, and NIP2cS proteins are produced by recombinant DNA techniques. Alternative to recombinant expression, a NIP2b, NIP2cL, and NIP2cS protein or polypeptide can be synthesized chemically using standard peptide synthesis techniques.

An "isolated" or "purified" protein or biologically active portion thereof is substantially free of cellular material or other contaminating proteins from the cell or tissue source from which the NIP2b, NIP2cL, and NIP2cS protein is derived, or substantially free from chemical precursors or other chemicals when chemically synthesized. The language "substantially free of cellular material" includes preparations of NIP2b, NIP2cL, and NIP2cS protein in which the protein is separated from cellular components of the cells from which it is isolated or recombinantly produced. In one embodiment, the language "substantially free of cellular material" includes preparations of NIP2b, NIP2cL, and NIP2cS protein having less than about 30% (by dry weight) of non-NIP2b, NIP2cL, and NIP2cS protein (also referred to herein as a "contaminating protein"), more preferably less than about 20% of non-NIP2b, NIP2cL, and NIP2cS protein, still more preferably less than about 10% of non-NIP2b, NIP2cL, and NIP2cS protein, and most preferably less than about 5% non-NIP2b, NIP2cL, and NIP2cS protein. When the NIP2b, NIP2cL, and NIP2cS protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of NIP2b, NIP2cL, and NIP2cS protein in which the protein is separated from chemical precursors or other chemicals which are involved in the synthesis of the protein. In one embodiment, the language "substantially free of chemical precursors or other chemicals" includes preparations of NIP2b, NIP2cL, and NIP2cS protein having less than about 30% (by dry weight) of chemical precursors or non-NIP2b, NIP2cL, and NIP2cS chemicals, more preferably less than about 20% chemical precursors or non-NIP2b, NIP2cL, and NIP2cS chemicals, still more preferably less than about 10% chemical precursors or non-NIP2b, NIP2cL, and NIP2cS chemicals, and most preferably less than about 5% chemical precursors or non-NIP2b, NIP2cL, and NIP2cS chemicals.

As used herein, a "biologically active portion" of a NIP2b, NIP2cL, and NIP2cS protein includes a fragment of a NIP2b, NIP2cL, and NIP2cS protein which participates in an interaction between a NIP2b, NIP2cL, and NIP2cS molecule and a non-NIP2b, NIP2cL, and NIP2cS molecule. Biologically active portions of a NIP2b, NIP2cL, and NIP2cS protein include peptides comprising amino acid sequences sufficiently homologous to or derived from the amino acid sequence of the NIP2b, NIP2cL, and NIP2cS protein, e.g., the amino acid sequence shown in SEQ ID NO:2, 5, or 8, which include less amino acids than the full length NIP2b, NIP2cL, and NIP2cS proteins, and exhibit at least one activity of a NIP2b, NIP2cL, and NIP2cS protein. Typically, biologically active portions comprise a domain or motif with at least one activity of the NIP2b, NIP2cL, and NIP2cS protein, e.g., modulating cellular programmed cell death. A biologically active portion of a NIP2b, NIP2cL, and NIP2cS protein can be a polypeptide which is, for example, 10, 25, 50, 100, 200 or more amino acids in length. Biologically active portions of a NIP2b, NIP2cL, and NIP2cS protein can be used as targets for developing agents which modulate a NIP2b, NIP2cL, and NIP2cS mediated activity, e.g., programmed cell death.

In one embodiment, a biologically active portion of a NIP2b, NIP2cL, and NIP2cS protein comprises at least one transmembrane domain, and/or at least one calcium-binding domain, and/or at least one "4 transmembrane segment integral membrane protein domain" domain. It is to be understood that a preferred biologically active portion of a NIP2b, NIP2cL, and NIP2cS protein of the present invention may contain at least one of the above-identified structural domains. A more preferred biologically active portion of a NIP2b, NIP2cL, and NIP2cS protein may contain at least two of the above-identified structural domains. Moreover, other biologically active portions, in which other regions of the protein are deleted, can be prepared by recombinant techniques and evaluated for one or more of the functional activities of a native NIP2b, NIP2cL, and NIP2cS protein.

In a preferred embodiment, the NIP2b, NIP2cL, and NIP2cS protein has an amino acid sequence shown in SEQ ID NO:2, 5, or 8. In other embodiments, the NIP2b, NIP2cL, and NIP2cS protein is substantially homologous to SEQ ID NO:2, 5, or 8, and retains the functional activity of the protein of SEQ ID NO:2, 5, or 8, yet differs in amino acid sequence due to natural allelic variation or mutagenesis, as described in detail in subsection I above. Accordingly, in another embodiment, the NIP2b, NIP2cL, and NIP2cS protein is a protein which comprises an amino acid sequence at least about 60%, 65%, 70%, 75%, 80%, 85%, 90%, 95%, 98% or more homologous to SEQ ID NO:2, 5, or 8.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the NIP2b, NIP2cL, and NIP2cS amino acid sequence of SEQ ID NO:2, 5, or 8 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent indentity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available from Accelrys, Inc., San Diego, Calif.), using either a Blossom 62 matrix or a PAM250matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available from Accelrys, Inc., San Diego, Calif.), using a NWSgapdna.CMP matrix and a gap weight of 40, 50, 60, 70, or 80 and a length weight of 1, 2, 3, 4. 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used (Altschul, S. F., et al. (1990) *J. Mol.*

*Biol.* 215:403–410; Altschul, S. F., et al. (1997) Nucleic Acids Res. 25:3389–3402).

The invention also provides NIP2b, NIP2cL, and NIP2cS chimeric or fusion proteins. As used herein, a NIP2b, NIP2cL, and NIP2cS "chimeric protein" or "fusion protein" comprises a NIP2b, NIP2cL, and NIP2cS polypeptide operatively linked to a non-NIP2b, NIP2cL, and NIP2cS polypeptide. An "NIP2b, NIP2cL, and NIP2cS polypeptide" refers to a polypeptide having an amino acid sequence corresponding to NIP2b, NIP2cL, and NIP2cS. whereas a "non-NIP2b, NIP2cL, and NIP2cS polypeptide" refers to a polypeptide having an amino acid sequence corresponding to a protein which is not substantially homologous to the NIP2b, NIP2cL, and NIP2cS protein, e.g., a protein which is different from the NIP2b, NIP2cL, and NIP2cS protein and which is derived from the same or a different organism. Within a NIP2b, NIP2cL, and NIP2cS fusion protein the NIP2b, NIP2cL, and NIP2cS polypeptide can correspond to all or a portion of a NIP2b, NIP2cL, and NIP2cS protein. In a preferred embodiment, a NIP2b, NIP2cL, and NIP2cS fusion protein comprises at least one biologically active portion of a NIP2b, NIP2cL, and NIP2cS protein. In another preferred embodiment, a NIP2b, NIP2cL, and NIP2cS fusion protein comprises at least two biologically active portions of a NIP2b, NIP2cL, and NIP2cS protein. Within the fusion protein, the term "operatively linked" is intended to indicate that the NIP2b, NIP2cL, and NIP2cS polypeptide and the non-NIP2b, NIP2cL, and NIP2cS polypeptide are fused in-frame to each other. The non-NIP2b, NIP2cL, and NIP2cS polypeptide can be fused to the N-terminus or C-terminus of the NIP2b, NIP2cL, and NIP2cS polypeptide.

For example, in one embodiment, the fusion protein is a GST-NIP2b, NIP2cL, and NIP2cS fusion protein in which the NIP2b, NIP2cL, and NIP2cS sequences are fused to the C-terminus of the GST sequences. Such fusion proteins can facilitate the purification of recombinant NIP2b, NIP2cL, and NIP2cS.

In another embodiment, the fusion protein is a NIP2b, NIP2cL, and NIP2cS protein containing a heterologous signal sequence at its N-terminus. In certain host cells (e.g., mammalian host cells), expression and/or secretion of NIP2b, NIP2cL, and NIP2cS can be increased through use of a heterologous signal sequence.

The NIP2b, NIP2cL, and NIP2cS fusion proteins of the invention can be incorporated into pharmaceutical compositions and administered to a subject in vivo. The NIP2b, NIP2cL, and NIP2cS fusion proteins can be used to affect the bioavailability of a NIP2b, NIP2cL, and NIP2cS substrate. Use of NIP2b, NIP2cL, and NIP2cS fusion proteins may be useful therapeutically for the treatment of disorders caused by, for example, (i) aberrant modification or mutation of a gene encoding a NIP2b, NIP2cL, and NIP2cS protein; (ii) mis-regulation of the NIP2b, NIP2cL, and NIP2cS gene; and (iii) aberrant post-translational modification of a NIP2b, NIP2cL, and NIP2cS protein.

Moreover, the NIP2b, NIP2cL, and NIP2cS-fusion proteins of the invention can be used as immunogens to produce anti-NIP2b, NIP2cL, and NIP2cS antibodies in a subject, to purify NIP2b, NIP2cL, and NIP2cS ligands and in screening assays to identify molecules which inhibit the interaction of NIP2b, NIP2cL, and NIP2cS with a NIP2b, NIP2cL, and NIP2cS substrate.

Preferably, a NIP2b, NIP2cL, and NIP2cS chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An NIP2b, NIP2cL, and NIP2cS-encoding nucleic acid can be cloned into such an expression vector such that the fusion moiety is linked in-frame to the NIP2b, NIP2cL, and NIP2cS protein.

The present invention also pertains to variants of the NIP2b, NIP2cL, and NIP2cS proteins which function as either NIP2b, NIP2cL, and NIP2cS agonists (mimetics) or as NIP2b, NIP2cL, and NIP2cS antagonists. Variants of the NIP2b, NIP2cL, and NIP2cS proteins can be generated by mutagenesis, e.g., discrete point mutation or truncation of a NIP2b, NIP2cL, and NIP2cS protein. An agonist of the NIP2b, NIP2cL, and NIP2cS proteins can retain substantially the same, or a subset, of the biological activities of the naturally occurring form of a NIP2b, NIP2cL, and NIP2cS protein. An antagonist of a NIP2b, NIP2cL, and NIP2cS protein can inhibit one or more of the activities of the naturally occurring form of the NIP2b, NIP2cL, and NIP2cS protein by, for example, competitively modulating a NIP2b, NIP2cL, and NIP2cS-mediated activity of a NIP2b, NIP2cL, and NIP2cS protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NIP2b, NIP2cL, and NIP2cS protein.

In one embodiment, variants of a NIP2b, NIP2cL, and NIP2cS protein which function as either NIP2b, NIP2cL, and NIP2cS agonists (mimetics) or as NIP2b, NIP2cL, and NIP2cS antagonists can be identified by screening combinatorial libraries of mutants, e.g., truncation mutants, of a NIP2b, NIP2cL, and NIP2cS protein for NIP2b, NIP2cL, and NIP2cS protein agonist or antagonist activity. In one embodiment, a variegated library of NIP2b, NIP2cL, and NIP2cS variants is generated by combinatorial mutagenesis at the nucleic acid level and is encoded by a variegated gene library. A variegated library of NIP2b, NIP2cL, and NIP2cS variants can be produced by, for example, enzymatically ligating a mixture of synthetic oligonucleotides into gene sequences such that a degenerate set of potential NIP2b, NIP2cL, and NIP2cS sequences is expressible as individual polypeptides, or alternatively, as a set of larger fusion proteins (e.g., for phage display) containing the set of NIP2b, NIP2cL, and NIP2cS sequences therein. There are a variety of methods which can be used to produce libraries of potential NIP2b, NIP2cL, and NIP2cS variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NIP2b, NIP2cL, and NIP2cS sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a NIP2b, NIP2cL, and NIP2cS protein coding sequence can be used to generate a variegated population of NIP2b, NIP2cL, and NIP2cS fragments for screening and subsequent selection of variants of a NIP2b, NIP2cL, and NIP2cS protein. In one embodiment, a library of coding sequence fragments can be generated by treating a double stranded PCR fragment of a NIP2b, NIP2cL, and NIP2cS coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the NIP2b, NIP2cL, and NIP2cS protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NIP2b, NIP2cL, and NIP2cS proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify NIP2b, NIP2cL, and NIP2cS variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated NIP2b, NIP2cL, and NIP2cS library. For example, a library of expression vectors can be transfected into a cell line which ordinarily responds to a particular ligand in a NIP2b, NIP2cL, and NIP2cS-dependent manner. The transfected cells are then contacted with the ligand and the effect of expression of the mutant on signaling by the ligand can be detected, e.g., by measuring cell survival or the activity of a NIP2b, NIP2cL, and NIP2cS-regulated transcription factor. Plasmid DNA can then be recovered from the cells which score for inhibition, or alternatively, potentiation of signaling by the ligand, and the individual clones further characterized.

An isolated NIP2b, NIP2cL, and NIP2cS protein, or a portion or fragment thereof, can be used as an immunogen to generate antibodies that bind NIP2b, NIP2cL, and NIP2cS using standard techniques for polyclonal and monoclonal antibody preparation. A full-length NIP2b, NIP2cL, and NIP2cS protein can be used or, alternatively, the invention provides antigenic peptide fragments of NIP2b, NIP2cL, and NIP2cS for use as immunogens. The antigenic peptide of NIP2b, NIP2cL, and NIP2cS comprises at least 8 amino acid residues of the amino acid sequence shown in SEQ ID NO:2, 5, or 8 and encompasses an epitope of NIP2b, NIP2cL, and NIP2cS such that an antibody raised against the peptide forms a specific immune complex with NIP2b, NIP2cL, and NIP2cS. Preferably, the antigenic peptide comprises at least 10 amino acid residues, more preferably at least 15 amino acid residues, even more preferably at least 20 amino acid residues, and most preferably at least 30 amino acid residues.

Figure 4:
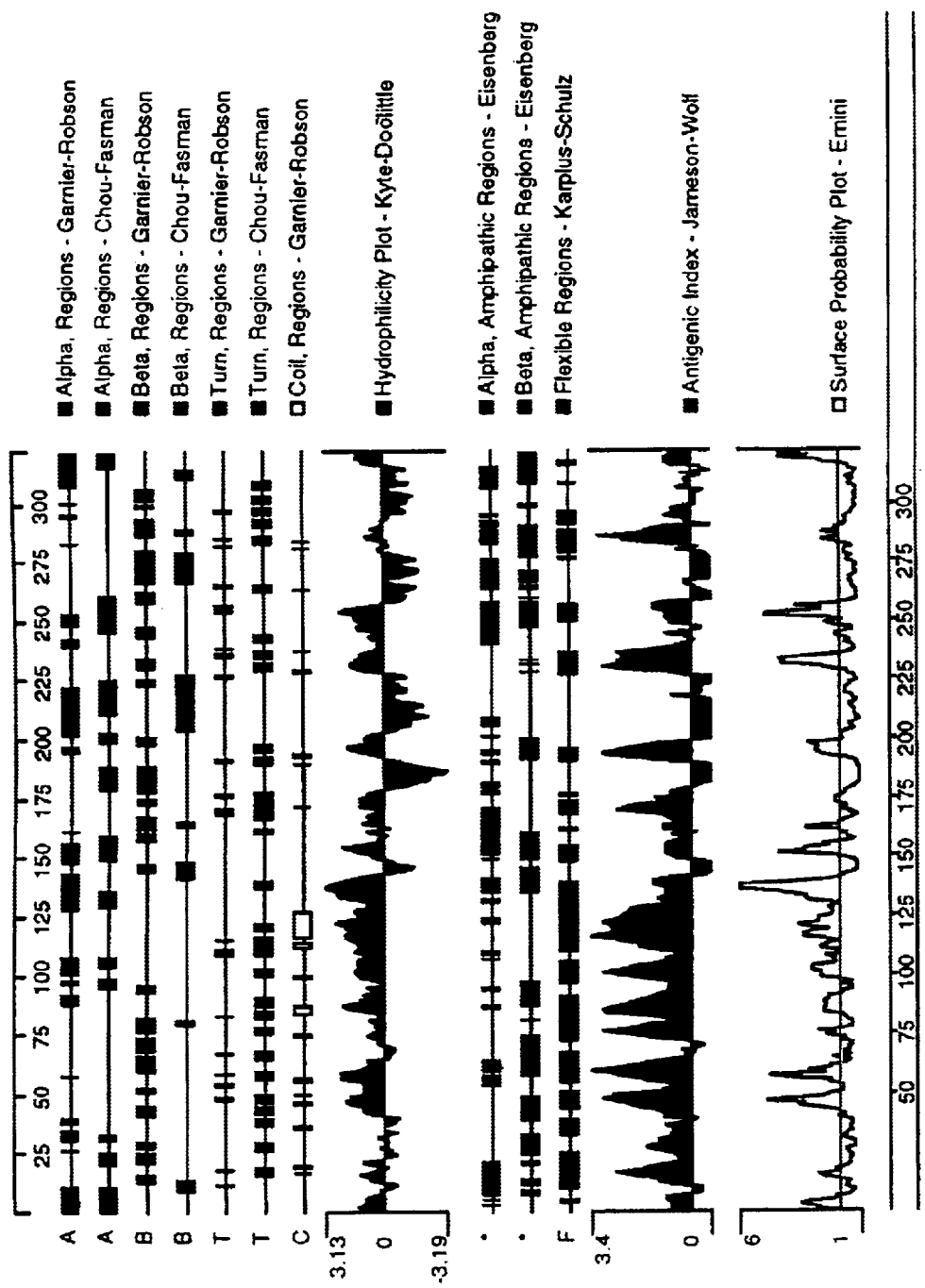
FIG. 4 depicts a structural, hydrophobicity, and antigenicity analysis of the human NIP2b protein.
Figure 6:
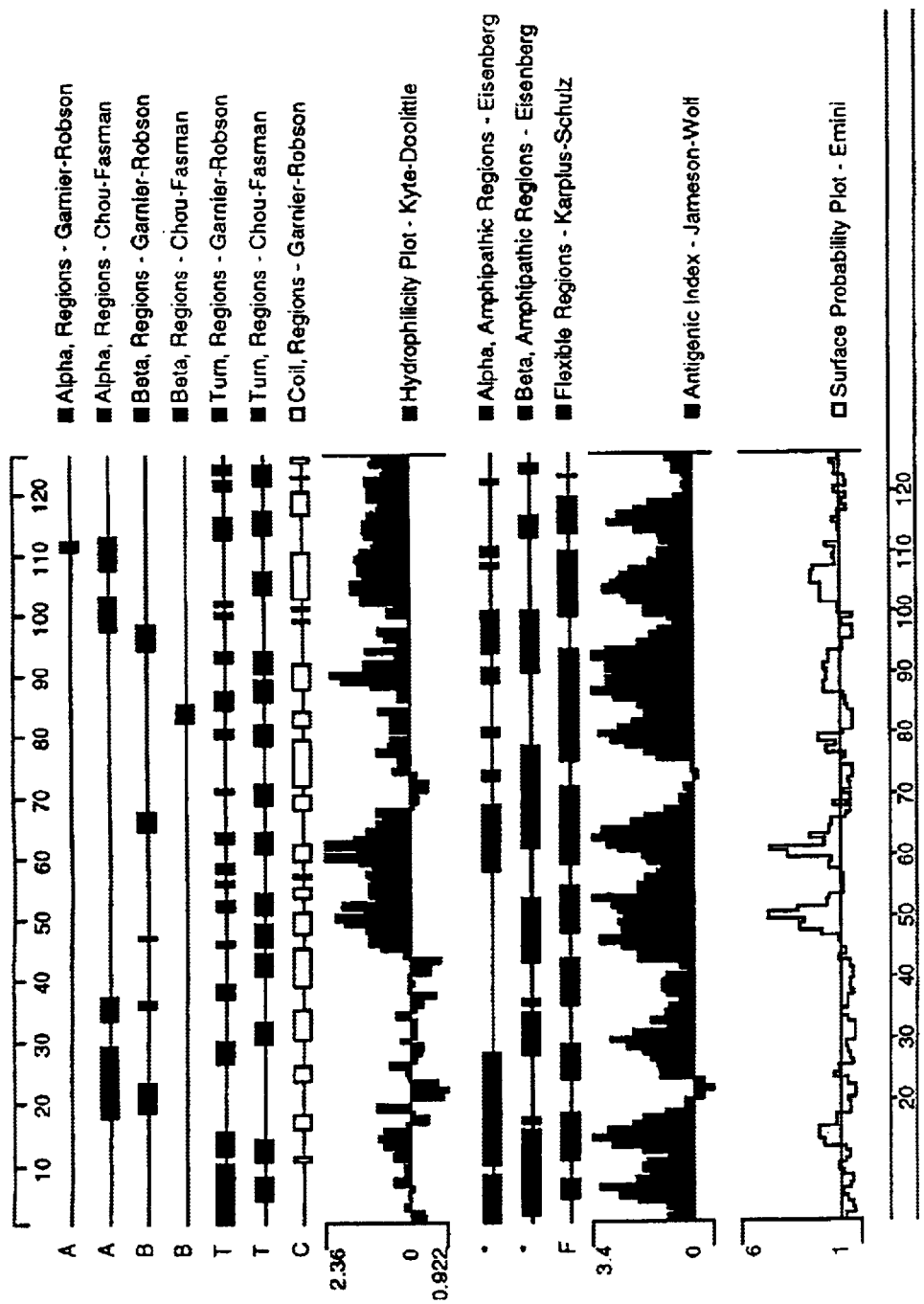
FIG. 6 depicts a structural, hydrophobicity, and antigenicity analysis of the human NIP2cS protein.

Preferred epitopes encompassed by the antigenic peptide are regions of NIP2b, NIP2cL, and NIP2cS that are located on the surface of the protein, e.g., hydrophilic regions, as well as regions with high antigenicity (see, for example, FIGS. 4, 5, and 6).

A NIP2b, NIP2cL, and NIP2cS immunogen typically is used to prepare antibodies by immunizing a suitable subject, (e.g., rabbit, goat, mouse or other mammal) with the immunogen. An appropriate immunogenic preparation can contain, for example, recombinantly expressed NIP2b, NIP2cL, and NIP2cS protein or a chemically synthesized NIP2b, NIP2cL, and NIP2cS polypeptide. The preparation can further include an adjuvant, such as Freund's complete or incomplete adjuvant, or similar immunostimulatory agent Immunization of a suitable subject with an immunogenic NIP2b, NIP2cL, and NIP2cS preparation induces a polyclonal anti-NIP2b, NIP2cL, and NIP2cS antibody response.

Accordingly, another aspect of the invention pertains to anti-NIP2b, NIP2cL, and NIP2cS antibodies. The term "antibody" as used herein refers to immunoglobulin molecules and immunologically active portions of immunoglobulin molecules, i.e., molecules that contain an antigen binding site which specifically binds (immunoreacts with) an antigen, such as NIP2b, NIP2cL, and NIP2cS. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind NIP2b, NIP2cL, and NIP2cS. The term "monoclonal antibody" or "monoclonal antibody composition", as used herein, refers to a population of antibody molecules that contain only one species of an antigen binding site capable of immunoreacting with a particular epitope of NIP2b, NIP2cL, and NIP2cS. A monoclonal antibody composition thus typically displays a single binding affinity for a particular NIP2b, NIP2cL, and NIP2cS protein with which it immunoreacts.

Polyclonal anti-NIP2b, NIP2cL, and NIP2cS antibodies can be prepared as described above by immunizing a suitable subject with a NIP2b, NIP2cL, and NIP2cS immunogen. The anti-NIP2b, NIP2cL, and NIP2cS antibody titer in the immunized subject can be monitored over time by standard techniques, such as with an enzyme linked immunosorbent assay (ELISA) using immobilized NIP2b, NIP2cL, and NIP2cS. If desired, the antibody molecules directed against NIP2b, NIP2cL, and NIP2cS can be isolated from the mammal (e.g., from the blood) and further purified by well known techniques, such as protein A chromatography to obtain the IgG fraction. At an appropriate time after immunization, e.g., when the anti-NIP2b, NIP2cL, and NIP2cS antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer*

29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a NIP2b, NIP2cL, and NIP2cS immunogen as described above, and the culture supernatants of the resulting hybridoma cells are screened to identify a hybridoma producing a monoclonal antibody that binds NIP2b, NIP2cL, and NIP2cS.

Any of the many well known protocols used for fusing lymphocytes and immortalized cell lines can be applied for the purpose of generating an anti-NIP2b, NIP2cL, and NIP2cS monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NIP2b, NIP2cL, and NIP2cS, e.g., using a standard ELISA assay.

Alternative to preparing monoclonal antibody-secreting hybridomas, a monoclonal anti-NIP2b, NIP2cL, and NIP2cS antibody can be identified and isolated by screening a recombinant combinatorial immunoglobulin library (e.g., an antibody phage display library) with NIP2b, NIP2cL, and NIP2cS to thereby isolate immunoglobulin library members that bind NIP2b, NIP2cL, and NIP2cS. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markiand et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-NIP2b, NIP2cL, and NIP2cS antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-NIP2b, NIP2cL, and NIP2cS antibody (e.g., monoclonal antibody) can be used to isolate NIP2b, NIP2cL, and NIP2cS by standard techniques, such as affinity chromatography or immunoprecipitation. An anti-NIP2b, NIP2cL, and NIP2cS antibody can facilitate the purification of natural NIP2b, NIP2cL, and NIP2cS from cells and of recombinantly produced NIP2b, NIP2cL, and NIP2cS expressed in host cells. Moreover, an anti-NIP2b, NIP2cL, and NIP2cS antibody can be used to detect NIP2b, NIP2cL, and NIP2cS protein (e.g., in a cellular lysate or cell supernatant) in order to evaluate the abundance and pattern of expression of the NIP2b, NIP2cL, and NIP2cS protein. Anti-NIP2b, NIP2cL, and NIP2cS antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

III. Recombinant Expression Vectors and Host Cells

Another aspect of the invention pertains to vectors, preferably expression vectors, containing a nucleic acid encoding a NIP2b, NIP2cL, and NIP2cS protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., NIP2b, NIP2cL, and NIP2cS proteins, mutant forms of NIP2b, NIP2cL, and NIP2cS proteins, fusion proteins, and the like).

The recombinant expression vectors of the invention can be designed for expression of NIP2b, NIP2cL, and NIP2cS proteins in prokaryotic or eukaryotic cells. For example, NIP2b, NIP2cL, and NIP2cS proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GSI), maltose E binding protein, or protein A, respectively, to the target recombinant protein.

Purified fusion proteins can be utilized in NIP2b, NIP2cL, and NIP2cS activity assays, (e.g., direct assays or competitive assays described in detail below), or to generate antibodies specific for NIP2b, NIP2cL, and NIP2cS proteins, for example. In a preferred embodiment, a NIP2b, NIP2cL, and NIP2cS fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the NIP2b, NIP2cL, and NIP2cS expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (In Vitrogen Corp, San Diego, Calif.).

Alternatively, NIP2b, NIP2cL, and NIP2cS proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine box promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to NIP2b, NIP2cL, and NIP2cS mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a NIP2b, NIP2cL, and NIP2cS nucleic acid molecule of the invention is introduced, erg., a NIP2b, NIP2cL, and NIP2cS nucleic acid molecule within a recombinant expression vector or a NIP2b, NIP2cL, and NIP2cS nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a NIP2b, NIP2cL, and NIP2cS protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a NIP2b, NIP2cL, and NIP2cS protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a NIP2b, NIP2cL, and NIP2cS protein.

Accordingly, the invention further provides methods for producing a NIP2b, NIP2cL, and NIP2cS protein using the host cells of the invention. In one embodiment, the method comprises culturing the host cell of invention (into which a recombinant expression vector encoding a NIP2b, NIP2cL, and NIP2cS protein has been introduced) in a suitable medium such that a NIP2b, NIP2cL, and NIP2cS protein is produced. In another embodiment, the method further comprises isolating a NIP2b, NIP2cL, and NIP2cS protein from the medium or the host cell.

The host cells of the invention can also be used to produce non-human transgenic animals. For example, in one embodiment, a host cell of the invention is a fertilized oocyte or an embryonic stem cell into which NIP2b, NIP2cL, and NIP2cS-coding sequences have been introduced. Such host cells can then be used to create non-human transgenic animals in which exogenous NIP2b, NIP2cL, and NIP2cS sequences have been introduced into their genome or homologous recombinant animals in which endogenous NIP2b, NIP2cL, and NIP2cS sequences have been altered. Such animals are useful for studying the function and/or activity of a NIP2b, NIP2cL, and NIP2cS and for identifying and/or evaluating modulators of NIP2b, NIP2cL, and NIP2cS activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NIP2b, NIP2cL, and NIP2cS gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a NIP2b, NIP2cL, and NIP2cS-encoding nucleic acid into the male pronuclei of a fertilized oocyte, e.g., by microinjection, retroviral infection, and allowing the oocyte to develop in a pseudopregnant female foster animal. The NIP2b, NIP2cL, and NIP2cS cDNA sequence of SEQ ID NO:1, 4, or 7 can be introduced as a transgene into the genome of a non-human animal. Alternatively, a nonhuman homologue of a human NIP2b, NIP2cL, and NIP2cS gene, such as a mouse or rat NIP2b, NIP2cL, and NIP2cS gene, can be used as a transgene. Alternatively, a NIP2b, NIP2cL, and NIP2cS gene homologue, such as another NIP2 family member, can be isolated based on hybridization to the NIP2b, NIP2cL, and NIP2cS cDNA sequences of SEQ ID NO:1, 3, 4, 6, 7, (described further in subsection I above) and used as a transgene. Intronic sequences and polyadenylation signals can also be included in the transgene to increase the efficiency of expression of the transgenic. A tissue-specific regulatory sequence(s) can be operably linked to a NIP2b, NIP2cL, and NIP2cS transgene to direct expression of a NIP2b, NIP2cL, and NIP2cS protein to particular cells. Methods for generating transgenic animals via embryo manipulation and microinjection, particularly animals such as mice, have become conventional in the art and are described, for example in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y, 1986). Similar methods are used for production of other transgenic animals. A transgenic founder animal can be identified based upon the presence of a NIP2b, NIP2cL, and NIP2cS transgene in its genome and/or expression of NIP2b, NIP2cL, and NIP2cS mRNA in tissues or cells of the animals. A transgenic founder animal can then be used to breed additional animals carrying the transgene. Moreover, transgenic animals carrying a transgene encoding a NIP2b, NIP2cL, and NIP2cS protein can further be bred to other transgenic animals carrying other transgenes.

To create a homologous recombinant animal, a vector is prepared which contains at least a portion of a NIP2b, NIP2cL, and NIP2cS gene into which a deletion, addition or substitution has been introduced to thereby alter, e.g., functionally disrupt, the NIP2b, NIP2cL, and NIP2cS gene. The NIP2b, NIP2cL, and NIP2cS gene can be a human gene (e.g., the cDNA of SEQ ID NO:3, 6, or 9), but more preferably, is a non-human homologue of a human NIP2b, NIP2cL, and NIP2cS gene (e.g., a cDNA isolated by stringent hybridization with the nucleotide sequence of SEQ ID NO:1, 4, or 7). For example, a mouse NIP2b, NIP2cL, and NIP2cS gene can be used to construct a homologous recombination nucleic acid molecule, e.g., a vector, suitable for altering an endogenous NIP2b, NIP2cL, and NIP2cS gene in the mouse genome. In a preferred embodiment, the homologous recombination nucleic acid molecule is designed such that, upon homologous recombination, the endogenous NIP2b, NIP2cL, and NIP2cS gene is functionally disrupted (i.e., no longer encodes a functional protein; also referred to as a "knock out" vector). Alternatively, the homologous recombination nucleic acid molecule can be designed such that, upon homologous recombination, the endogenous NIP2b, NIP2cL, and NIP2cS gene is mutated or otherwise altered but still encodes functional protein (e.g., the upstream regulatory region can be altered to thereby alter the expression of the endogenous NIP2b, NIP2cL, and NIP2cS protein). In the homologous recombination nucleic acid molecule, the altered portion of the NIP2b, NIP2cL, and NIP2cS gene is flanked at its 5' and 3' ends by additional nucleic acid sequence of the NIP2b, NIP2cL, and NIP2cS gene to allow for homologous recombination to occur between the exogenous NIP2b, NIP2cL, and NIP2cS gene carried by the homologous recombination nucleic acid molecule and an endogenous NIP2b, NIP2cL, and NIP2cS gene in a cell, e.g., an embryonic stem cell. The additional flanking NIP2b, NIP2cL, and NIP2cS nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capeechi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced NIP2b, NIP2cL, and NIP2cS gene has homologously recombined with the endogenous NIP2b, NIP2cL, and NIP2cS gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused. e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The NIP2b, NIP2cL, and NIP2cS nucleic acid molecules, fragments of NIP2b, NIP2cL, and NIP2cS proteins, and anti-NIP2b, anti-NIP2cL, and anti-NIP2cS antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a NIP2b, NIP2cL, and NIP2cS protein or an anti-NIP2b, anti-NIP2cL, and anti-NIP2cS antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a NIP2b, NIP2cL, and NIP2cS protein of the invention has one or more of the following activities: (1) it interacts with a non-NIP2b, NIP2cL, and NIP2cS protein molecule, e.g., the adenoviral E1B 19 kDa protein or the Bcl-2 protein; (2) it activates a NIP2b, NIP2cL, and NIP2cS-dependent signal transduction pathway; and (3) it modulates programmed cell death, and, thus, can be used to, for example, (1) modulate the interaction with a non-NIP2b, NIP2cL, and NIP2cS protein molecule; (2) to activate a NIP2b, NIP2cL, and NIP2cS-dependent signal transduction pathway; and (3) to modulate programmed cell death.

The isolated nucleic acid molecules of the invention can be used, for example, to express NIP2b, NIP2cL, and NIP2cS protein (e.g., via a recombinant expression vector in a host cell in gene therapy applications), to detect NIP2b, NIP2cL, and NIP2cS mRNA (e.g., in a biological sample) or a genetic alteration in a NIP2b, NIP2cL, and NIP2cS gene, and to modulate NIP2b, NIP2cL, and NIP2cS activity, as described further below. The NIP2b, NIP2cL, and NIP2cS proteins can be used to treat disorders characterized by insufficient or excessive production of a NIP2b, NIP2cL, and NIP2cS substrate or production of NIP2b, NIP2cL, and NIP2cS inhibitors. In addition, the NIP2b, NIP2cL, and NIP2cS proteins can be used to screen for naturally occurring NIP2b, NIP2cL, and NIP2cS substrates, to screen for drugs or compounds which modulate NIP2b, NIP2cL, and NIP2cS activity, as well as to treat disorders characterized by insufficient or excessive production of NIP2b, NIP2cL, and NIP2cS protein or production of NIP2b, NIP2cL, and NIP2cS protein forms which have decreased or aberrant activity compared to NIP2b, NIP2cL, and NIP2cS wild type protein (e.g., disorders associated with programmed cell death). Moreover, the anti-NIP2b, NIP2cL, and NIP2cS antibodies of the invention can be used to detect and isolate NIP2b, NIP2cL, and NIP2cS proteins, regulate the bioavailability of NIP2b, NIP2cL, and NIP2cS proteins, and modulate NIP2b, NIP2cL, and NIP2cS activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to NIP2b, NIP2cL, and NIP2cS proteins, have a stimulatory or inhibitory effect on, for example, NIP2b, NIP2cL, and NIP2cS expression or NIP2b, NIP2cL, and NIP2cS activity, or have a stimulatory or inhibitory effect on, for example, the expression or activity of NIP2b, NIP2cL, and NIP2cS substrate.

In one embodiment, the invention provides assays for screening candidate or test compounds which are substrates of a NIP2b, NIP2cL, and NIP2cS protein or polypeptide or biologically active portion thereof. In another embodiment, the invention provides assays for screening candidate or test compounds which bind to or modulate the activity of a NIP2b, NIP2cL, and NIP2cS protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12–145).

Examples of methods for the synthesis of molecular libraries can be found in the art, for example in: DeWitt et al. (1993) *Proc. Natl. Acad Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plaids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a NIP2b, NIP2cL, and NIP2cS protein or biologically active portion thereof is contacted with a test compound and the ability of the test compound to modulate NIP2b, NIP2cL, and NIP2cS activity is determined. Determining the ability of the test compound to modulate NIP2b, NIP2cL, and NIP2cS activity can be accomplished by monitoring, for example, the survival of a cell which expresses NIP2b, NIP2cL, and NIP2cS or the activity of a NIP2b, NIP2cL, and NIP2cS-regulated transcription factor. The cell, for example, can be of mammalian origin, e.g., a neuronal cell.

The ability of the test compound to modulate NIP2b, NIP2cL, and NIP2cS binding to a substrate or to bind to NIP2b, NIP2cL, and NIP2cS can also be determined. Determining the ability of the test compound to modulate NIP2b, NIP2cL, and NIP2cS binding to a substrate can be accomplished, for example, by coupling the NIP2b, NIP2cL, and NIP2cS substrate with a radioisotope or enzymatic label such that binding of the NIP2b, NIP2cL, and NIP2cS substrate to NIP2b, NIP2cL, and NIP2cS can be determined by detecting the labeled NIP2b, NIP2cL, and NIP2cS substrate in a complex. Determining the ability of the test compound to bind NIP2b, NIP2cL, and NIP2cS can be accomplished, for example, by coupling the compound with a radioisotope or enzymatic label such that binding of the compound to NIP2b, NIP2cL, and NIP2cS can be determined by detecting the labeled NIP2b, NIP2cL, and NIP2cS compound in a complex. For example, compounds (e.g., NIP2b, NIP2cL, and NIP2cS substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a NIP2b, NIP2cL, and NIP2cS substrate) to interact with NIP2b, NIP2cL, and NIP2cS without the labeling of any of the interactants. For example, a microphysiometer can be used to detect the interaction of a compound with NIP2b, NIP2cL, and NIP2cS without the labeling of either the compound or the NIP2b, NIP2cL, and NIP2cS. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and NIP2b, NIP2cL, and NIP2cS.

In another embodiment, an assay is a cell-based assay comprising contacting a cell expressing a NIP2b, NIP2cL, and NIP2cS target molecule (e.g., a NIP2b, NIP2cL, and NIP2cS substrate) with a test compound and determining the ability of the test compound to modulate (e.g. stimulate or inhibit) the activity of the NIP2b, NIP2cL, and NIP2cS target molecule. Determining the ability of the test compound to modulate the activity of a NIP2b, NIP2cL, and NIP2cS target molecule can be accomplished, for example, by determining the ability of the NIP2b, NIP2cL, and NIP2cS protein to bind to or interact with the NIP2b, NIP2cL, and NIP2cS target molecule.

Determining the ability of the NIP2b, NIP2cL, and NIP2cS protein or a biologically active fragment thereof, to bind to or interact with a NIP2b, NIP2cL, and NIP2cS target molecule can be accomplished by one of the methods described above for determining direct binding. In a preferred embodiment, determining the ability of the NIP2b, NIP2cL, and NIP2cS protein to bind to or interact with a NIP2b, NIP2cL, and NIP2cS target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a NIP2b, NIP2cL, and NIP2cS protein or biologically active portion thereof is contacted with a test compound and the ability of the test compound to bind to the NIP2b, NIP2cL, and NIP2cS protein or biologically active portion thereof is determined. Preferred biologically active portions of the NIP2b, NIP2cL, and NIP2cS proteins to be used in assays of the present invention include fragments which participate in interactions with non-NIP2b, NIP2cL, and NIP2cS molecules, e.g., fragments with high surface probability scores (see, for example, FIGS. 4, 5, and 6). Binding of the test compound to the NIP2b, NIP2cL, and NIP2cS protein can be determined either directly or indirectly as described above. In a preferred embodiment, the assay includes contacting the NIP2b, NIP2cL, and NIP2cS protein or biologically active portion thereof with a known compound which binds NIP2b, NIP2cL, and NIP2cS to form an assay mixture, contacting the assay mixture with a test compound, and determining the ability of the test compound to interact with a NIP2b, NIP2cL, and NIP2cS protein, wherein determining the ability of the test compound to interact with a NIP2b, NIP2cL, and NIP2cS protein comprises determining the ability of the test compound to preferentially bind to NIP2b, NIP2cL, and NIP2cS or biologically active portion thereof as compared to the known compound.

In another embodiment, the assay is a cell-free assay in which a NIP2b, NIP2cL, and NIP2cS protein or biologically active portion thereof is contacted with a test compound and the ability of the test compound to modulate (e.g., stimulate or inhibit) the activity of the NIP2b, NIP2cL, and NIP2cS protein or biologically active portion thereof is determined. Determining the ability of the test compound to modulate the activity of a NIP2b, NIP2cL, and NIP2cS protein can be accomplished, for example, by determining the ability of the NIP2b, NIP2cL, and NIP2cS protein to bind to a NIP2b, NIP2cL, and NIP2cS target molecule by one of the methods described above for determining direct binding. Determining the ability of the NIP2b, NIP2cL, and NIP2cS protein to bind to a NIP2b, NIP2cL, and NIP2cS target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a NIP2b, NIP2cL, and NIP2cS protein can be accomplished by determining the ability of the NIP2b, NIP2cL, and NIP2cS protein to further modulate the activity of a downstream effector of a NIP2b, NIP2cL, and NIP2cS target molecule. For example, the activity of the effector molecule on an appropriate target can be determined or the binding of the effector to an appropriate target can be determined as previously described.

In yet another embodiment, the cell-free assay involves contacting a NIP2b, NIP2cL, and NIP2cS protein or biologically active portion thereof with a known compound which binds the NIP2b, NIP2cL, and NIP2cS protein to form an assay mixture, contacting the assay mixture with a test compound, and determining the ability of the test compound to interact with the NIP2b, NIP2cL, and NIP2cS protein, wherein determining the ability of the test compound to interact with the NIP2b, NIP2cL, and NIP2cS protein comprises determining the ability of the NIP2b, NIP2cL, and NIP2cS protein to preferentially bind to or modulate the activity of a NIP2b, NIP2cL, and NIP2cS target molecule.

The cell-free assays of the present invention are amenable to use of both soluble and/or membrane-bound forms of isolated proteins (e.g., NIP2b, NIP2cL, and NIP2cS proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either NIP2b, NIP2cL, and NIP2cS or its target molecule to facilitate separation of complexed from uncomplexed forms of one or both of the proteins, as well as to accommodate automation of the assay. Binding of a test compound to a NIP2b, NIP2cL, and NIP2cS protein, or interaction of a NIP2b, NIP2cL, and NIP2cS protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/NIP2b, NIP2cL, and NIP2cS fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or NIP2b, NIP2cL, and NIP2cS protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NIP2b, NIP2cL, and NIP2cS binding or activity determined using standard techniques.

Other techniques for immobilizing proteins on matrices can also be used in the screening assays of the invention. For example, either a NIP2b, NIP2cL, and NIP2cS protein or a NIP2b, NIP2cL, and NIP2cS target molecule can be immobilized utilizing conjugation of biotin and streptavidin. Biotinylated NIP2b, NIP2cL, and NIP2cS protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with NIP2b, NIP2cL, and NIP2cS protein or target molecules but which do not interfere with binding of the NIP2b, NIP2cL, and NIP2cS protein to its target molecule can be derivatized to the wells of the plate, and unbound target or NIP2b, NIP2cL, and NIP2cS protein trapped in the wells by antibody conjugation. Methods for detecting such complexes, in addition to those described above for the GST-immobilized complexes, include immunodetection of complexes using antibodies reactive with the NIP2b, NIP2cL, and NIP2cS protein or target molecule, as well as enzyme-linked assays which rely on detecting an enzymatic activity associated with the NIP2b, NIP2cL, and NIP2cS protein or target molecule.

In another embodiment, modulators of NIP2b, NIP2cL, and NIP2cS expression are identified in a method wherein a cell is contacted with a candidate compound and the expression of NIP2b, NIP2cL, and NIP2cS mRNA or protein in the cell is determined. The level of expression of NIP2b, NIP2cL, and NIP2cS mRNA or protein in the presence of the candidate compound is compared to the level of expression of NIP2b, NIP2cL, and NIP2cS mRNA or protein in the absence of the candidate compound. The candidate compound can then be identified as a modulator of NIP2b, NIP2cL, and NIP2cS expression based on this comparison. For example, when expression of NIP2b, NIP2cL, and NIP2cS mRNA or protein is greater (statistically significantly greater) in the presence of the candidate compound than in its absence, the candidate compound is identified as a stimulator of NIP2b, NIP2cL, and NIP2cS mRNA or protein expression. Alternatively, when expression of NIP2b, NIP2cL, and NIP2cS mRNA or protein is less (statistically significantly less) in the presence of the candidate compound than in its absence, the candidate compound is identified as an inhibitor of NIP2b, NIP2cL, and NIP2cS mRNA or protein expression. The level of NIP2b, NIP2cL, and NIP2cS mRNA or protein expression in the cells can be determined by methods described herein for detecting NIP2b, NIP2cL, and NIP2cS mRNA or protein.

In yet another aspect of the invention, the NIP2b, NIP2cL, and NIP2cS proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with NIP2b, NIP2cL, and NIP2cS ("NIP2b-binding proteins", "NIP2cL-binding proteins", and "NIP2cS-binding proteins" or "NIP2b-bp", "NIP2cL-bp", and "NIP2cS-bp") and are involved in NIP2b, NIP2cL, and NIP2cS activity. Such NIP2b, NIP2cL, and NIP2cS-binding proteins are also likely to be involved in the propagation of signals by the NIP2b, NIP2cL, and NIP2cS proteins or NIP2b, NIP2cL, and NIP2cS targets as, for example, downstream elements of a NIP2b, NIP2cL, and NIP2cS-mediated signaling pathway. Alternatively, such NIP2b, NIP2cL, and NIP2cS-binding proteins are likely to be NIP2b, NIP2cL, and NIP2cS inhibitors.

The two-hybrid system is based on the modular nature of most transcription factors, which consist of separable DNA-binding and activation domains. Briefly, the assay utilizes two different DNA constructs. In one construct, the gene that codes for a NIP2b, NIP2cL, and NIP2cS protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NIP2b, NIP2cL, and NIP2cS-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the NIP2b, NIP2cL, and NIP2cS protein.

This invention further pertains to novel agents identified by the above-described screening assays. Accordingly, it is within the scope of this invention to further use an agent identified as described herein in an appropriate animal model. For example, an agent identified as described herein (e.g., a NIP2b, NIP2cL, and NIP2cS modulating agent, an antisense NIP2b, NIP2cL, and NIP2cS nucleic acid molecule, a NIP2b, NIP2cL, and NIP2cS-specific antibody, or a NIP2b, NIP2cL, and NIP2cS-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the NIP2b, NIP2cL, and NIP2cS nucleotide sequences, described herein, can be used to map the location of the NIP2b, NIP2cL, and NIP2cS genes on a chromosome. The mapping of the NIP2b, NIP2cL, and NIP2cS sequences to chromosomes is an important first step in correlating these sequences with genes associated with disease.

Briefly, NIP2b, NIP2cL, and NIP2cS genes can be mapped to chromosomes by preparing PCR primers (preferably 15–25 bp in length) from the NIP2b, NIP2cL, and NIP2cS nucleotide sequences. Computer analysis of the NIP2b, NIP2cL, and NIP2cS sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the NIP2b, NIP2cL, and NIP2cS sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NIP2b, NIP2cL, and NIP2cS nucleotide sequences to design oligonucleotide primers, sublocalization can be achieved with panels of fragments from specific chromosomes. Other mapping strategies which can similarly be used to map a NIP2b, NIP2cL, and NIP2cS sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the NIP2b, NIP2cL, and NIP2cS gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The NIP2b, NIP2cL, and NIP2cS sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the NIP2b, NIP2cL, and NIP2cS nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The NIP2b, NIP2cL, and NIP2cS nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 4, or 7 can comfortably provide positive individual identification with a panel of perhaps 10 to 1,000 primers which each yield a noncoding amplified sequence of 100 bases. If predicted coding sequences, such as those in SEQ ID NO:3, 6, or 9 are used, a more appropriate number of primers for positive individual identification would be 500–2,000.

If a panel of reagents from NIP2b, NIP2cL, and NIP2cS nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial NIP2b, NIP2cL, and NIP2cS Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 4, or 7 are particularly appropriate for this use as greater numbers of polymorphisms occur in the noncoding regions, making it easier to differentiate individuals using this technique. Examples of polynucleotide reagents include the NIP2b, NIP2cL, and NIP2cS nucleotide sequences or portions thereof, e.g., fragments derived from the noncoding regions of SEQ ID NO:1, 4, or 7 having a length of at least 20 bases, preferably at least 30 bases.

The NIP2b, NIP2cL, and NIP2cS nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such NIP2b, NIP2cL, and NIP2cS probes can be used to identify tissue by species and/or by organ type.

In a similar fashion, these reagents, e.g., NIP2b, NIP2cL, and NIP2cS primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining NIP2b, NIP2cL, and NIP2cS protein and/or nucleic acid expression as well as NIP2b, NIP2cL, and NIP2cS activity, in the context of a biological sample (e.g., blood, serum, cells, tissue) to thereby determine whether an individual is afflicted with a disease or disorder, or is at risk of developing a disorder, associated with aberrant NIP2b, NIP2cL, and NIP2cS expression or activity. The invention also provides for prognostic (or predictive) assays for determining whether an individual is at risk of developing a disorder associated with NIP2b, NIP2cL, and NIP2cS protein, nucleic acid expression or activity. For example, mutations in a NIP2b, NIP2cL, and NIP2cS gene can be assayed in a biological sample. Such assays can be used for prognostic or predictive purpose to thereby phophylactically treat an individual prior to the onset of a disorder characterized by or associated with NIP2b, NIP2cL, and NIP2cS protein, nucleic acid expression or activity.

Another aspect of the invention pertains to monitoring the influence of agents (e.g., drugs, compounds) on the expression or activity of NIP2b, NIP2cL, and NIP2cS in clinical trials.

These and other agents are described in further detail in the following sections.

1. Diagnostic Assays

An exemplary method for detecting the presence or absence of NIP2b, NIP2cL, and NIP2cS protein or nucleic acid in a biological sample involves obtaining a biological sample from a test subject and contacting the biological sample with a compound or an agent capable of detecting NIP2b, NIP2cL, and NIP2cS protein or nucleic acid (e.g., mRNA, genomic DNA) that encodes NIP2b, NIP2cL, and NIP2cS protein such that the presence of NIP2b, NIP2cL, and NIP2cS protein or nucleic acid is detected in the biological sample. A preferred agent for detecting NIP2b, NIP2cL, and NIP2cS mRNA or genomic DNA is a labeled nucleic acid probe capable of hybridizing to NIP2b, NIP2cL, and NIP2cS mRNA or genomic DNA. The nucleic acid probe can be, for example, a full-length NIP2b, NIP2cL, and NIP2cS nucleic acid, such as the nucleic acid of SEQ ID NO:1, 3, 4, 6, 7, or 9, or a portion thereof, such as an oligonucleotide of at least 15, 30, 50, 100, 250 or 500 nucleotides in length and sufficient to specifically hybridize under stringent conditions to NIP2b, NIP2cL, and NIP2cS mRNA or genomic DNA. Other suitable probes for use in the diagnostic assays of the invention are described herein.

A preferred agent for detecting NIP2b, NIP2cL, and NIP2cS protein is an antibody capable of binding to NIP2b, NIP2cL, and NIP2cS protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect NIP2b, NIP2cL, and NIP2cS mRNA, protein, or genomic DNA in a biological sample in vitro as well as in vivo. For example, in vitro techniques for detection of NIP2b, NIP2cL, and NIP2cS mRNA include Northern hybridizations and in situ hybridizations. In vitro techniques for detection of NIP2b, NIP2cL, and NIP2cS protein include enzyme linked immunosorbent assays (ELISAs), Western blots, imnmunoprecipitations and immunofluorescence. In vitro techniques for detection of NIP2b, NIP2cL, and NIP2cS genomic DNA include Southern hybridizations. Furthermore, in vivo techniques for detection of NIP2b, NIP2cL, and NIP2cS protein include introducing into a subject a labeled anti-NIP2b, NIP2cL, and NIP2cS antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting NIP2b, NIP2cL, and NIP2cS protein, mRNA, or genomic DNA, such that the presence of NIP2b, NIP2cL, and NIP2cS protein, mRNA or genomic DNA is detected in the biological sample, and comparing the presence of NIP2b, NIP2cL, and NIP2cS protein, mRNA or genomic DNA in the control sample with the presence of NIP2b, NIP2cL, and NIP2cS protein, mRNA or genomic DNA in the test sample.

The invention also encompasses kits for detecting the presence of NIP2b, NIP2cL, and NIP2cS in a biological sample. For example, the kit can comprise a labeled compound or agent capable of detecting NIP2b, NIP2cL, and NIP2cS protein or mRNA in a biological sample; means for determining the amount of NIP2b, NIP2cL, and NIP2cS in the sample; and means for comparing the amount of NIP2b, NIP2cL, and NIP2cS in the sample with a standard. The compound or agent can be packaged in a suitable container. The kit can further comprise instructions for using the kit to detect NIP2b, NIP2cL, and NIP2cS protein or nucleic acid.

2. Prognostic Assays

The diagnostic methods described herein can furthermore be utilized to identify subjects having or at risk of developing a disease or disorder associated with aberrant NIP2b, NIP2cL, and NIP2cS expression or activity. As used herein, the term "aberrant" includes a NIP2b, NIP2cL, and NIP2cS expression or activity which deviates from the wild type NIP2b, NIP2cL, and NIP2cS expression or activity. Aberrant expression or activity includes increased or decreased expression or activity, as well as expression or activity which does not follow the wild type developmental pattern of expression or the subcellular pattern of expression. For example, aberrant NIP2b, NIP2cL, and NIP2cS expression or activity is intended to include the cases in which a mutation in the NIP2b, NIP2cL, and NIP2cS gene causes the NIP2b, NIP2cL, and NIP2cS gene to be under-expressed or over-expressed and situations in which such mutations result in a non-functional NIP2b, NIP2cL, and NIP2cS protein or a protein which does not function in a wild-type fashion, e.g., a protein which does not interact with a NIP2b, NIP2cL, and NIP2cS ligand or one which interacts with a non-NIP2b, non-NIP2cL, and non-NIP2cS ligand.

The assays described herein, such as the preceding diagnostic assays or the following assays, can be utilized to identify a subject having or at risk of developing a disorder associated with a misregulation in NIP2b, NIP2cL, and NIP2cS protein activity or nucleic acid expression, such as a disorder characterized by deregulated programmed cell death. Alternatively, the prognostic assays can be utilized to identify a subject having or at risk for developing a disorder associated with a misregulation in NIP2b, NIP2cL, and NIP2cS protein activity or nucleic acid expression, such as a disorder characterized by deregulated programmed cell death. Thus, the present invention provides a method for identifying a disease or disorder associated with aberrant NIP2b, NIP2cL, and NIP2cS expression or activity in which a test sample is obtained from a subject and NIP2b, NIP2cL, and NIP2cS protein or nucleic acid (e.g., mRNA or genomic DNA) is detected, wherein the presence of NIP2b, NIP2cL, and NIP2cS protein or nucleic acid is diagnostic for a subject having or at risk of developing a disease or disorder associated with aberrant NIP2b, NIP2cL, and NIP2cS expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NIP2b, NIP2cL, and NIP2cS expression or activity. For example, such methods can be used to determine whether a subject can be effectively treated with an agent for a disorder characterized by deregulated programmed cell death. Thus, the present invention provides methods for determining whether a subject can be effectively treated with an agent for a disorder associated with aberrant NIP2b, NIP2cL, and NIP2cS expression or activity in which a test sample is obtained and NIP2b, NIP2cL, and NIP2cS protein or nucleic acid expression or activity is detected (e.g., wherein the abundance of NIP2b, NIP2cL, and NIP2cS protein or nucleic acid expression or activity is diagnostic for a subject that can be administered the agent to treat a disorder associated with aberrant NIP2b, NIP2cL, and NIP2cS expression or activity).

The methods of the invention can also be used to detect genetic alterations in a NIP2b, NIP2cL, and NIP2cS gene, thereby determining if a subject with the altered gene is at risk for a disorder characterized by misregulation in NIP2b, NIP2cL, and NIP2cS protein activity or nucleic acid expression, such as a neurodegenerative disorder. In preferred embodiments, the methods include detecting, in a sample of cells from the subject, the presence or absence of a genetic alteration characterized by at least one of an alteration affecting the integrity of a gene encoding a NIP2b, NIP2cL, and NIP2cS-protein, or the mis-expression of the NIP2b, NIP2cL, and NIP2cS gene. For example, such genetic alterations can be detected by ascertaining the existence of at least one of 1) a deletion of one or more nucleotides from a NIP2b, NIP2cL, and NIP2cS gene; 2) an addition of one or more nucleotides to a NIP2b, NIP2cL, and NIP2cS gene; 3) a substitution of one or more nucleotides of a NIP2b, NIP2cL, and NIP2cS gene, 4) a chromosomal rearrangement of a NIP2b, NIP2cL, and NIP2cS gene; 5) an alteration in the level of a messenger RNA transcript of a NIP2b, NIP2cL, and NIP2cS gene, 6) aberrant modification of a NIP2b, NIP2cL, and NIP2cS gene, such as of the methylation pattern of the genomic DNA, 7) the presence of a non-wild type splicing pattern of a messenger RNA transcript of a NIP2b, NIP2cL, and NIP2cS gene, 8) a non-wild type level of a NIP2b, NIP2cL, and NIP2cS-protein, 9) allelic loss of a NIP2b, NIP2cL, and NIP2cS gene, and 10) inappropriate post-translational modification of a NIP2b, NIP2cL, and NIP2cS-protein. As described herein, there are a large number of assays known in the art which can be used for detecting alterations in a NIP2b, NIP2cL, and NIP2cS gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the NIP2b, NIP2cL, and NIP2cS-gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a NIP2b, NIP2cL, and NIP2cS gene under conditions such that hybridization and amplification of the NIP2b, NIP2cL, and NIP2cS-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NIP2b, NIP2cL, and NIP2cS gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in NIP2b, NIP2cL, and NIP2cS can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in NIP2b, NIP2cL, and NIP2cS can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NIP2b, NIP2cL, and NIP2cS gene and detect mutations by comparing the sequence of the sample NIP2b, NIP2cL, and NIP2cS with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the NIP2b, NIP2cL, and NIP2cS gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type NIP2b, NIP2cL, and NIP2cS sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NIP2b, NIP2cL, and NIP2cS cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a NIP2b, NIP2cL, and NIP2cS sequence, e.g., a wild-type NIP2b, NIP2cL, and NIP2cS sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in NIP2b, NIP2cL, and NIP2cS genes. For example, single strand conformation polymorphism (SSCP) may be used to detect differences in electrophoretic mobility between mutant and wild type nucleic acids (orita et al. (1989) *Proc Natl. Acad.*

*Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control NIP2b, NIP2cL, and NIP2cS nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a NIP2b, NIP2cL, and NIP2cS gene.

Furthermore, any cell type or tissue in which NIP2b, NIP2cL, and NIP2cS is expressed may be utilized in the prognostic assays described herein.

3. Monitoring of Effects During Clinical Trials

Monitoring the influence of agents (e.g., drugs) on the expression or activity of a NIP2b, NIP2cL, and NIP2cS protein (e.g., the modulation of cellular programmed cell death) can be applied not only in basic drug screening, but also in clinical trials. For example, the effectiveness of an agent determined by a screening assay as described herein to increase NIP2b, NIP2cL, and NIP2cS gene expression, protein levels, or upregulate NIP2b, NIP2cL, and NIP2cS activity, can be monitored in clinical trials of subjects exhibiting decreased NIP2b, NIP2cL, and NIP2cS gene expression, protein levels, or dowrregulated NIP2b, NIP2cL, and NIP2cS activity. Alternatively, the effectiveness of an agent determined by a screening assay to decrease NIP2b, NIP2cL, and NIP2cS gene expression, protein levels, or downregulate NIP2b, NIP2cL, and NIP2cS activity, can be monitored in clinical trials of subjects exhibiting increased NIP2b, NIP2cL, and NIP2cS gene expression, protein levels, or upregulated NIP2b, NIP2cL, and NIP2cS activity. In such clinical trials, the expression or activity of a NIP2b, NIP2cL, and NIP2cS gene, and preferably, other genes that have been implicated in, for example, a NIP2b, NIP2cL, and NIP2cS-associated disorder can be used as a "read out" or markers of the phenotype of a particular cell.

For example, and not by way of limitation, genes, including NIP2b, NIP2cL, and NIP2cS, tat are modulated in cells by treatment with an agent (e.g., compound, drug or small molecule) which modulates NIP2b, NIP2cL, and NIP2cS activity (e.g., identified in a screening assay as described herein) can be identified. Thus, to study the effect of agents on NIP2b, NIP2cL, and NIP2cS-associated disorders (e.g., disorders characterized by deregulated programmed cell death), for example, in a clinical trial, cells can be isolated and RNA prepared and analyzed for the levels of expression of NIP2b, NIP2cL, and NIP2cS and other genes implicated in the NIP2b, NIP2cL, and NIP2cS-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of NIP2b, NIP2cL, and NIP2cS or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a NIP2b, NIP2cL, and NIP2cS protein, mRNA, or genomic DNA in the preadministration sample; (iii) obtaining one or more post-administration samples from the subject; (iv) detecting the level of expression or activity of the NIP2b, NIP2cL, and NIP2cS protein, mRNA, or genomic DNA in the post-administration samples; (v) comparing the level of expression or activity of the NIP2b, NIP2cL, and NIP2cS protein, mRNA, or genomic DNA in the pre-administration sample with the NIP2b, NIP2cL, and NIP2cS protein, mRNA, or genomic DNA in the post administration sample or samples; and (vi) altering the administration of the agent to the subject accordingly. For example, increased administration of the agent may be desirable to increase the expression or activity of NIP2b, NIP2cL, and NIP2cS to higher levels than detected, i.e., to increase the effectiveness of the agent. Alternatively, decreased administration of the agent may be desirable to decrease expression or activity of NIP2b, NIP2cL, and NIP2cS to lower levels than detected, i.e. to decrease the effectiveness of the agent. According to such an embodiment, NIP2b, NIP2cL, and NIP2cS expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant NIP2b, NIP2cL, and NIP2cS expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the NIP2b, NIP2cL, and NIP2cS molecules of the present invention or NIP2b, NIP2cL, and NIP2cS modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant NIP2b, NIP2cL, and NIP2cS expression or activity, by administering to the subject a NIP2b, NIP2cL, and NIP2cS or an agent which modulates NIP2b, NIP2cL, and NIP2cS expression or at least one NIP2b, NIP2cL, and NIP2cS activity. Subjects at risk for a disease which is caused or contributed to by aberrant NIP2b, NIP2cL, and NIP2cS expression or activity can be identified by, for example, any or a combination of diagnostic or prognostic assays as described herein. Administration of a prophylactic agent can occur prior to the manifestation of symptoms characteristic of the NIP2b, NIP2cL, and NIP2cS aberrancy, such that a disease or disorder is prevented or, alternatively, delayed in its progression. Depending on the type of NIP2b, NIP2cL, and NIP2cS aberrancy, for example, a NIP2b, NIP2cL, and NIP2cS, NIP2b, NIP2cL, and NIP2cS agonist or NIP2b, NIP2cL, and NIP2cS antagonist agent can be used for treating the subject. The appropriate agent can be determined based on screening assays described herein.

2. Therapeutic Methods

Another aspect of the invention pertains to methods of modulating NIP2b, NIP2cL, and NIP2cS expression or activity for therapeutic purposes. Accordingly, in an exemplary embodiment, the modulatory method of the invention involves contacting a cell with a NIP2b, NIP2cL, and NIP2cS or agent that modulates one or more of the activities of NIP2b, NIP2cL, and NIP2cS protein activity associated with the cell. An agent that modulates NIP2b, NIP2cL, and NIP2cS protein activity can be an agent as described herein, such as a nucleic acid or a protein, a naturally-occurring target molecule of a NIP2b, NIP2cL, and NIP2cS protein (e.g., a NIP2b, NIP2cL, and NIP2cS substrate), a NIP2b, NIP2cL, and NIP2cS antibody, a NIP2b, NIP2cL, and NIP2cS agonist or antagonist, a peptidomimetic of a NIP2b, NIP2cL, and NIP2cS agonist or antagonist, or other small molecule. In one embodiment, the agent stimulates one or more NIP2b, NIP2cL, and NIP2cS activities. Examples of such stimulatory agents include active NIP2b, NIP2cL, and NIP2cS protein and a nucleic acid molecule encoding NIP2b, NIP2cL, and NIP2cS that has been introduced into the cell. In another embodiment, the agent inhibits one or more NIP2b, NIP2cL, and NIP2cS activities. Examples of such inhibitory agents include antisense NIP2b, NIP2cL, and NIP2cS nucleic acid molecules, anti-NIP2b, NIP2cL, and NIP2cS antibodies, and NIP2b, NIP2cL, and NIP2cS inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NIP2b, NIP2cL, and NIP2cS protein or nucleic acid molecule. In one embodiment, the method involves administering an agent (e.g., an agent identified by a screening assay described herein), or combination of agents that modulates (e.g., upregulates or downregulates) NIP2b, NIP2cL, and NIP2cS expression or activity. In another embodiment, the method involves administering a NIP2b, NIP2cL, and NIP2cS protein or nucleic acid molecule as therapy to compensate for reduced or aberrant NIP2b, NIP2cL, and NIP2cS expression or activity.

Stimulation of NIP2b, NIP2cL, and NIP2cS activity is desirable in situations in which NIP2b, NIP2cL, and NIP2cS is abnormally downregulated and/or in which increased NIP2b, NIP2cL, and NIP2cS activity is likely to have a beneficial effect For example, stimulation of NIP2b, NIP2cL, and NIP2cS activity is desirable in situations in which a NIP2b, NIP2cL, and NIP2cS is downregulated and/or in which increased NIP2b, NIP2cL, and NIP2cS activity is likely to have a beneficial effect. Likewise, inhibition of NIP2b, NIP2cL, and NIP2cS activity is desirable in situations in which NIP2b, NIP2cL, and NIP2cS is abnormally upregulated and/or in which decreased NIP2b, NIP2cL, and NIP2cS activity is likely to have a beneficial effect.

3. Pharmacogenomics

The NIP2b, NIP2cL, and NIP2cS molecules of the present invention, as well as agents, or modulators which have a stimulatory or inhibitory effect on NIP2b, NIP2cL, and NIP2cS activity (e.g., NIP2b, NIP2cL, and NIP2cS gene expression) as identified by a screening assay described herein can be administered to individuals to treat (prophylactically or therapeutically) NIP2b, NIP2cL, and NIP2cS-associated disorders (e.g., programmed cell death associated disorders) associated with aberrant NIP2b, NIP2cL, and NIP2cS activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a NIP2b, NIP2cL, and NIP2cS molecule or NIP2b, NIP2cL, and NIP2cS modulator as well as tailoring the dosage and/or therapeutic regimen of treatment with a NIP2b, NIP2cL, and NIP2cS molecule or NIP2b, NIP2cL, and NIP2cS modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a NIP2b, NIP2cL, and NIP2cS protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a NIP2b, NIP2cL, and NIP2cS molecule or NIP2b, NIP2cL, and NIP2cS modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a NIP2b, NIP2cL, and NIP2cS molecule or NIP2b, NIP2cL, and NIP2cS modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of NIP2b, NIP2cL, and NIP2cS cDNA

In this example, the identification and characterization of the genes encoding human NIP2b, NIP2cL, and NIP2cS is described.

Isolation of the Human NIP2b, NIP2cL, and NIP2cS cDNA

The invention is based, at least in part, on the discovery of two human genes encoding two novel proteins, referred to herein as NIP2b and NIP2c (the long isoform:NIP2cL, and the short isoform:NIP2cS). A clone was originally identified from a monkey brain library, based on sequence homology to NIP2 proteins. Based on the sequence of this first clone, primers were designed and used to screen a human brain library (obtained from Clonetech). Two positive human clones were identified. The entire sequence of the two human clones was determined and found to contain open reading frames termed human "NIP2b", "NIP2cL", and "NIP2cS."

The nucleotide sequence encoding the human NIP2b protein is shown in FIG. 1 and is set forth as SEQ ID NO:1.

The full length protein encoded by this nucleic acid comprises about 371 amino acids and has the amino acid sequence shown in FIG. 1 and set forth as SEQ ID NO:2. The coding region (open reading frame) of SEQ ID NO:1 is set forth as SEQ ID NO:3.

The nucleotide sequence encoding the human NIP2cL protein is shown in FIG. 2 and is set forth as SEQ ID NO:4. The full length protein encoded by this nucleic acid comprises about 322 amino acids and has the amino acid sequence shown in FIG. 2 and set forth as SEQ ID NO:5. The coding region (open reading frame) of SEQ ID NO:4 is set forth as SEQ ID NO:6.

The nucleotide sequence encoding the human NIP2cS protein is shown in FIG. 3 and is set forth as SEQ ID NO:7. The full length protein encoded by this nucleic acid comprises about 126 amino acids and has the amino acid sequence shown in FIG. 3 and set forth as SEQ ID NO:8. The coding region (open reading frame) of SEQ ID NO:7 is set forth as SEQ ID NO:9.

Analysis of the Human NIP2b, NIP2cL, and NIP2cS Molecules

A BLASTX 1.4 search, using a score of 100 and a word length of 3 (Altschul et al. (1990) *J. Mol. Biol.* 215:403) of the translated nucleotide sequence of human NIP2b revealed that human NIP2b is similar to the Mus Musculus NIP2 protein (Accession Number AF035207) and the human BCL2/adenovirus E1B 19 kD-interacting protein 2 (Accession Number U15173). The human NIP2b protein is 66% identical to the Mus Musculus NIP2 protein (Accession Number AF035207) over translated nucleotides 787 to 1338 and 68% identical to the human BCL2/adenovirus E1B 19 kD-interacting protein 2 (Accession Number U15173) over translated nucleotides 787 to 1317.

A BLASTN 1.4.9 search, using a score of 100 and a word length of 12 (Altschul et al. (1990) *J. Mol. Biol.* 215:403) of the nucleotide sequence of human NIP2b revealed that NIP2b is similar to the Human mRNA for KIAA0367 (Accession Number AB002365). The NIP2b nucleic acid molecule is 74% identical to the Human mRNA for KIAA0367 (Accession Number AB002365) over nucleotides 793 to 1059.

A BLASTX 1.4 search, using a score of 100 and a word length of 3 (Altschul et al. (1990) *J. Mol. Biol.* 215:403) of the translated nucleotide sequence of human NIP2cL revealed that human NIP2cL is similar to the human KIAA0367 (Accession Number AB002365), the human BCL2/adenovirus E1B 19 kD-interacting protein 2 (Accession Number U15173), and the Mus Musculus NIP2 protein (Accession Number AF035207). The human NIP2cL protein is 99% identical to the human KIAA0367 (Accession Number AB002365) over translated nucleotides 50 to 520, 64% identical to the human BCL2/adenovirus E1B 19 kD-interacting protein 2 (Accession Number U15173) over translated nucleotides 557 to 985, and 64% identical to the Mus Musculus NIP2 protein (Accession Number AF035207) over translated nucleotides 557 to 955.

A BLASTN 1.4.9 search, using a score of 100 and a word length of 12 (Altschul et al. (1990) *J. Mol. Biol.* 215:403) of the nucleotide sequence of human NIP2cL revealed that NIP2cL is similar to the Human mRNA for KIAA0367 (Accession Number AB002365). The NIP2cL nucleic acid molecule is 100% identical to the Human mRNA for KIAA0367 (Accession Number AB002365) over nucleotides 960 to 4184, 98% identical over nucleotides 16 to 544, 95% identical over nucleotides 709 to 982, and 99% identical over nucleotides 538 to 716.

A BLASTX 1.4 search, using a score of 100 and a word length of 3 (Altschul et al. (1990) *J. Mol. Biol.* 215:403) of the translated nucleotide sequence of human NIP2cS revealed that human NIP2cS is similar to the human KIAA0367 (Accession Number AB002365), and the human BCL2/adenovirus E1B 19 kD-interacting protein 2 (Accession Number U15173). The human NIP2cS protein is 100% identical to the human KIAA0367 (Accession Number AB002365) over translated nucleotides 125 to 403 and 36% identical to the human BCL2/adenovirus E1B 19 kD-interacting protein 2 (Accession Number U15173) over translated nucleotides 134 to 316.

A BLASTN 1.4.9 search, using a score of 100 and a word length of 12 (Altschul et al. (1990) *J. Mol. Biol.* 215:403) of the nucleotide sequence of human NIP2cS revealed that NIP2cS is similar to the human cDNA clone IMAGE:1405422 (Accession Number AA843788). The NIP2cS nucleic acid molecule is 100% identical to the human cDNA clone IMAGE:1405422 (Accession Number AA843788) over nucleotides 598 to 1058.

The NIP2b protein was aligned with the human Bcl-2/adenovirus E1B 19 kDa-interacting protein 2 (BNIP-2, Accession Number U15173) using the GAP program in the GCG software package (Blossom 62 matrix) and a gap weight of 12 and a length weight of 4. The results showed a 56.051% identity and 67.197% similarity between the two sequences (see FIG. 10).

The NIP2b protein was also aligned with the NIP2cL protein using the GAP program in the GCG software package (Blossom 62 matrix) and a gap weight of 12 and a length weight of 4. The results showed a 58.805% identity and 69.182% similarity between the two sequences (see FIG. 11).

The NIP2cL protein was also aligned with the human Bcl-2/adenovirus E1B 19 kDa-interacting protein 2 (BNIP-2, Accession Number U15173) using the GAP program in the GCG software package (Blossom 62 matrix) and a gap weight of 12 and a length weight of 4. The results showed a 57.705% identity and 67.541% similarity between the two sequences (see FIG. 12).

Tissue Distribution of NIP2b, NIP2cL, and NIP2cS mRNA

This Example describes the tissue distribution of NIP2b, NIP2cL, and NIP2cS mRNA, as determined by Northern blot hybridization and in situ hybridization.

Northern blot hybridizations with the various RNA samples were performed under standard conditions and washed under stringent conditions, i.e., 0.2×SSC at 65° C. The DNA probe was radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations.

For in situ analysis, various tissues obtained from rat and monkey brains were first frozen on dry ice. Ten-micrometer-thick coronal sections of the tissues were postfixed with 4% formaldehyde in DEPC treated 1×phosphate-buffered saline at room temperature for 10 minutes before being rinsed twice in DEPC 1×phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type XI, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

A 5 kb NIP2b transcript is predominantly expressed in the brain, but on longer exposures this transcript can also be detected in prostate and small intestine. An additional 4 kb transcript can also be detected in the heart and skeletal muscle on longer exposures. Within the brain, NIP2b is expressed in most regions. The following areas give a particularly strong signal: cortex, amygdala, striatum, hippocampus, substantia nigra, corpus callosum, cerebellum (Purkinje cells), striatum, basal forebrain, lateral eniculate nucleus, and facial nucleus (motor neurons).

The NIP2cL transcript is predominantly expressed in the brain, but can also be detected in the prostate, colon and small intestine. On longer exposures, this transcript can also be detected in the heart, placenta, kidney, pancreas, spleen, testes, ovary and skeletal muscle. In addition, numerous other small transcripts can be seen on longer exposures. Within the brain, NIP2cL is expressed in the following regions: cortex, amygdala, cerebellum (granule cells), hippocampus (dentate gyrus and hippocampal pyramidal cells), striatum, thalamus, locus coeruleus, lateral geniculate nucleus, and facial nucleus (motor neurons).

The NIP2cS transcript is predominantly expressed in the heart, skeletal muscle, and brain.

Example 2

Expression of Recombinant NIP2b, NIP2cL, and NIP2cS Protein in Bacterial Cells

In this example, NIP2b, NIP2cL, and NIP2cS is expressed as a recombinant glutathione-S-transferase (GST) fusion polypeptide in E. coli and the fusion polypeptide is isolated and characterized. Specifically, NIP2b, NIP2cL, and NIP2cS is fused to GST and this fusion polypeptide is expressed in E. coli, e.g., strain PEB199. Expression of the GST-NIP2b, NIP2cL, and NIP2cS fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant NIP2b, NIP2cL, and NIP2cS Protein in COS Cells

To express the NIP2b, NIP2cL, and NIP2cS gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire NIP2b, NIP2cL, and NIP2cS protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the NIP2b, NIP2cL, and NIP2cS DNA sequence is amplified by PCR using two primers. The 5' primer contains the restriction site of interest followed by approximately twenty nucleotides of the NIP2b, NIP2cL, and NIP2cS coding sequence starting from the initiation codon; the 3' end sequence contains complementary sequences to the other restriction site of interest, a translation stop codon, the HA tag or FLAG tag and the last 20 nucleotides of the NIP2b, NIP2cL, and NIP2cS coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the NIP2b, NIP2cL, and NIP2cS gene is inserted in the correct orientation. The ligation mixture is transformed into E. coli cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the NIP2b, NIP2cL, and NIP2cS-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed, Cold Spring Harbor Laboratory, Cold Spring Harbor Laboratory Press, Cold Spring Harbor, N.Y., 1989. The expression of the NIP2b, NIP2cL, and NIP2cS polypeptide is detected by radiolabelling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the NIP2b, NIP2cL, and NIP2cS coding sequence is cloned directly into the polylinker of the pcDNA/Amp vector using the appropriate restriction sites. The resulting plasmid is transfected into COS cells in the manner described above, and the expression of the NIP2b, NIP2cL, and NIP2cS polypeptide is detected by radiolabelling and immunoprecipitation using a NIP2b, NIP2cL, and NIP2cS specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising the nucleotide sequence set forth in SEQ ID NO:1 or a full complement thereof.

2. An isolated nucleic acid molecule comprising a nucleotide sequence which encodes a polypeptide comprising the amino acid sequence set forth in SEQ ID NO: 2, or a full complement thereof.

3. An isolated nucleic acid molecule comprising a nucleotide sequence which encodes a naturally occurring allelic variant of a polypeptide comprising the amino acid sequence set forth in SEQ ID NO: 2, wherein the nucleic acid molecule hybridizes to the complement of a nucleic acid molecule consisting of SEQ ID NO:1 or 3 in 6×SSC at 45° C., followed by one or more washes in 0.2×SSC, 0.1% SDS at 50–65° C.

4. An isolated nucleic acid molecule comprising a nucleotide sequence which is at least 59% identical to the full length of the nucleotide sequence of SEQ ID NO:1, 3, 4, 6, 7, or 9, or a full complement thereof.

5. An isolated nucleic acid molecule comprising the nucleotide sequence set forth in SEQ ID NO:3, or a full complement thereof.

6. An isolated nucleic acid molecule comprising the nucleotide sequence set forth in SEQ ID NO:4, or a full complement thereof.

7. An isolated nucleic acid molecule comprising the nucleotide sequence set forth in SEQ ID NO:6, or a full complement thereof.

8. An isolated nucleic acid molecule comprising the nucleotide sequence set forth in SEQ ID NO:7, or a full complement thereof.

9. An isolated nucleic acid molecule comprising the nucleotide sequence set forth in SEQ ID NO:9, or a full complement thereof.

10. An isolated nucleic acid molecule comprising a nucleotide sequence which encodes a polypeptide comprising the amino acid sequence set forth in SEQ ID NO:5, or a full complement thereof.

11. An isolated nucleic acid molecule comprising a nucleotide sequence which encodes a polypeptide comprising the amino acid sequence set forth in SEQ ID NO: 8, or a full complement thereof.

12. An isolated nucleic acid molecule comprising a nucleotide sequence which encodes a naturally occurring allelic variant of a polypeptide comprising the amino acid sequence set forth in SEQ ID NO:5, wherein the nucleic acid molecule hybridizes to the complement of a nucleic acid molecule consisting of SEQ ID NO:4 or 6 in 6×SSC at 45° C., followed by one or more washes in 0.2×SSC, 0.1% SDS at 50–65° C.

13. An isolated nucleic acid molecule comprising a nucleotide sequence which encodes a naturally occurring allelic variant of a polypeptide comprising the amino acid sequence set forth in SEQ ID NO:8, wherein the nucleic acid molecule hybridizes to the complement of a nucleic acid molecule consisting of SEQ ID NO:7 or 9 in 6×SSC at 45° C., followed by one or more washes in 0.2×SSC, 0.1% SDS at 50–65° C.

14. An isolated nucleic acid molecule comprising a fragment of at least 461 nucleotides of a nucleic acid comprising the nucleotide sequence of SEQ ID NO:1, 3, 4, 6, 7, or 9, or a full complement thereof.

15. An isolated nucleic acid molecule comprising a nucleotide sequence which encodes a polypeptide comprising an amino acid sequence at leat about 60% identical to the full length of the acid sequence of SEQ ID NO:2, 5, or 8, or a full complement thereof.

16. An isolated nucleic acid molecule comprising a nucleotide sequence which encodes a fragment of a polypeptide comprising the amino acid sequence of SEQ ID NO:2, 5, or 8, wherein the fragment comprises at least 25 contiguous amino acid residues of the amino acid sequence of SEQ ID NO:2, 5, or 8, or a full complement thereof.

17. An isolated nucleic acid molecule comprising a nucleotide sequence which encodes a fragment of a polypeptide comprising the amino acid sequence of SEQ ID NO:2, 5, or 8, wherein the fragment comprises at least 50 contiguous amino acid residues of the amino acid sequence of SEQ ID NO:2, 5, or 8, or a full complement thereof.

18. An isolated nucleic acid molecule comprising a nucleotide sequence which encodes a fragment of a polypeptide comprising the amino acid sequence of SEQ ID NO:2, 5, or 8, wherein the fragment comprises at least 100 contiguous amino acid residues of the amino acid sequence of SEQ ID NO:2, 5, or 8, or a full complement thereof.

19. An isolated nucleic acid molecule comprising the nucleic acid molecule of any one of claims 1, 2, 3, 4, 5, 6, 7, 8, 9, 10, 11, 12, 13, 14, 15, 16, 17, or 18 operatively linked to a nucleotide sequence encoding a heterologons polypeptide, wherein said isolated nucleic acid molecule encodes a fusion polypeptide.

20. A vector comprising the nucleic acid molecule of any one of claims 1, 2, 3, 4, 5, 6, 7, 8, 9, 10, 11, 12, 13, 14, 15, 16, 17, or 18.

21. The vector of claim 20, which is an expression vector.

22. A recombinant host cell comprising the nucleic acid molecule of any one of claims 1, 2, 3, 4, 5, 6, 7, 8, 9, 10, 11, 12, 13, 14, 15, 16, 17, or 18 operatively linked to a recombinant regulatory sequence.

23. A method of producing a polypeptide comprising culturing the host cell of claim 22 under suitable conditions to, thereby, produce the polypeptide.

24. A method of expressing a polypeptide comprising the step of culturing the host cell of claim 22 under conditions in which the nucleic acid molecule is expressed, thereby expressing the polypeptide.

* * * * *

SEQUENCE LISTING

<160> NUMBER OF SEQ ID NOS: 9

<210> SEQ ID NO 1
<211> LENGTH: 3076
<212> TYPE: DNA
<213> ORGANISM: Homo sapiens
<220> FEATURE:
<221> NAME/KEY: CDS
<222> LOCATION: (370)..(1482)

<400> SEQUENCE: 1

```
ccacgcgtcc gcccacgcgt ccgggaagaa gcagctacct cggaggcagg gcgcgcaggc        60
gggcggcgat gagagggggc gcagccgcag ccccgcgctg gggagcccac cgctaaccct       120
gcaccccacc caccccctgca caaaagagct ggcgggcgct ggccacgtcg ccctgggtga      180
ccttcctcgg atgcagaatc cgcccctgcg agcatcctct tcctcctagg ctctgaaggc      240
ccggggagcg tgagcgatgc ccagctgcac ccgggcaggg ctcgcctttg tttgccagta      300
aggaggagag gctgtctcag ctgcagaggg gtcatccctg cttcaagcca gtgcctcttc      360 ccagctccc atg ggg acc acc gaa gcc acg ctc cgg atg gaa aac gtg gac      411
           Met Gly Thr Thr Glu Ala Thr Leu Arg Met Glu Asn Val Asp
             1               5                  10 gtg aag gag gaa tgg cag gac gaa gat ctt ccc agg cca ctc cca gaa        459
Val Lys Glu Glu Trp Gln Asp Glu Asp Leu Pro Arg Pro Leu Pro Glu
 15                  20                  25                  30 gag acg ggg gtg gaa ctg ctt ggc agc ccg gtg gaa gac aca tcc tct        507
Glu Thr Gly Val Glu Leu Leu Gly Ser Pro Val Glu Asp Thr Ser Ser
                 35                  40                  45 cct ccc aac acg cta aat ttc aac gga gcg cat cgt aag agg aag acg        555
Pro Pro Asn Thr Leu Asn Phe Asn Gly Ala His Arg Lys Arg Lys Thr
             50                  55                  60 ctg gtg gcc cca gag atc aac att tct ctg gat cag agt gag ggg tcc        603
Leu Val Ala Pro Glu Ile Asn Ile Ser Leu Asp Gln Ser Glu Gly Ser
         65                  70                  75 ctg ctg tcc gat gac ttc ttg gat acc cct gat gac ctg gat att aac        651
Leu Leu Ser Asp Asp Phe Leu Asp Thr Pro Asp Asp Leu Asp Ile Asn
     80                  85                  90 gtg gat gac atc gag acc ccc gat gag acc gac tcg ctg gag ttc ctg        699
Val Asp Asp Ile Glu Thr Pro Asp Glu Thr Asp Ser Leu Glu Phe Leu
 95                 100                 105                 110 ggg aat ggc aac gaa ctg gag tgg gaa gac gac acc ccc gtg gcc acc        747
Gly Asn Gly Asn Glu Leu Glu Trp Glu Asp Asp Thr Pro Val Ala Thr
                115                 120                 125 gcc aag aac atg ccc ggg gac agc gcg gat cta ttt ggg gac ggc acg        795
Ala Lys Asn Met Pro Gly Asp Ser Ala Asp Leu Phe Gly Asp Gly Thr
            130                 135                 140 acg gag gac ggc agc gcc gcc aac ggg cgc ctg tgg cgg aca gtg atc        843
Thr Glu Asp Gly Ser Ala Ala Asn Gly Arg Leu Trp Arg Thr Val Ile
        145                 150                 155 atc ggg gag caa gag cac cgt ata gac ctg cac atg atc cgg cct tac        891
Ile Gly Glu Gln Glu His Arg Ile Asp Leu His Met Ile Arg Pro Tyr
    160                 165                 170
```

```
atg aaa gtg gtc acc cac gga ggg tac tac ggc gaa ggc ctc aac gcc     939
Met Lys Val Val Thr His Gly Gly Tyr Tyr Gly Glu Gly Leu Asn Ala
175                 180                 185                 190 atc atc gtc ttc gca gcc tgc ttc ctt cca gac agc agc ctc ccc gac     987
Ile Ile Val Phe Ala Ala Cys Phe Leu Pro Asp Ser Ser Leu Pro Asp
                195                 200                 205 tac cac tac atc atg gag aac ctc ttc ctg tac gtc atc agc agc tta    1035
Tyr His Tyr Ile Met Glu Asn Leu Phe Leu Tyr Val Ile Ser Ser Leu
            210                 215                 220 gag ctc ctg gtg gct gag gac tac atg atc gtg tac ctg aac ggt gcc    1083
Glu Leu Leu Val Ala Glu Asp Tyr Met Ile Val Tyr Leu Asn Gly Ala
        225                 230                 235 acg ccc cgg cgg agg atg cct gga atc ggc tgg ctg aag aag tgc tac    1131
Thr Pro Arg Arg Arg Met Pro Gly Ile Gly Trp Leu Lys Lys Cys Tyr
240                 245                 250 cag atg atc gac cgg agg ttg cgg aaa aac ctg aag tcc ttg atc atc    1179
Gln Met Ile Asp Arg Arg Leu Arg Lys Asn Leu Lys Ser Leu Ile Ile
255                 260                 265                 270 gtc cac ccc tcg tgg ttc att cgg act gtg ctg gcc atc tct cgc cct    1227
Val His Pro Ser Trp Phe Ile Arg Thr Val Leu Ala Ile Ser Arg Pro
                275                 280                 285 ttc atc agc gtc aag ttc atc aac aag atc cag tac gtg cac agc ttg    1275
Phe Ile Ser Val Lys Phe Ile Asn Lys Ile Gln Tyr Val His Ser Leu
            290                 295                 300 gaa gac ctg gag caa ctc atc cct atg gaa cac gtc cag atc cca gac    1323
Glu Asp Leu Glu Gln Leu Ile Pro Met Glu His Val Gln Ile Pro Asp
        305                 310                 315 tgc gtc ctg caa tac gaa gag gaa aga ctg aag gcc agg agg gag agc    1371
Cys Val Leu Gln Tyr Glu Glu Glu Arg Leu Lys Ala Arg Arg Glu Ser
320                 325                 330 gcg agg ccc cag ccg gag ttt gtg ctg ccc agg tct gaa gag aag cca    1419
Ala Arg Pro Gln Pro Glu Phe Val Leu Pro Arg Ser Glu Glu Lys Pro
335                 340                 345                 350 gag gtg gca cca gtg gaa aac agg tct gct ctg gtc tca gaa gat cag    1467
Glu Val Ala Pro Val Glu Asn Arg Ser Ala Leu Val Ser Glu Asp Gln
                355                 360                 365 gaa aca agc atg tcc tgaggcgacg tgagcataac aaaggacatg gaagaagatt    1522
Glu Thr Ser Met Ser
            370 ccagatgcca gaaaacctct gtcagacgcc cactggcccc agatctcatc ctgcctcatc   1582 ctgagtccca atcttccaag ggtgccagcc cctccgttca tctctgaaac ccagcatcct   1642 tttcagctgc ttgaaaacat tgtatttttt tttttttaacg atgcagtatt tgtgcgttcc   1702 agaaaagggc ccagctctga gcccctcacc cttccacact cacgaactct cagccgagga   1762 aggcaagaag cgcagggggt ggcccgcgtg gcgtcggtgg cctccgctcc tgctcgcagc   1822 ccctgtggtc agagctggat acaagattca agacccttct cttgcttgtc acccgctcca   1882 ggttggagcc acagacaccc accgccaccc cggctgggtc tgcgtccttt cctgtgcctt   1942 tccctccaga atgcggcctc agacctagaa gctcaacccc cctatgaggg ccacgtcctg   2002 gggtagctcc tgacctccga ccttatgtcc aaatttcaca cccatggttt ttcatttgac   2062 ccgcccccctt ctcgctcata atgacaccca gctcctttga gaggatcaga gcccattgca   2122 caagaagagc cgctgccaac catccttgtc ctccgattgc aaaatgacac cccagtaatc   2182 tagaacattc tcaagcccct ttaactcaga tgtcaagcca ccgggcaaac cccgtcaata   2242 cctcccacca aggaatgaga tatgtggacc tcactgctcc cccaacccag cgtcaggctg   2302
```

-continued

```
ggacacgcca acgctgttcc gggttggaac agcacaggct cagaaactgg ctctgaaata    2362
ggcagaccta gcaagaggaa gatacagggt atcgggcgtt tgagtgtttc agaagtcatt    2422
cgggaagata atccagtgc gctggccgca gccacctgca ttcaaagctt ggaccagcgg    2482
gttcttgttc gggaggcaaa tttccctagg aaaaagaaga cagacttttc taatgggtc    2542 caaatgcgga tcactggtca gatggactct agaagcactg agctcccgt ctctggaagt    2602 atttaagaaa aggctgggcc aggcacgatg gctcacgcct gtaatcccag actttgggag    2662
gccgaggcag gcggatcacc tgaggtgagg agtttgagaa cagcctggcc aacatggtga    2722
aacctcatct ctactaaaaa tacaaaaatt agccaggcgt ggtggcaggt gcctgtaatc    2782
ccagctactt gggaggctga ggcatgagaa tcacttaaac ctgagaggca gaggttacag    2842
tgagccaaga tcgtgccact gcattccagc ctgggcgaca gagcaagact ctgtctcaaa    2902
aaaaataaaa aataatcagg gcacagtggc tcatgcctgt aatcccagca ctctgggagg    2962
ctgaggtggg tggatcacct gaggtcagga gttcaagacc agcctggtga acatggcgaa    3022
accccgtctc taataaaaat acaaaaatta gccgggcatg gtggtgcatg cctg          3076
```

<210> SEQ ID NO 2
<211> LENGTH: 371
<212> TYPE: PRT
<213> ORGANISM: Homo sapiens

<400> SEQUENCE: 2

```
Met Gly Thr Thr Glu Ala Thr Leu Arg Met Glu Asn Val Asp Val Lys
 1               5                  10                  15

Glu Glu Trp Gln Asp Glu Asp Leu Pro Arg Pro Leu Pro Glu Glu Thr
            20                  25                  30

Gly Val Glu Leu Leu Gly Ser Pro Val Glu Asp Thr Ser Ser Pro Pro
        35                  40                  45

Asn Thr Leu Asn Phe Asn Gly Ala His Arg Lys Arg Lys Thr Leu Val
    50                  55                  60

Ala Pro Glu Ile Asn Ile Ser Leu Asp Gln Ser Glu Gly Ser Leu Leu
65                  70                  75                  80

Ser Asp Asp Phe Leu Asp Thr Pro Asp Leu Asp Ile Asn Val Asp
                85                  90                  95

Asp Ile Glu Thr Pro Asp Glu Thr Asp Ser Leu Glu Phe Leu Gly Asn
            100                 105                 110

Gly Asn Glu Leu Glu Trp Glu Asp Asp Thr Pro Val Ala Thr Ala Lys
        115                 120                 125

Asn Met Pro Gly Asp Ser Ala Asp Leu Phe Gly Asp Gly Thr Thr Glu
    130                 135                 140

Asp Gly Ser Ala Ala Asn Gly Arg Leu Trp Arg Thr Val Ile Ile Gly
145                 150                 155                 160

Glu Gln Glu His Arg Ile Asp Leu His Met Ile Arg Pro Tyr Met Lys
                165                 170                 175

Val Val Thr His Gly Gly Tyr Tyr Gly Glu Gly Leu Asn Ala Ile Ile
            180                 185                 190

Val Phe Ala Ala Cys Phe Leu Pro Asp Ser Ser Leu Pro Asp Tyr His
        195                 200                 205

Tyr Ile Met Glu Asn Leu Phe Leu Tyr Val Ile Ser Ser Leu Glu Leu
    210                 215                 220

Leu Val Ala Glu Asp Tyr Met Ile Val Tyr Leu Asn Gly Ala Thr Pro
225                 230                 235                 240
```

-continued

```
Arg Arg Arg Met Pro Gly Ile Gly Trp Leu Lys Lys Cys Tyr Gln Met
            245                 250                 255
Ile Asp Arg Arg Leu Arg Lys Asn Leu Lys Ser Leu Ile Ile Val His
            260                 265                 270
Pro Ser Trp Phe Ile Arg Thr Val Leu Ala Ile Ser Arg Pro Phe Ile
            275                 280                 285
Ser Val Lys Phe Ile Asn Lys Ile Gln Tyr Val His Ser Leu Glu Asp
            290                 295                 300
Leu Glu Gln Leu Ile Pro Met Glu His Val Gln Ile Pro Asp Cys Val
305                 310                 315                 320
Leu Gln Tyr Glu Glu Arg Leu Lys Ala Arg Arg Glu Ser Ala Arg
            325                 330                 335
Pro Gln Pro Glu Phe Val Leu Pro Arg Ser Glu Glu Lys Pro Glu Val
            340                 345                 350
Ala Pro Val Glu Asn Arg Ser Ala Leu Val Ser Glu Asp Gln Glu Thr
            355                 360                 365
Ser Met Ser
    370
```

```
<210> SEQ ID NO 3
<211> LENGTH: 1113
<212> TYPE: DNA
<213> ORGANISM: Homo sapiens
<220> FEATURE:
<221> NAME/KEY: CDS
<222> LOCATION: (1)..(1113)

<400> SEQUENCE: 3
```

| | |
|---|---|
| atg ggg acc acc gaa gcc acg ctc cgg atg gaa aac gtg gac gtg aag<br>Met Gly Thr Thr Glu Ala Thr Leu Arg Met Glu Asn Val Asp Val Lys<br>1               5                   10                  15 | 48 |
| gag gaa tgg cag gac gaa gat ctt ccc agg cca ctc cca gaa gag acg<br>Glu Glu Trp Gln Asp Glu Asp Leu Pro Arg Pro Leu Pro Glu Glu Thr<br>                20                  25                  30 | 96 |
| ggg gtg gaa ctg ctt ggc agc ccg gtg gaa gac aca tcc tct cct ccc<br>Gly Val Glu Leu Leu Gly Ser Pro Val Glu Asp Thr Ser Ser Pro Pro<br>            35                  40                  45 | 144 |
| aac acg cta aat ttc aac gga gcg cat cgt aag agg aag acg ctg gtg<br>Asn Thr Leu Asn Phe Asn Gly Ala His Arg Lys Arg Lys Thr Leu Val<br>        50                  55                  60 | 192 |
| gcc cca gag atc aac att tct ctg gat cag agt gag ggg tcc ctg ctg<br>Ala Pro Glu Ile Asn Ile Ser Leu Asp Gln Ser Glu Gly Ser Leu Leu<br>65                  70                  75                  80 | 240 |
| tcc gat gac ttc ttg gat acc cct gat gac ctg gat att aac gtg gat<br>Ser Asp Asp Phe Leu Asp Thr Pro Asp Asp Leu Asp Ile Asn Val Asp<br>                85                  90                  95 | 288 |
| gac atc gag acc ccc gat gag acc gac tcg ctg gag ttc ctg ggg aat<br>Asp Ile Glu Thr Pro Asp Glu Thr Asp Ser Leu Glu Phe Leu Gly Asn<br>            100                 105                 110 | 336 |
| ggc aac gaa ctg gag tgg gaa gac gac acc ccc gtg gcc acc gcc aag<br>Gly Asn Glu Leu Glu Trp Glu Asp Asp Thr Pro Val Ala Thr Ala Lys<br>        115                 120                 125 | 384 |
| aac atg ccc ggg gac agc gcg gat cta ttt ggg gac ggc acg acg gag<br>Asn Met Pro Gly Asp Ser Ala Asp Leu Phe Gly Asp Gly Thr Thr Glu<br>    130                 135                 140 | 432 |
| gac ggc agc gcc gcc aac ggg cgc ctg tgg cgg aca gtg atc atc ggg<br>Asp Gly Ser Ala Ala Asn Gly Arg Leu Trp Arg Thr Val Ile Ile Gly<br>145                 150                 155                 160 | 480 |
| gag caa gag cac cgt ata gac ctg cac atg atc cgg cct tac atg aaa<br>Glu Gln Glu His Arg Ile Asp Leu His Met Ile Arg Pro Tyr Met Lys | 528 |

```
Glu Gln Glu His Arg Ile Asp Leu His Met Ile Arg Pro Tyr Met Lys
                165                 170                 175 gtg gtc acc cac gga ggg tac tac ggc gaa ggc ctc aac gcc atc atc         576
Val Val Thr His Gly Gly Tyr Tyr Gly Glu Gly Leu Asn Ala Ile Ile
            180                 185                 190 gtc ttc gca gcc tgc ttc ctt cca gac agc agc ctc ccc gac tac cac         624
Val Phe Ala Ala Cys Phe Leu Pro Asp Ser Ser Leu Pro Asp Tyr His
                195                 200                 205 tac atc atg gag aac ctc ttc ctg tac gtc atc agc agc tta gag ctc         672
Tyr Ile Met Glu Asn Leu Phe Leu Tyr Val Ile Ser Ser Leu Glu Leu
    210                 215                 220 ctg gtg gct gag gac tac atg atc gtg tac ctg aac ggt gcc acg ccc         720
Leu Val Ala Glu Asp Tyr Met Ile Val Tyr Leu Asn Gly Ala Thr Pro
225                 230                 235                 240 cgg cgg agg atg cct gga atc ggc tgg ctg aag aag tgc tac cag atg         768
Arg Arg Arg Met Pro Gly Ile Gly Trp Leu Lys Lys Cys Tyr Gln Met
                245                 250                 255 atc gac cgg agg ttg cgg aaa aac ctg aag tcc ttg atc atc gtc cac         816
Ile Asp Arg Arg Leu Arg Lys Asn Leu Lys Ser Leu Ile Ile Val His
                260                 265                 270 ccc tcg tgg ttc att cgg act gtg ctg gcc atc tct cgc cct ttc atc         864
Pro Ser Trp Phe Ile Arg Thr Val Leu Ala Ile Ser Arg Pro Phe Ile
            275                 280                 285 agc gtc aag ttc atc aac aag atc cag tac gtg cac agc ttg gaa gac         912
Ser Val Lys Phe Ile Asn Lys Ile Gln Tyr Val His Ser Leu Glu Asp
    290                 295                 300 ctg gag caa ctc atc cct atg gaa cac gtc cag atc cca gac tgc gtc         960
Leu Glu Gln Leu Ile Pro Met Glu His Val Gln Ile Pro Asp Cys Val
305                 310                 315                 320 ctg caa tac gaa gag gaa aga ctg aag gcc agg agg gag agc gcg agg        1008
Leu Gln Tyr Glu Glu Glu Arg Leu Lys Ala Arg Arg Glu Ser Ala Arg
                325                 330                 335 ccc cag ccg gag ttt gtg ctg ccc agg tct gaa gag aag cca gag gtg        1056
Pro Gln Pro Glu Phe Val Leu Pro Arg Ser Glu Glu Lys Pro Glu Val
                340                 345                 350 gca cca gtg gaa aac agg tct gct ctg gtc tca gaa gat cag gaa aca        1104
Ala Pro Val Glu Asn Arg Ser Ala Leu Val Ser Glu Asp Gln Glu Thr
            355                 360                 365 agc atg tcc                                                            1113
Ser Met Ser
    370

<210> SEQ ID NO 4
<211> LENGTH: 4235
<212> TYPE: DNA
<213> ORGANISM: Homo sapiens
<220> FEATURE:
<221> NAME/KEY: CDS
<222> LOCATION: (23)..(988)

<400> SEQUENCE: 4
gtcgacccac gcgtccgcgg aa atg gag gag gag aca gag ttc ctt gag ctc        52
                         Met Glu Glu Glu Thr Glu Phe Leu Glu Leu
                          1               5                  10 gga acc agg ata tca aga cca aat gga cta ctg tca gag gat gta gga       100
Gly Thr Arg Ile Ser Arg Pro Asn Gly Leu Leu Ser Glu Asp Val Gly
            15                  20                  25 atg gac atc ccc ttt gaa gag ggc gtg ctg agt ccc agt gct gca gac       148
Met Asp Ile Pro Phe Glu Glu Gly Val Leu Ser Pro Ser Ala Ala Asp
        30                  35                  40 atg agg cct gaa cct cct aat tct ctg gat ctt aat gac act cat cct       196
```

```
                                                                 -continued

Met Arg Pro Glu Pro Asn Ser Leu Asp Leu Asn Asp Thr His Pro
        45                  50                  55 cgg aga atc aag ctc aca gcc cca aat atc aat ctt tct ctg gac caa    244
Arg Arg Ile Lys Leu Thr Ala Pro Asn Ile Asn Leu Ser Leu Asp Gln
 60                  65                  70 agt gaa gga tct att ctc tct gat gat aac ttg gac agt cca gat gaa    292
Ser Glu Gly Ser Ile Leu Ser Asp Asp Asn Leu Asp Ser Pro Asp Glu
 75                  80                  85                  90 att gac atc aat gtg gat gaa ctt gat acc ccc gat gaa gca gat tct    340
Ile Asp Ile Asn Val Asp Glu Leu Asp Thr Pro Asp Glu Ala Asp Ser
                 95                 100                 105 ttt gag tac act ggc cat gat ccc aca gcc aac aaa gat tct ggc caa    388
Phe Glu Tyr Thr Gly His Asp Pro Thr Ala Asn Lys Asp Ser Gly Gln
            110                 115                 120 gag tca gag tct att cca gaa tat acg gcc gaa gag gaa cgg gag gac    436
Glu Ser Glu Ser Ile Pro Glu Tyr Thr Ala Glu Glu Glu Arg Glu Asp
        125                 130                 135 aac cgg ctt tgg atg aca gtg gtc att gga gaa caa gag cag cgc att    484
Asn Arg Leu Trp Met Thr Val Val Ile Gly Glu Gln Glu Gln Arg Ile
140                 145                 150 gac atg aag gtc atc gag ccc tac agg aga gtc att tct cac gga gga    532
Asp Met Lys Val Ile Glu Pro Tyr Arg Arg Val Ile Ser His Gly Gly
155                 160                 165                 170 gat tca gga tac tat ggg gac ggt cta aat gcc atc att gtg ttt gcc    580
Asp Ser Gly Tyr Tyr Gly Asp Gly Leu Asn Ala Ile Ile Val Phe Ala
                175                 180                 185 gcc tgt ttt ctg cca gac agc agt cgg gcg gat tac cac tat gtc atg    628
Ala Cys Phe Leu Pro Asp Ser Ser Arg Ala Asp Tyr His Tyr Val Met
            190                 195                 200 gaa aat ctt ttc cta tat gta ata agt act tta gag ttg atg gta gct    676
Glu Asn Leu Phe Leu Tyr Val Ile Ser Thr Leu Glu Leu Met Val Ala
        205                 210                 215 gaa gac tat atg att gtg tac ttg aat ggt gca acc cca aga agg agg    724
Glu Asp Tyr Met Ile Val Tyr Leu Asn Gly Ala Thr Pro Arg Arg Arg
220                 225                 230 atg cca ggg cta ggc tgg atg aag aaa tgc tac cag atg att gac aga    772
Met Pro Gly Leu Gly Trp Met Lys Lys Cys Tyr Gln Met Ile Asp Arg
235                 240                 245                 250 cgg ttg agg aag aat ttg aaa tca ttc atc att gtt cat cca tct tgg    820
Arg Leu Arg Lys Asn Leu Lys Ser Phe Ile Ile Val His Pro Ser Trp
                255                 260                 265 ttc atc aga aca atc ctt gct gtg aca cga cct ttt ata agt tca aaa    868
Phe Ile Arg Thr Ile Leu Ala Val Thr Arg Pro Phe Ile Ser Ser Lys
            270                 275                 280 ttc agc agt aaa att aaa tat gtc aat agc tta tca gaa ctc agt ggg    916
Phe Ser Ser Lys Ile Lys Tyr Val Asn Ser Leu Ser Glu Leu Ser Gly
        285                 290                 295 ctg atc cca atg gat tgc atc cac att cca gag agc atc atc aat att    964
Leu Ile Pro Met Asp Cys Ile His Ile Pro Glu Ser Ile Ile Asn Ile
300                 305                 310 gac ttg aag ctg aaa gaa aag cct tagttggcca tgctggaaga agaggatgct   1018
Asp Leu Lys Leu Lys Glu Lys Pro
315                 320 tttctggttc atggttctgt tgaaacatat ctacctgaaa gagacagggc tgatgttacc   1078
tttttccact ttgcactacc tggtgccatt ctaaatttct aaggggaaaa atagaaagtt   1138
tgtttactct taagatattt tatgaaattg tgtgtacttt cctatttgc caattatgtg    1198 cctcaaagat tttagttgag ccttagcaag aaagtaggac cttccatttc aatacttcat   1258
```

```
taacacggtg tagtgatact ttgtcccttA gactggtgtt taccagtaag ataccttTaa    1318
tccactgtta agtatgagtg gatttgtttc catagattag ctggatttcc ttttggtgat    1378
tgcattaggt ttaaagtaca caggtctcaa ctctccccag gaaagtttcc cctgtttgac    1438
tccacctttA aaatcctaag cctgactagg acagccacaa accacacaag gtgtaaaacc    1498
atcatcagct aagtgcccgt tttgttcttg tttaccagaa tctcctttaa cttctcaaag    1558
ggaagccggg ctttctaatc cacgtcaact ttattttagt tgtcaaattg ggcattatat    1618
tttatgtaaa ttggtctttt aacatcattt tcctgatgaa tgttggtgac caccacattg    1678
tgaaatttaa gaatccgtgt tgcatgtttg gtagctctct gagtttcagg ccataaactc    1738
agctccagag gttacctttt aagtgccaag aactcaagtg caaggtggcc tactcaaaaa    1798
tcatttggta gcattcagtt attcatgaat tcctctctcg catgcattat aaaaagtgat    1858
ctgctttaaa acaccgtaat ctgatcatag gcttaaaatt aaatatgagt attactttca    1918
tgtacaaaat atttccttta tagtcttcat atgcccttta aaatgccaac aagatttcaa    1978
gtctgtaggc ctctagtgag gtggggtggc aaaccacagc taagtctcgc tcaccactgc    2038
aagctaagaa tggttttac attttgggtt ggaaaaattt tttttgaata tttcatgaca     2098
catgaaaatt attcaaatgt tagtgccgat aaataaagtg gtactgaaac acagccacac    2158
aaacttgttt ttgtactgtc tacagctact ttcacactac agccgcagag ctgagcagtt    2218
cagcagaccg tatgtcccac aatgcctaaa acattgacta tgtttacaga aaaagtttgc    2278
tgaccCctgc tctagcaaac gcatcctttc ctactccacc ccaatttgta tttagatagt    2338
ttctctaaca gaacggacaa atgaggctgc aaactaattt attttttgtca aaaatcaatg   2398
ttttgacatc cacagacagt gaaataaaag aaatggcttg ctgaaaaaca tgaggagtcc    2458
tagccacaaa atcactgctt aggttgcaat tgccaaaatg aagccttctt agaagcactt    2518
ctttagtata tacaggtgtt ggctgaagtc cgtgcctcac tctgggaacc attcttagtc    2578
tccagtgtct cctattacaa agaagctggc agaaataaaa atgaagggGt gagagcggtt    2638
ccaccctagt ctcatggtgg aaaattcatt ggggagagct gtccaggata tttggagtcc    2698
tgggtagaag gagcttgtaa ctactttaaa gtcgacatct ttgcacaggt gattgagttt    2758
ctctgacctc attgcttcac ctctgtctcc tcccgtcctt ccgcacgtgc ccacacacac    2818
gcagttcagc cctctttcct ccataagcct ccatcgtttt ctcttttctc ctcttgatcc    2878
tttcaagcga gtatcttgtt gaattgtatg ttctgttgga tctcctcctt cataacatct    2938
ggcttgttgg acagaaaaac cctacagccc accccctccc acagcccacc tccactttTg   2998
aaagcccaaa ttacacctct cccagaacac agtgttgacg taaatacagt tacccaatat    3058
tcctgtttgt tcacctattt gctactttca ctcagtagca tcccattttg taaaatgaat    3118
tccatggtca ccctgtcaca ggaagtaatg aaaaatccag tgttcagtgt agtggtgcaa    3178
acctgagggc atagagctgt tcatagaggg ctcttgttat agccaaacag acacagcaac    3238
aatctcacca tttatatata tattTTtaac ttgtccagct catctatgga aaactactca    3298
ggtggtatgc tgtttgaagc ctcatcttcc tacatgaaaa ttatgggcat ttgtcccaat    3358
gattttgttt cagctgttct gtaggctgca taaccactct gatatttagg tatctgctat    3418
tttattatct taaaagacaa attaatttaa ttgcatgtgc tagggaaaag ctaccatgta    3478
cattcacccc aagtaaatag aatcctagat gaatcctaga aaaataatcc ctaagcagat    3538
aggtagacag aggtaaacat tcacatgatt tagctctcta gctcttgcac tctgaacatt    3598
cttgctttgg ttctgacttc tgggaactgc tttgcatttc tcctatagat ctgtagttaa    3658
```

```
gggaaccaag gggtcattgg ggcaaaagca ttgtttctca aagctccttg attaagagaa      3718
agaacagaaa tttgcacaga agatagtgtc aaggagtgag aaagtttgtt tgagggcagt      3778
agctcagtgt ggaagaaaat cctgaagttt ctgttgaagc catacaatgt tctatggggt      3838
tactctctaa gacattctct gaggtgtgtg aggaagtcac tactcctagc ctttgttaag      3898
atgtaatttt aaatattcag ttatggtact atgtttgcaa ctctcgtctt atcacaatgc      3958
ctcagtagtt tgttcccta  gaaacattta gatgtgcaca aattaatctt ttatatatct      4018
aaaggttttt ctatcatgca ttggattgct cagaataaag tgtctgttag acttcgtttt      4078
ggtaaataaa ttctccataa tgtagattaa taatataaaa gtctttaatg acacaatata      4138
tctatatagc ctcactgtat aattcagaaa taaaaattga ttctgcaaaa aaaaaaaaa       4198 aaaaaaaaaa aaaaaaaaa  aaaaaagggg cggccgc                              4235
```

<210> SEQ ID NO 5
<211> LENGTH: 322
<212> TYPE: PRT
<213> ORGANISM: Homo sapiens

<400> SEQUENCE: 5

```
Met Glu Glu Glu Thr Glu Phe Leu Glu Leu Gly Thr Arg Ile Ser Arg
 1               5                  10                  15

Pro Asn Gly Leu Leu Ser Glu Asp Val Gly Met Asp Ile Pro Phe Glu
                20                  25                  30

Glu Gly Val Leu Ser Pro Ser Ala Ala Asp Met Arg Pro Glu Pro Pro
            35                  40                  45

Asn Ser Leu Asp Leu Asn Asp Thr His Pro Arg Arg Ile Lys Leu Thr
        50                  55                  60

Ala Pro Asn Ile Asn Leu Ser Leu Asp Gln Ser Glu Gly Ser Ile Leu
    65                  70                  75                  80

Ser Asp Asp Asn Leu Asp Ser Pro Asp Glu Ile Asp Ile Asn Val Asp
                85                  90                  95

Glu Leu Asp Thr Pro Asp Glu Ala Asp Ser Phe Glu Tyr Thr Gly His
            100                 105                 110

Asp Pro Thr Ala Asn Lys Asp Ser Gly Gln Glu Ser Glu Ser Ile Pro
        115                 120                 125

Glu Tyr Thr Ala Glu Glu Arg Glu Asp Asn Arg Leu Trp Met Thr
    130                 135                 140

Val Val Ile Gly Glu Gln Glu Gln Arg Ile Asp Met Lys Val Ile Glu
145                 150                 155                 160

Pro Tyr Arg Arg Val Ile Ser His Gly Gly Asp Ser Gly Tyr Tyr Gly
                165                 170                 175

Asp Gly Leu Asn Ala Ile Ile Val Phe Ala Ala Cys Phe Leu Pro Asp
            180                 185                 190

Ser Ser Arg Ala Asp Tyr His Tyr Val Met Glu Asn Leu Phe Leu Tyr
        195                 200                 205

Val Ile Ser Thr Leu Glu Leu Met Val Ala Glu Asp Tyr Met Ile Val
    210                 215                 220

Tyr Leu Asn Gly Ala Thr Pro Arg Arg Met Pro Gly Leu Gly Trp
225                 230                 235                 240

Met Lys Lys Cys Tyr Gln Met Ile Asp Arg Arg Leu Arg Lys Asn Leu
                245                 250                 255

Lys Ser Phe Ile Ile Val His Pro Ser Trp Phe Ile Arg Thr Ile Leu
            260                 265                 270
```

-continued

```
Ala Val Thr Arg Pro Phe Ile Ser Ser Lys Phe Ser Ser Lys Ile Lys
            275                 280                 285

Tyr Val Asn Ser Leu Ser Glu Leu Ser Gly Leu Ile Pro Met Asp Cys
        290                 295                 300

Ile His Ile Pro Glu Ser Ile Ile Asn Ile Asp Leu Lys Leu Lys Glu
305                 310                 315                 320

Lys Pro

<210> SEQ ID NO 6
<211> LENGTH: 966
<212> TYPE: DNA
<213> ORGANISM: Homo sapiens
<220> FEATURE:
<221> NAME/KEY: CDS
<222> LOCATION: (1)..(966)

<400> SEQUENCE: 6 atg gag gag gag aca gag ttc ctt gag ctc gga acc agg ata tca aga      48
Met Glu Glu Glu Thr Glu Phe Leu Glu Leu Gly Thr Arg Ile Ser Arg
1               5                   10                  15 cca aat gga cta ctg tca gag gat gta gga atg gac atc ccc ttt gaa     96
Pro Asn Gly Leu Leu Ser Glu Asp Val Gly Met Asp Ile Pro Phe Glu
                20                  25                  30 gag ggc gtg ctg agt ccc agt gct gca gac atg agg cct gaa cct cct    144
Glu Gly Val Leu Ser Pro Ser Ala Ala Asp Met Arg Pro Glu Pro Pro
            35                  40                  45 aat tct ctg gat ctt aat gac act cat cct cgg aga atc aag ctc aca    192
Asn Ser Leu Asp Leu Asn Asp Thr His Pro Arg Arg Ile Lys Leu Thr
        50                  55                  60 gcc cca aat atc aat ctt tct ctg gac caa agt gaa gga tct att ctc    240
Ala Pro Asn Ile Asn Leu Ser Leu Asp Gln Ser Glu Gly Ser Ile Leu
65                  70                  75                  80 tct gat gat aac ttg gac agt cca gat gaa att gac atc aat gtg gat    288
Ser Asp Asp Asn Leu Asp Ser Pro Asp Glu Ile Asp Ile Asn Val Asp
                85                  90                  95 gaa ctt gat acc ccc gat gaa gca gat tct ttt gag tac act ggc cat    336
Glu Leu Asp Thr Pro Asp Glu Ala Asp Ser Phe Glu Tyr Thr Gly His
            100                 105                 110 gat ccc aca gcc aac aaa gat tct ggc caa gag tca gag tct att cca    384
Asp Pro Thr Ala Asn Lys Asp Ser Gly Gln Glu Ser Glu Ser Ile Pro
        115                 120                 125 gaa tat acg gcc gaa gag gaa cgg gag gac aac cgg ctt tgg atg aca    432
Glu Tyr Thr Ala Glu Glu Glu Arg Glu Asp Asn Arg Leu Trp Met Thr
    130                 135                 140 gtg gtc att gga gaa caa gag cag cgc att gac atg aag gtc atc gag    480
Val Val Ile Gly Glu Gln Glu Gln Arg Ile Asp Met Lys Val Ile Glu
145                 150                 155                 160 ccc tac agg aga gtc att tct cac gga gga gat tca gga tac tat ggg    528
Pro Tyr Arg Arg Val Ile Ser His Gly Gly Asp Ser Gly Tyr Tyr Gly
                165                 170                 175 gac ggt cta aat gcc atc att gtg ttt gcc gcc tgt ttt ctg cca gac    576
Asp Gly Leu Asn Ala Ile Ile Val Phe Ala Ala Cys Phe Leu Pro Asp
            180                 185                 190 agc agt cgg gcg gat tac cac tat gtc atg gaa aat ctt ttc cta tat    624
Ser Ser Arg Ala Asp Tyr His Tyr Val Met Glu Asn Leu Phe Leu Tyr
        195                 200                 205 gta ata agt act tta gag ttg atg gta gct gaa gac tat atg att gtg    672
Val Ile Ser Thr Leu Glu Leu Met Val Ala Glu Asp Tyr Met Ile Val
    210                 215                 220
```

```
tac ttg aat ggt gca acc cca aga agg agg atg cca ggg cta ggc tgg    720
Tyr Leu Asn Gly Ala Thr Pro Arg Arg Arg Met Pro Gly Leu Gly Trp
225                 230                 235                 240 atg aag aaa tgc tac cag atg att gac aga cgg ttg agg aag aat ttg    768
Met Lys Lys Cys Tyr Gln Met Ile Asp Arg Arg Leu Arg Lys Asn Leu
                245                 250                 255 aaa tca ttc atc att gtt cat cca tct tgg ttc atc aga aca atc ctt    816
Lys Ser Phe Ile Ile Val His Pro Ser Trp Phe Ile Arg Thr Ile Leu
            260                 265                 270 gct gtg aca cga cct ttt ata agt tca aaa ttc agc agt aaa att aaa    864
Ala Val Thr Arg Pro Phe Ile Ser Ser Lys Phe Ser Ser Lys Ile Lys
        275                 280                 285 tat gtc aat agc tta tca gaa ctc agt ggg ctg atc cca atg gat tgc    912
Tyr Val Asn Ser Leu Ser Glu Leu Ser Gly Leu Ile Pro Met Asp Cys
    290                 295                 300 atc cac att cca gag agc atc atc aat att gac ttg aag ctg aaa gaa    960
Ile His Ile Pro Glu Ser Ile Ile Asn Ile Asp Leu Lys Leu Lys Glu
305                 310                 315                 320 aag cct                                                            966
Lys Pro

<210> SEQ ID NO 7
<211> LENGTH: 2966
<212> TYPE: DNA
<213> ORGANISM: Homo sapiens
<220> FEATURE:
<221> NAME/KEY: CDS
<222> LOCATION: (56)..(433)

<400> SEQUENCE: 7
gtcgacccac gcgtccgggc gaatctgtat ttccagttaa ctgctcagaa gagag atg     58
                                                               Met
                                                                 1 ctg aag agc tgt agt cgt gca tcc ttc tca ccc tcc gtt aga aag cct    106
Leu Lys Ser Cys Ser Arg Ala Ser Phe Ser Pro Ser Val Arg Lys Pro
            5                   10                  15 cct ctc atc ctc aga aga cta ctg tca gag gat gta gga atg gac atc    154
Pro Leu Ile Leu Arg Arg Leu Leu Ser Glu Asp Val Gly Met Asp Ile
        20                  25                  30 ccc ttt gaa gag ggc gtg ctg agt ccc agt gct gca gac atg agg cct    202
Pro Phe Glu Glu Gly Val Leu Ser Pro Ser Ala Ala Asp Met Arg Pro
    35                  40                  45 gaa cct cct aat tct ctg gat ctt aat gac act cat cct cgg aga atc    250
Glu Pro Pro Asn Ser Leu Asp Leu Asn Asp Thr His Pro Arg Arg Ile
50                  55                  60                  65 aag ctc aca gcc cca aat atc aat ctt tct ctg gac caa agt gaa gga    298
Lys Leu Thr Ala Pro Asn Ile Asn Leu Ser Leu Asp Gln Ser Glu Gly
                70                  75                  80 tct att ctc tct gat gat aac ttg gac agt cca gat gaa att gac atc    346
Ser Ile Leu Ser Asp Asp Asn Leu Asp Ser Pro Asp Glu Ile Asp Ile
            85                  90                  95 aat gtg gat gaa ctt gat acc ccc gat gaa gca gat tct ttt gag tac    394
Asn Val Asp Glu Leu Asp Thr Pro Asp Glu Ala Asp Ser Phe Glu Tyr
        100                 105                 110 act ggc cat ggt aag tca cta agt tgg caa ggc caa agt taaatgctaa     443
Thr Gly His Gly Lys Ser Leu Ser Trp Gln Gly Gln Ser
    115                 120                 125 ataagtaaaa gattttctaa cagacctctc attttgtgc cagtggatcc ttttgtgat    503 ttctagaagc ttctgttttt atttcaggtt ataggtggcc atgattgaca gtttggagcc    563
tgacagagaa agtatgggtc acagaggcca tacataacca ttgctcttta ttaaccccca    623
```

-continued

```
ctctgtgcta gcatttatgc taggcactgg ggctgaggga agactgttac atgctgtgtt    683
acaagaaacc tggggctggg tttgcagggg aagagaattt aatcaggatg ataaaatttg    743
aagaagagaa atcagagctt gccaatttct tgtataagtt cccactatct gcaatgttct    803
tttccccaga tccttacgtg actgactcct tctctttatt cagatgttaa tcagatgtca    863
cctcctcaga gaagtcttcc ttgacctctg taatcaaaga tgcttcccac ttcccgactc    923
ccaccaccta gtcactctct gtcccagtgt tcattttatt ttccacgtat cactaattca    983
aattgtatta tttaactatt tgtttgcatc tttattgtct ttctcttacc actcgaatgt   1043
atgctccaca ggagcaagga ctttatattt gatcctgcgt ctccaataaa gtgggaagga   1103
aggaagggat ggtttagggg gagtgagaga aatgataaaa aagaagataa ttaaaagttt   1163
tcagatcatc caagactgac actcctgata tgaacttcag tctttcttta gttctttctc   1223
ttactctatg aaatctggtt taagaaatat gtacaaatac aatcattttt ttttaaatgg   1283
cattatgtag tttctgtttc agttctagcc agggtggaat tctctgaagt tataatattt   1343
gaaagtgaaa gcgagagagt ctgggacaca gctattgctt ttattcattt ttaaaattca   1403
cgcaatctta aaagcaatac agtgccacaa ttaagtggtg gcctgacttt tagagacatg   1463
ctaattctag cagttccact cctagaagag cataattaga aaattcacca aattagctaa   1523
ttatttcaac caatggtcat tgagccgaca tgagcagtgc agttcagact ctaccttgac   1583
agagcttaag gctttatttc ctcaaaaagg aaatggctaa acgacttgtt ttatagtcta   1643
ttatgcttaa gtagagtttt ttttttttcc ataagttatt ggggtacagg tggtatttgg   1703
ttacatgagt aagttcttta gtgtaagtag agatttata ttgcattttt atcatgtgtg   1763
aatttctgta gttatctggg tagttgattc tgtaggttga aatacacaaa taggaggtga   1823
aagaaggtct ggaatttgta ctatttcctg tcatcccaga gagtcttcag cagctcctct   1883
atccatccca gttgccccct accagctcct gctcctttcc ctgctaatat attgaccaaa   1943
tcccacagaa gactgtggca tgacccaact ggcccctctc ttgcctccgg tatttgcttc   2003
cttttttgtca ggagagcttt gtcacaccac atctgaacct tttattttta aacatagtaa   2063
aactgtcgag caaagcagtg gtggctgggc aagctggtaa ttaacactgc cacttgctga   2123
catggctctt ttaatgtagt taacatagct gtgttgaaag aaccagttta atggccacaa   2183
ccctgtttta ggtcttaaat gcaaaggaca gaattgtaaa ctaagttgaa ttttttaaatc   2243
taccttaatt ttcaaatgaa agatatatag tcagaggttg aaactttgaa aacacaaagt   2303
gcctctgaat agctatattt tgtaaacatg aggacatgga taagtgactg tataagaggg   2363
ttggattata aatatgtttg agttctgaag tatgaaataa atgctgaaa gcagcctgtt   2423
tcttaggttt ctcacgcgac catttgaac caggaatgta cattctaaac aaaatagggg    2483
ttttaaggt atagttttc aaaaacattt gggccataat ttatttcttt ttaatgaata    2543
cttttcatt tatattatat ttttcgtgta tatattca ttatatacgt ttcattatat    2603
attatatatt tgtactatat attttcatt tatatagttt tcattgtata ttatatacct   2663
cattatatta tataattcat tatatagttt tcattaatt tatttcattt taatactaga   2723
acaatgaagc acagagaagt taagtaattt gcctaaggtc acacagctca ttgttgccct   2783
tagttcctgg cccatgctgc ttcccagtga atatgctaac aatgaatggg aaagggtctg   2843
ttaccagatt ggacttacat acttgaagcc aaacatgata gctcttgctc acatttaggc   2903
ctctttttat ccagtttttcc tgacttgcgg gagactctaa aaaaaaaaaa aagggcggc   2963
```

-continued cgc 2966

<210> SEQ ID NO 8
<211> LENGTH: 126
<212> TYPE: PRT
<213> ORGANISM: Homo sapiens

<400> SEQUENCE: 8

```
Met Leu Lys Ser Cys Ser Arg Ala Ser Phe Ser Pro Ser Val Arg Lys
  1               5                  10                  15

Pro Pro Leu Ile Leu Arg Arg Leu Leu Ser Glu Asp Val Gly Met Asp
             20                  25                  30

Ile Pro Phe Glu Glu Gly Val Leu Ser Pro Ser Ala Ala Asp Met Arg
         35                  40                  45

Pro Glu Pro Pro Asn Ser Leu Asp Leu Asn Asp Thr His Pro Arg Arg
     50                  55                  60

Ile Lys Leu Thr Ala Pro Asn Ile Asn Leu Ser Leu Asp Gln Ser Glu
 65                  70                  75                  80

Gly Ser Ile Leu Ser Asp Asp Asn Leu Asp Ser Pro Asp Glu Ile Asp
                 85                  90                  95

Ile Asn Val Asp Glu Leu Asp Thr Pro Asp Glu Ala Asp Ser Phe Glu
            100                 105                 110

Tyr Thr Gly His Gly Lys Ser Leu Ser Trp Gln Gly Gln Ser
        115                 120                 125
```

<210> SEQ ID NO 9
<211> LENGTH: 378
<212> TYPE: DNA
<213> ORGANISM: Homo sapiens
<220> FEATURE:
<221> NAME/KEY: CDS
<222> LOCATION: (1)..(378)

<400> SEQUENCE: 9

```
atg ctg aag agc tgt agt cgt gca tcc ttc tca ccc tcc gtt aga aag        48
Met Leu Lys Ser Cys Ser Arg Ala Ser Phe Ser Pro Ser Val Arg Lys
  1               5                  10                  15 cct cct ctc atc ctc aga aga cta ctg tca gag gat gta gga atg gac        96
Pro Pro Leu Ile Leu Arg Arg Leu Leu Ser Glu Asp Val Gly Met Asp
             20                  25                  30 atc ccc ttt gaa gag ggc gtg ctg agt ccc agt gct gca gac atg agg       144
Ile Pro Phe Glu Glu Gly Val Leu Ser Pro Ser Ala Ala Asp Met Arg
         35                  40                  45 cct gaa cct cct aat tct ctg gat ctt aat gac act cat cct cgg aga       192
Pro Glu Pro Pro Asn Ser Leu Asp Leu Asn Asp Thr His Pro Arg Arg
     50                  55                  60 atc aag ctc aca gcc cca aat atc aat ctt tct ctg gac caa agt gaa       240
Ile Lys Leu Thr Ala Pro Asn Ile Asn Leu Ser Leu Asp Gln Ser Glu
 65                  70                  75                  80 gga tct att ctc tct gat gat aac ttg gac agt cca gat gaa att gac       288
Gly Ser Ile Leu Ser Asp Asp Asn Leu Asp Ser Pro Asp Glu Ile Asp
                 85                  90                  95 atc aat gtg gat gaa ctt gat acc ccc gat gaa gca gat tct ttt gag       336
Ile Asn Val Asp Glu Leu Asp Thr Pro Asp Glu Ala Asp Ser Phe Glu
            100                 105                 110 tac act ggc cat ggt aag tca cta agt tgg caa ggc caa agt              378
Tyr Thr Gly His Gly Lys Ser Leu Ser Trp Gln Gly Gln Ser
        115                 120                 125
```